US007425537B2

(12) United States Patent
Burke, Jr. et al.

(10) Patent No.: US 7,425,537 B2
(45) Date of Patent: Sep. 16, 2008

(54) SH2 DOMAIN BINDING INHIBITORS

(75) Inventors: Terrence R Burke, Jr., Bethesda, MD (US); Chang-Qing Wei, Ottawa (CA); Zhen-Dan Shi, Frederick, MD (US); Yang Gao, Madison, CT (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 274 days.

(21) Appl. No.: 10/517,717

(22) PCT Filed: Jun. 26, 2003

(86) PCT No.: PCT/US03/19987

§ 371 (c)(1),
(2), (4) Date: Mar. 17, 2005

(87) PCT Pub. No.: WO2004/003005

PCT Pub. Date: Jan. 8, 2004

(65) Prior Publication Data
US 2006/0167222 A1 Jul. 27, 2006

Related U.S. Application Data

(63) Continuation-in-part of application No. 10/362,231, filed as application No. PCT/US01/26078 on Aug. 22, 2001, now Pat. No. 6,977,241.

(60) Provisional application No. 60/392,028, filed on Jun. 28, 2002, provisional application No. 60/226,671, filed on Aug. 22, 2000.

(51) Int. Cl.
*A61K 38/12* (2006.01)
*C07K 5/12* (2006.01)
*C07K 1/00* (2006.01)

(52) U.S. Cl. ............... 514/11; 530/317; 530/333

(58) Field of Classification Search ............ None
See application file for complete search history.

(56) References Cited

U.S. PATENT DOCUMENTS

| | | |
|---|---|---|
| 3,906,031 A | 9/1975 | Carpino et al. |
| 4,394,519 A | 7/1983 | Carpino et al. |
| 4,598,087 A | 7/1986 | Horwell |
| 4,879,398 A | 11/1989 | Getman et al. |
| 4,885,316 A | 12/1989 | Rothgery et al. |
| 5,132,409 A | 7/1992 | Felder et al. |
| 5,182,263 A | 1/1993 | Danho et al. |
| 5,200,546 A | 4/1993 | Burke, Jr. et al. |
| 5,272,268 A | 12/1993 | Toyoda et al. |
| 5,296,608 A | 3/1994 | Danho et al. |
| 5,304,552 A | 4/1994 | Hanson |
| 5,369,110 A | 11/1994 | Schmidlin et al. |
| 5,457,111 A | 10/1995 | Luly et al. |
| 5,457,114 A | 10/1995 | Stüber et al. |
| 5,463,062 A | 10/1995 | Hemmerle et al. |
| 5,475,129 A | 12/1995 | Burke, Jr. et al. |
| 5,491,253 A | 2/1996 | Stuk et al. |
| 5,508,437 A | 4/1996 | Danho et al. |
| 5,525,733 A | 6/1996 | Novack et al. |
| 5,554,749 A | 9/1996 | Wallace et al. |
| 5,580,979 A | 12/1996 | Bachovchin |
| 5,587,372 A | 12/1996 | Aszodi et al. |
| 5,612,370 A | 3/1997 | Atwal |
| 5,616,776 A | 4/1997 | Stuk et al. |
| 5,624,949 A | 4/1997 | Heath, Jr. et al. |
| 5,627,283 A | 5/1997 | Stüber et al. |
| 5,646,036 A | 7/1997 | Schwall et al. |
| 5,676,923 A | 10/1997 | Platzek et al. |
| 5,679,842 A | 10/1997 | Kleiner |
| 5,686,292 A | 11/1997 | Schwall et al. |
| 5,688,992 A | 11/1997 | Burke, Jr. et al. |
| 5,698,731 A | 12/1997 | Bosetti et al. |

(Continued)

FOREIGN PATENT DOCUMENTS

WO    WO 94/07913    4/1994

(Continued)

OTHER PUBLICATIONS

T Gura. Science (1997) 278, pp. 1041-1042.*
R McKie. The Observer (2001). 4 pages.*
C Gorman, et al. Time (May 18, 1998) 151, 9 Pages.*
GB Dermer. Bio/Technology (1994) p. 320.*
Ye et al., "L-O-(2-Malonyl)tyrosine" A New Phosphotyrosyl Mimetic for the Preparation of Src Homology 2 Domain Inhibitory Peptides, J. Med. Chem. vol. 38, pp. 4270-4275, 1995.
Burke, Jr., et al., "4'-O-[2-(2-Fluoromalonyl)]-L-tyrosine: A Phosphotyrosyl Mimic for the Preparation of Signal Transduction Inhibitory Peptides", J. Med. Chem., vol. 39, pp. 1021-1027, Mar. 1, 1996.

(Continued)

*Primary Examiner*—Andrew D Kosar
(74) *Attorney, Agent, or Firm*—Leydig, Voit & Mayer, Ltd.

(57) ABSTRACT

Disclosed are compounds for SH2 domain binding inhibition, for example, a compound of formula (I), wherein $R_1$ is a lipophile; $R_2$, in combination with the phenyl ring, is a phenylphosphate mimic group or a protected phenylphosphate mimic group; $R_3$ is hydrogen, azido, amino, carboxyalkyl, alkoxycarbonylalkyl, aminocarbonylalkyl, or alkylcarbonylamino, wherein the alkyl portion of $R_3$ may be optionally substituted with a substituent selected from the group consisting of halo, hydroxy, carboxyl, amino, aminoalkyl, alkyl, alkoxy, and keto; $R_6$ is a linker; AA is an amino acid; and n is 1 to 6; or a salt thereof. The conformationally compounds provide enhanced binding affinity with SH2 domain protein. Also disclosed are a pharmaceutical compositions and a method for inhibiting an SH2 domain from binding with a phosphoprotein.

15 Claims, 28 Drawing Sheets

U.S. PATENT DOCUMENTS

| | | | |
|---|---|---|---|
| 5,707,624 | A | 1/1998 | Nickoloff et al. |
| 5,710,129 | A | 1/1998 | Lynch et al. |
| 5,710,173 | A | 1/1998 | Tang et al. |
| 5,712,395 | A | 1/1998 | App et al. |
| 5,714,361 | A | 2/1998 | Widlanski |
| 5,721,361 | A | 2/1998 | Lennon et al. |
| 5,741,777 | A | 4/1998 | Grinnell et al. |
| 5,753,687 | A | 5/1998 | Mjalli et al. |
| 5,756,817 | A | 5/1998 | Choi et al. |
| 5,773,411 | A | 6/1998 | Wells et al. |
| 5,780,496 | A | 7/1998 | Tang et al. |
| 5,786,454 | A | 7/1998 | Waksman et al. |
| 5,789,427 | A | 8/1998 | Chen et al. |
| 5,792,771 | A | 8/1998 | App et al. |
| 5,792,783 | A | 8/1998 | Tang et al. |
| 5,834,504 | A | 11/1998 | Tang et al. |
| 5,843,997 | A | 12/1998 | Heinz et al. |
| 5,847,135 | A | 12/1998 | Bemis et al. |
| 5,849,693 | A | 12/1998 | Wells et al. |
| 5,849,742 | A | 12/1998 | App et al. |
| 5,859,002 | A | 1/1999 | Kalish et al. |
| 5,880,141 | A | 3/1999 | Tang et al. |
| 5,883,110 | A | 3/1999 | Tang et al. |
| 5,883,113 | A | 3/1999 | Tang et al. |
| 5,883,116 | A | 3/1999 | Tang et al. |
| 5,886,020 | A | 3/1999 | Tang et al. |
| 5,886,195 | A | 3/1999 | Tang et al. |
| 5,891,917 | A | 4/1999 | Tang et al. |
| 5,912,183 | A | 6/1999 | Comoglio et al. |
| 5,916,749 | A | 6/1999 | Bandman et al. |
| 5,935,993 | A | 8/1999 | Tang et al. |
| 5,936,084 | A | 8/1999 | Jirousek et al. |
| 5,952,320 | A | 9/1999 | Davidsen et al. |
| 5,958,957 | A | 9/1999 | Andersen et al. |
| 5,965,558 | A | 10/1999 | Mjalli et al. |
| 5,972,978 | A | 10/1999 | Andersen et al. |
| 5,981,569 | A | 11/1999 | App et al. |
| 6,037,134 | A | 3/2000 | Margolis |
| 6,127,391 | A | 10/2000 | Hansen et al. |
| 6,136,542 | A | 10/2000 | Demers et al. |
| 6,180,619 | B1 | 1/2001 | Kim |
| 6,228,986 | B1 | 5/2001 | Lanter et al. |
| 6,307,090 | B1 | 10/2001 | Burke, Jr. et al. |
| 6,545,038 | B1 | 4/2003 | De et al. |
| 6,977,241 | B2 * | 12/2005 | Burke et al. ............ 514/9 |

FOREIGN PATENT DOCUMENTS

| | | |
|---|---|---|
| WO | WO 95/11917 | 5/1995 |
| WO | WO 96/23813 | 8/1996 |
| WO | WO 97/08193 | 3/1997 |
| WO | WO 97/12903 | 4/1997 |
| WO | WO 98/17683 | 4/1998 |
| WO | WO 00/56760 | 9/2000 |
| WO | WO 00/73326 | 12/2000 |
| WO | WO 01/28577 A2 | 4/2001 |
| WO | WO 01/30325 | 5/2001 |
| WO | WO 02/16407 | 2/2002 |
| WO | WO 02/20525 | 3/2002 |
| WO | WO 02/40684 | 5/2002 |
| WO | WO 02/056837 | 7/2002 |

OTHER PUBLICATIONS

Schoepfer et al., "Structure-based Design of Peptidomimetic Ligands of Grb2-SH2 Domain", Bioorganic & Medicinal Chemistry Letters 8, pp. 2865-2870, 1998.

Yao et al., "Potent Inhibition of Grb2 SH2 Domain Binding by Non-Phosphate-Containing Ligands", J. Med. Chem., vol. 42, pp. 25-35, 1999.

Gay et al., "Effect of Potent and Selective Inhibitors of the Grb2 SH2 Domain on Cell Motility", The Journal of Biological Chemistry, vol. 274, pp. 23311-23315, Aug. 13, 1999.

Schoepfer et al., "Highly Potent Inhibitors of the Grb2-SH2 Domain", Bioorganic & Medicinal Chemistry Letters 9, pp. 221-226, 1999.

Burke, Jr., et al., Monocarboxylic-Based Phosphotyrosyl Mimetics in the Design of Grb2 SH2 Domain Inhibitors, Bioorganic & Medicinal Chemistry Letters 9, pp. 347-352, 1999.

Gilmer et al., "Peptide Inhibitors of src SH-3-SH2-Phosphorprotein Interactions", The Journal of Biological Chemistry, vol. 269, pp. 31711-31719, Dec. 16, 1994.

Charifson et al., "Peptide Ligands of $pp60^{c-src}$ SH2 Domains: A Thermodynamic and Structural Study", Biochemistry, vol. 36, pp. 6283-6293, 1997.

Liu et al., "Synthesis of L-2,3,5,6-Tetrafluoro-4-(Phosphonomethyl) Phenylalanine, a Novel Non-Hydrolyzable Phosphotyrosine Mimetic and L-4-(Phosphonodifluoromethyl)Phenylalanine", Tetrahedron Letters, vol. 38, pp. 1389-1392, 1997.

Cleland, "The Meerwein Reaction in Amino Acid Synthesis. II. An Investigation of Twenty-one Substituted Anilines", The Journal of Organic Chemistry, Vo., 34, pp. 744-747, Mar. 1969.

Gao et al., Inhibition of Grb2 SH2 Domain Binding by Non-Phosphate-Containing Ligands. 2. 4-(2-Malonyl)phenylalanine as a Potent Phosphotyrosyl Mimetic, J. Med. Chem., vol. 43, pp. 911-920, 2000.

Furet et al., Structure-Based Design and Synthesis of High Affinity Tripeptide Ligands of the Grb2-SH2 Domain, J. Med. Chem., vol. 41, pp. 3442-3449, 1998.

Tong et al., "Carboxymethyl-phenylalanine as a Replacement for Phosphotyrosine in SH2 Domain Binding", The Journal of Biological Chemistry, vol. 273, pp. 20238-20242 Aug. 7, 1998.

Kim et al., FEBS Lett, 453, 174-178, 1999.

Tulasne et al., "The Multisubstrate Docketing Site of the MET Receptor is Dispensable for MET-mediated RAS Signaling and Cell Scattering", Molecular Biology of the Cell, vol. 10, pp. 551-565, Mar. 1999.

Kim et al., "Dual Signaling Role of the Protein Tyrosine Phosphatase SHP-2 in Regulating Expression of Acute-Phase Plasma Proteins by Interleukin-6 Cytokine Receptors in Hepatic Cells", Molecular and Cellular Biology, vol. 19, pp. 5326-5338, Aug. 1999.

Nguyen et al., "Association of the Multisubstrate Docking Protein Gab1 with the Hepatocyte Growth Factor Receptor Requires a Functional Grb2 Binding Site Involving Tyrosine 1356", The Journal of Biological Chemistry, vol. 272, pp. 20811-20819, Aug. 15, 1997.

Maina et al., "Uncoupling of Grb2 from the Met Receptor in Vivo Reveals Complex roles in Muscle Development", Cell, vol. 87, pp. 531-542, Nov. 1, 1996.

Ponzetto et al., "Specific Uncoupling of GRB2 from the Met Receptor", The Journal of Biological Chemistry, vol. 271, pp. 14119-14123, Jun. 14, 1996.

Ettmayer et al., "Structural and Conformational Requirements for High-Affinity Binding to the SH2 Domain of Grb2", J. Med. Chem., vol. 42, pp. 971-980, 1999.

Royal et al., "Differential Requirement of Grb2 and P13-Kinase in HGF/SF-Induced Cell Motility and Tubulogenesis", Journal of Cellular Physiology, vol. 173, pp. 196-201, 1997.

Gao et al., Biorg & Med Chem Lett, 10, 923-927 (2000).

Burke, Jr., et al., "Preparation of . . . Peptide Synthesis", J. of Synthetic Organic Chem., No. 11, p. 1019, Nov. 11, 1991.

Burke, Jr., et al., "Potent Inhibition of Grb2 SH2 domain Binding by Non-Phosphate containing Ligands", First Annual Meeting on the Experimental Therapeutics of Human Cancer, Jun. 11-13, 1998, Hood College, Frederick Maryland (Summary).

Katunuma et al., "Use of new synthetic substrates for assays of cathepsin L and cathepsin B", J. Biochem. (Tokyo), vol. 93, pp. 1129-1135, 1983 (Abstract only).

Burke, Jr., et al., "Enantioselective Synthesis . . . Inhibitory Peptides", Tetrahedron, vol. 54, pp. 9981-9994, 1998.

Burke, Jr., et al., "Phosphotyrosyl-Based Motifs in the Structure-Based Design of Protein-Tyrosine Kinase-Dependent Signal Transduction Inhibitors", Current Pharmaceutical Design, vol. 3, pp. 291-304, 1997.

Burke, Jr., et al., "Nonhydrolyzable Phosphotyrosyl Mimetics for the Preparation of Phosphatase-Resistant SH2 Domain Inhibitors", Biochemistry, vol. 33, pp. 6490-6494, 1994.

Ye et al., "L-O-(2-Malonyl)tyrosine (L-OMT) a New Phosphotyrosyl Mimic Suitably Protected for Solid-Phase Synthesis of Signal Transduction Inhibitory Peptides", Tetrahedron Letters, vol. 36, pp. 4733-4736, 1995.

Kuriyan, "Modular Peptide recognition Domains in Eukaryotic Signaling", Annu. Rev. Biophys. Biomol. Struct., vol. 26, pp. 259-288, 1997.

Mayer et al., "Functions of SH2 and SH3 Domains", Protein modules in signal transduction, edited by A. J. Pawson, Berlin, New York, Springer, c1998; 00. 1-22.

Fry et al., "New insights into protein-tyrosine kinase receptor signaling complexes", Protein Science, vol. 2, pp. 1785-1797, 1993.

Levitzki, "Targeting signal tranduction for disease therapy", Current Opinion in Cell Biology, vol. 8, pp. 239-244, 1996.

Boutin, "Tyrosine Protein Kinase Inhibition and Cancer", Int. J. Biochem., vol. 26, pp. 1203-1226, 1994.

Levitzki et al., "Tyrosine Kinase Inhibition: An Approach to Drug Development", Science, vol. 267, pp. 1782-1788, Mar. 24, 1995.

Lawrence et al., "Protein Kinase Inhibitors: The Tyrosine-specific Protein Kinases", Pharmacol. Ther., vol. 77, pp. 81-114, 1998.

Burke, Jr., et al., "Protein-Tyrosine Phosphatases: Structure, Mechanism, and Inhibitor Discovery", Biopolymers (Peptide Science), vol. 47, pp. 225-241 (1998).

Schoelson, "SH2 and PTB domain interactions in tyrosine kinase signal transduction", Current Opinion in Chemical Biology, vol. 1, pp. 227-234, 1997.

Waksman et al., "Crystal structure of the phosphotyrosine recognition domain Sh2 of v-src complexed with tyrosine-phosphorylated peptides", Nature, vol. 358, pp. 646-653, Aug. 20, 1992.

Waksman et al., "Binding of High Affinity Phosphotyrosyl Peptide to the Src SH2 Domain: Crystal Structures of the Complexed and Peptide-free Forms", Cell, vol. 72, pp. 779-790, Mar. 12, 1993.

Mikol et al., "The Crystal Structures of the SH2 Domain of p56[ick] Complexed with Two Phosphonopeptides Suggest a Gated Peptide Binding Site", J. Mol. Viol. vol. 246, pp. 344-355, 1995.

Hatada et al., "Molecular basis for interaction of the protein tyrosine kinase ZAP-70 with the T-cell receptor", Nature, vol. 377, pp. 32-38, Sep. 7, 1995.

Zhou et al., "Solution structure of the Shc SH2 domain complexed with a tyrosine-phosphorylated peptide from the T-cell receptor", Proc. Natl. Acad. Sci., vol. 92, pp. 7784-7788, Aug. 1995.

Narula et al., "Solution structure of the C-terminal SH2 domain of the human tyrosine kinase Syk complexed with a phosphotyrosine pentapeptide", Structure, vol. 3, 1061-1073, Oct. 15, 1995.

Xu et al., "Solution Structure of the Human pp60[c-src] SH2 Domain Complexed with a Phosphorylated Tyrosine Pentapeptide", Biochemistry, vol. 34, pp. 2107-2121, 1995.

Tong et al., "Crystal Structures of the Human p56[ick] SH2 Domain in Complex with Two Short Phosphotyrosyl Peptides at 1.0 Å and 1.8 Å Resolution", Academic Press Limited, 10 pages, 1996.

Sicheri et al., "Crystal structure of the Src family tyrosine kinase Hck", Nature, vol. 385, pp. 602-609, Feb. 13, 1997.

Chen et al., "Crystal Structure of a Tyrosine Phosphorylated STAT-1 Dimer Bound to DNA", Cell, vol. 93, pp. 827-839, May 29, 1998.

Songyang et al., "Recognition and specificity in protein tyrosine kinase-medicated signalling", Elsevier Science Ltd., pp. 470-475, 1995.

Lunney et al., "Structure-Based Design of a Novel Series of Nonpeptide Ligands That Bind to the pp60[src] SH2 Domain", J. Am. Chem. Soc., vol. 119, pp. 12471-12476, 1997.

Pacofsky et al., "Potent Dipeptide Inhibitors of the pp60[c-src] SH2 Domain", J. Med. Chem., vol. 41, pp. 1894-1908, 1998.

Marseigne et al., "Synthesis of New Amino Acids Mimicking Sulfated and Phosphorylated Tyrosine Residues", J. Org. Chem., vol. 53, pp. 3621-3624, 1988.

Domchek et al., "Inhibition of SH2 Domain/Phosphoprotein Association by a Nonhydrolyzable Phosphonopeptide", Biochemistry, vol. 31, pp. 9865-9870, 1992.

Xiao et al., "Syp (SH-PTP2) Is a Positive Mediator of Growth Factor-stimulated Mitogenic Signal Transduction", The Journal of Biological Chemistry, vol. 269, pp. 21244-21248, Aug. 19, 1994.

Wange et al., "$F_2$(Pmp)$_2$-TAM$\zeta_3$, a Novel Competitive Inhibitor of the binding of ZAP-70 to the T Cell Antigen Receptor, Blocks Early T Cell Signaling", JBC Online, vol. 270, pp. 944-948, Jan. 13, 1995.

Rojas et al., "Controlling Epidermal Growth Factor (EGF)-stimulated Ras Activation in Intact Cells by a Cell-permeable Peptide Mimicking Phosphorylated EGF Receptor", The Journal of Biological Chemistry, vol. 271, pp. 27456-27461, Nov. 1, 1996.

Williams et al., "Selective Inhibition of Growth Faxtor-stimulated Mitogenesis by a Cell-permeable Grb2-binding Peptide", The Journal of Biological Chemistry, vol. 272, pp. 22349-22354, Aug. 29, 1997.

Stankovic, "The Role of 4-Phosphonodifluoromethyl- and 4-Phosphono-Phenylalanine in the Selectivity and Cellular Uptake of SH2 domain Ligands", Bioorganic & Medicinal Chemistry Letters, vol. 7, pp. 1909-1914, 1997.

Mehrotra et al., "α-Dicarbonyls as "Non-Charged" Arginine-Directed Affinity Labels", Bioorganic & Medicinal Chemistry Letters, vol. 6, pp. 1941-1946, 1996.

Margolis, "The GRB Family of SH2 domain Proteins", Prog. Biophys. Molec. Biol., vol. 62, pp. 223-244, 1994.

Burke, Jr., et al., "Preparation of Fluoro- and Hydroxy-4-(phosphonomethyl)-D,L-phenylalanine Suitably Protected for Solid-Phase Synthesis of Peptides Containing Hydrolytically Stable Analogues of O-Phosphotyrosine", Jour. Of Organic Chemistry, pp. 1336-1340, Mar. 12, 1993.

Burke, Jr., et al., "Synthesis of 4-Phosphono(difluoromethyl)-D,L-phenylalanine and N-Boc and N-Fmoc Derivatives Suitably Protected for solid-Phase Synthesis of Nonhydrolyzable Phosphotyrosyl Peptide Analogues", Tetrahedron Letters, vol. 34, pp. 4125-4128, 1993.

Smyth et al., "Enanthioselective Synthesis of N-Boc and N-Fmoc Protected Diethyl 4-Phosphono(difluoromethyl)-L-Phenylalanine; Agents Suitable for the Solid-Phase Synthesis of Peptides Containing Nonhydrolyzable Analogues of O-Phosphotyrosine", Tetrahedron letters, vol. 35, pp. 551-554, 1994.

Miller et al., "EPSP Synthase . . . 3-Phosphate Mimics", J. Organic & Medicinal Chem. Letters, vol. 3, No. 7, pp. 1435-1440, 1993.

"Synthesis and . . . containing peptides", Chem. Abs., vol. 123, No. 257331h, p. 1220, 1995.

Furet et al., "Discovery of 3-Aminobenzyloxycarbonyl as an N-Terminal Group conferring High Affinity to the Minimal Phosphopeptide Sequence Recognized by the Grb-2-SH2 Domain", J. Med. Chem., vol. 40, pp. 3551-3556, 1997.

Rahuel et al., "Structural Basis for the High Affinity of Amino-Aromatic SH2 Phosphopeptide Ligands", J. Mol. Biol., 279, pp. 1013-1022, 1998.

Garcia-Echeverria et al., "Potent Antagonists of the SH2 Domain of Grb2: Optimization of the $X_{+1}$-Position of 3-Amino-Z-Tyr(PO$_3$H$_2$)-$X_{=1}$-Asn-NH$_2$", Journal of Medicinal Chemistry, vol. 41, pp. 1741-1744, May 21, 1998.

Rahuel et al., "Structural basis for specificity of GRB-2-SH2 revealed by a novel ligand binding mode", Nature Structural Biology, vol. 3, No. 7, pp. 586-589, Jul. 7, 1996.

Oligino et al., "Nonphosphorylated . . . 2 Domain", The J. of Biological Chem., vol. 272, No. 46, pp. 29046-29052, Nov. 14, 1997.

Allen et al., "Tritiated Peptides. Part 15. Synthesis of Tritium Labelled Biologically Active Analogues of Somatostatin", J. Chem. Soc., Perkin Trans. 1, pp. 989-1003, 1986.

Ben-Levy et al., "A single autophosphorylation site confers oncogenicity to the Neu/Erb-2 receptor and enables coupling to the MAP Kinase pathway", The EMBO Journal, vol. 13, pp. 3302-3311, 1994.

Dankort et al., Distinct Tyrosine Autophosphorylation Sites Negatively and Positively Modulate New-Mediated Transformation, Molecular and Cellular Biology, vol. 17, pp. 5410-5425, Sep. 1997.

Ma et al., "Bcr phosphorylated on tyrosine 177 binds Grb2", Oncogene, vol. 14, pp. 2367-2372, 1997.

DiFiore et al., "Overexpression of the Human EGF Receptor confers an EGF-Dependent Transformed Phenotype to NIH 3T3 Cells", Cell, vol. 51, pp. 1063-1070, Dec. 24, 1987.

Hudziak et al, "Increased expression of the putative growth factor receptor p185[HER2] causes transformation and tumorigenesis of NIH 3T3 cells", Proc. Natl. Acad. Sci., vol. 84, pp. 7159-7163, Oct. 1987.

Kraus et al., "Overexpression of the EGF receptor-related proto-oncogene erbB-2 in human mammary tumor cells lines by different molecular mechanisms", The EMBO Journal, vol. 6, pp. 605-610, 1987.

Sastry et al., "Quantitative analysis of Grb2-Sos1 interaction: the N-terminal SH3 domain of Grb2 mediates affinity", Oncogene, 11, pp. 1107-1112, 1995.

Searles, The Reaction of Trimethylene Oxide with Grignard Reagents and Organolithium Compounds, J. Amer. Chem. Soc., vol. 73, pp. 124-125, 1951.

Fretz et al., "Targeting a Hydrophobic Patch on the Surface of the Grb2-SH2 Domain", 15th Amer. Peptide Symposium, Nashville, TN, Jun. 1997, Abstract No. P422.

Fixman et al., "Efficient Cellular . . . Proteins, Cb1 and Gab1", The J. of Biological Chem., vol. 272, No. 32, pp. 20167-20172, Aug. 8, 1997.

Tari et al., "Inhibition of Grb2 . . . Leukemic Cells", Biochemical and Biophysical Research Communications, vol. 235, pp. 383-388, Article No. RC97691, 1997.

Xie et al., "Dominant-negative Mutants . . . Rat *HER*-2/Neu", The J. of Biological Chem., vol. 270, No. 51, pp. 30717-30724, Dec. 22, 1995.

Maignan et al., "Crystal Structure of the Mammalian Grb2 Adaptor", Science, vol. 268, pp. 291-293, Apr. 14, 1995.

Saltiel et al., "Targeting signal transduction in the discovery of antiproliferative drugs", Chemistry & Biology, vol. 3, No. 11, pp. 887-893, Nov. 1996.

McNemar et al., Thermodynamic and . . . Binding to Grb2-SH2:, Biochemistry, vol. 36, pp. 10006-10014, 1997.

Ogura et al., "Conformation of an . . . Grb2 SH2 domain", J. of Biomolecular NMR, vol. 10, pp. 273-278, 1997.

Gay et al.; "Dual Specificity of . . . Peptide Ligands"; Biochemistry; vol. 36, pp. 5712-5718, 1997.

Bobko et al., "CD45 Protein . . . Irreversible Inhibitors", Bioorganic & Medicinal Chem. Letters, vol. 5, No. 4, pp. 353-356, 1995.

Burke et al., "Conformationally Constrained . . . 2 Domain Inhibitors", J. Med. Chem., vol. 38, pp. 1386-1396, 1995.

Chemical Abstracts, vol. 122, p. 424, 1996 (Abs. No. 258899).

Gordeev et al., "N-α-Fmoc-4-Phosphono(difluoromethyl)-L-phenylalanine . . . into Peptides", Tetrahedron Letters, vol. 35, pp. 7585-7588, 1994.

Kitas et al., "Synthesis of O-Phosphotyrosine . . . Deportection Procedures", J. Org. Chem., vol. 55, pp. 4181-4187, 1990.

Chemical Abstracts, vol. 124, No. 1, p. 1004, 1996 (Abs. No. 9413).

Morelock et al., "Determination of Receptor . . . Phosphotyrosyl Peptides", J. of Med. Chem., vol. 38, pp. 1309-1318.

Shahripour et al., "Novel Phosphotyrosine . . . Domain", Bioorganic & Medicinal Chem. Letters, vol. 6, No. 11, pp. 1209-1214, 1996.

Rojas et al., "An Alternative . . . SH2 Domain", Biochemical and Biophysical Research Communications, vol. 234, pp. 675-680, 1997.

U.S. Appl. No. 09/937,150, filed Mar. 23, 2000, Burke, Jr. et al.

Jiang et al. "Hepatocyte growth factor/scatter factor, its molecular, cellular and clinical implications in cancer", Critical Reviews in Oncology/Hematology, 29:209-248 (1999).

Gao et al., "Macrocyclization in the design of a conformationally constrained Grb2 SHG2 domain inhibitor", Bioorganic & Medicinal Chemistry Letters, 11:1889-1892 (2001).

Gao et al., "Olefin Metathesis in the Design and Synthesis of a Globally constrained Grb2 SH2 Domain Inhibitor", Organic Letters, 3:1617-1620 (2001).

Cornelis, et al., "The Virulence Plasmit of *Yersinia*, an Antihost Genome," vol. 62, No. 4, 1335-1337 (1998).

Zhang et al., "Expression, Purification, and Physicochemical Characterization of a Recombinant *Yersinia* Protein Tyrosine Phosphatase," vol. 267, No. 33, 23759-23766 (1992).

Bliska, et al., "Tyrosine Phosphate Hydrolysis of Host Proteins by an Essential *Yersinia* Virulence Determinant," vol. 88, 1187-1191, 1991.

* cited by examiner

Ii

3a

5b

Ih

Compd 126

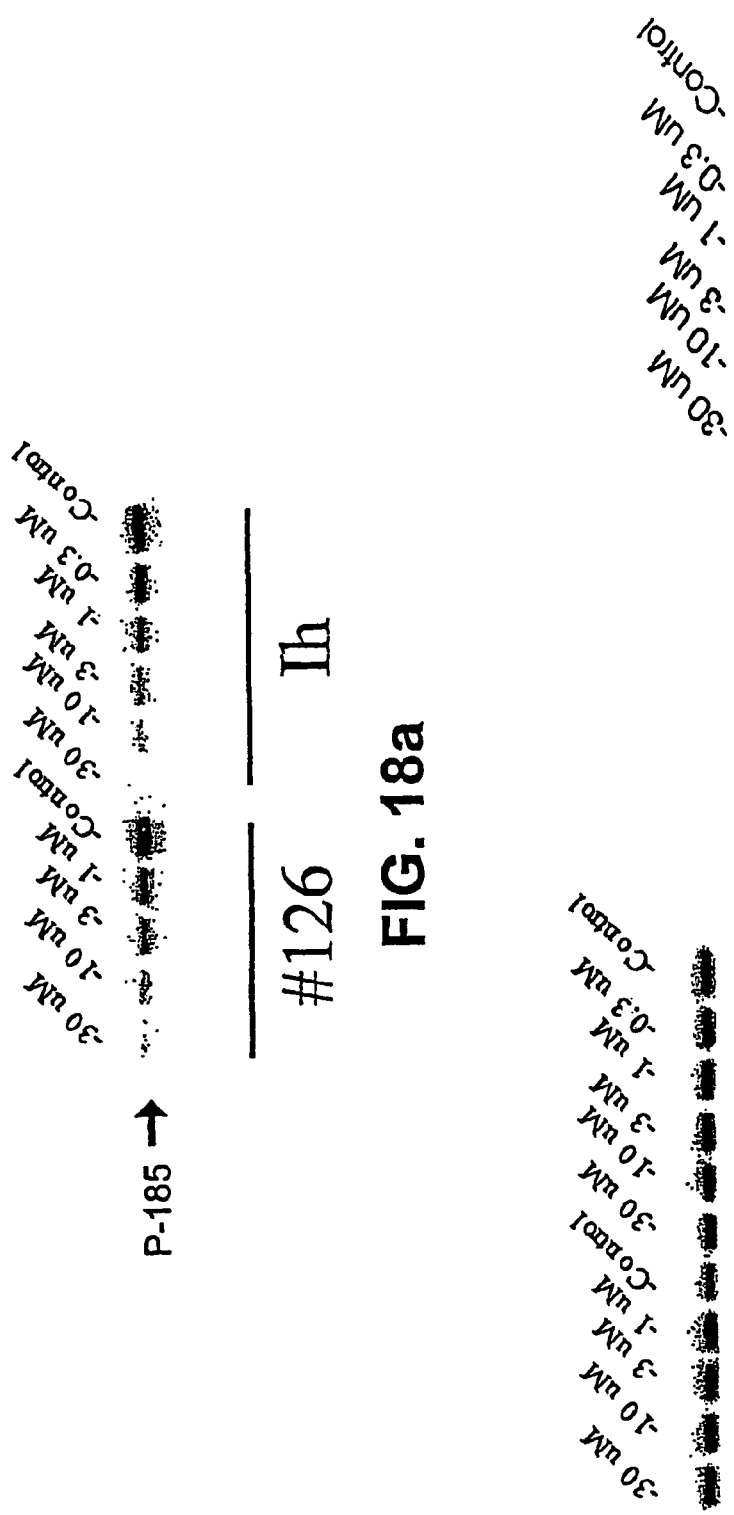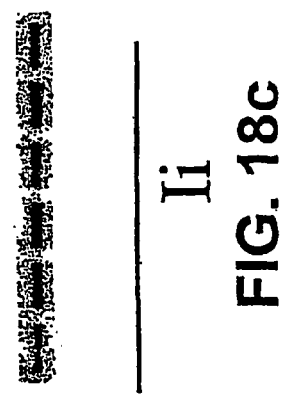
FIG. 18a
FIG. 18b
FIG. 18c

SH2 DOMAIN BINDING INHIBITORS

CROSS-REFERENCE TO RELATED APPLICATIONS

This application is the national phase of PCT/US2003/019987 and claims the benefit of U.S. provisional patent application No. 60/392,028, filed Jun. 28, 2002, the disclosure of which is incorporated by reference. This application also is a continuation-in-part of copending U.S. patent application Ser. No. 10/362,231, filed Feb. 22, 2003, as a national phase of PCT/US01/26078, filed Aug. 22, 2001, published as WO 02/16407, the disclosure of which is incorporated by reference.

TECHNICAL FIELD

This invention relates to novel compounds, e.g., macrocyclic and other peptides, compositions comprising these compounds, and methods of using these compounds, e.g., in inhibiting SH2 domain binding with a phosphoprotein such as in the prevention or treatment of a disease, state, or condition in a mammal. The present invention also relates to a method for preparing these compounds and intermediates useful in their preparation.

BACKGROUND OF THE INVENTION

The pharmaceutical industry is in search for new classes of compounds for the therapy and prophylaxis of proliferative diseases such as cancer, autoimmune diseases, and hyperproliferative skin disorders such as psoriasis. These diseases or disorders affect a large portion of the population, leading to suffering and possibly death.

Some of these diseases or disorders may involve signal transduction. Signal transduction is critical to normal cellular homeostasis and is the process of relaying extracellular messages, e.g., chemical messages in the form of growth factors, hormones and neurotransmitters, via receptors, e.g., cell-surface receptors, to the interior of the cell. Protein-tyrosine kinases play a central role in this biological function. Among others, these enzymes catalyze the phosphorylation of specific tyrosine residues to form tyrosine phosphorylated residues. Examples of this class of enzymes include the PDGF receptor, the FGF receptor, the HGF receptor, members of the EGF receptor family such as the EGF receptor, erb-B2, erb-B3 and erb-B4, the src kinase family, Fak kinase and the Jak kinase family. The tyrosine-phosphorylated proteins are involved in a range of metabolic processes, from proliferation and growth to differentiation.

Protein-tyrosine phosphorylation is known to be involved in modulating the activity of some target enzymes as well as in generating specific complex networks involved in signal transduction via various proteins containing a specific amino acid sequence called a Src homology region or SH2 domain (see Proc. Natl. Acad. Sci. USA, 90, 5891 (1990)). A malfunction in this protein-tyrosine phosphorylation through tyrosine kinase overexpression or deregulation is manifested by various oncogenic and (hyper-)proliferative disorders such as cancer, inflammation, autoimmune disease, hyperroliferative skin disorders, such as psoriasis, and allergy/asthma.

SH2- and/or SH3-comprising proteins that play a role in cellular signaling and transformation include, but are not limited to, the following: Src, Lck, Eps, ras GTPase-activating protein (GAP), phospholipase C, phosphoinositol-3 (P1-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Ab1, Shc, Nck, Crk, CrkL, Syp, Blk, 113TF, 91TF, Tyk2, especially Src, phospholipase c, phoshoinositol-3 (p1-3)kinase, Grb2, BCR-Ab1, Shc, Nck, Crk, CrkL, Syp, Blk, 113TF, 91TF, and Tyk2. A direct link has been established between activated receptor kinases and Ras with the finding that the mammalian Grb2 protein, a 26 kilodalton (kD) protein comprising a single SH2 and two SH3 domains bind to proline-rich sequences present in the Sos exchange factor.

The significance of ras-regulatory proteins in human tumors is also highlighted by the critical role of Grb2 in BCR-Ab1 mediated oncogenesis (J. Exp. Med., 179, 167-175 (1994)).

Central to the binding of SH2 domains with phosphotyrosine ("pTyr") containing ligands is the interaction of the doubly ionized ptyr phosphate with two invariant arginine residues in a well formed pocket. These arginine-phosphate interactions are particularly critical to the overall binding, such that high affinity binding is usually lost by removal of the phosphate group.

U.S. provisional patent application Nos. 60/160,899, filed Oct. 22, 1999; and 60/221,525, filed Jul. 28, 2000; and International Publication Nos. WO 02/16407, WO 00/73326 A2 and WO 00/56760 disclose certain SH2 domain binding inhibitors, the disclosures of which are incorporated herein in their entireties by reference.

There exists a need for molecules that have an ability to mimic the structure of the phosphotyrosine peptide binding site, as well as a need for compounds that have the ability to disrupt the interaction between SH2 domains of proteins (e.g., regulatory proteins) for example that of Grb2, and proteins with phosphorylated moieties. There also exists a need for suitable starting materials, intermediates, or precursors in the synthesis of the molecules that inhibit binding of SH2 domains. There further exists a need for compounds suitable for use in the therapy or prophylaxis of proliferative diseases or conditions, as well as in diagnosis, assays, and testing.

These and other advantages of the present invention will be apparent from the description as set forth below.

SUMMARY OF THE INVENTION

The present invention provides a number of SH2 domain inhibiting compounds. e.g., peptides, preferably, macrocyclic peptides. Thus, the present invention provides a compound of formula (I)

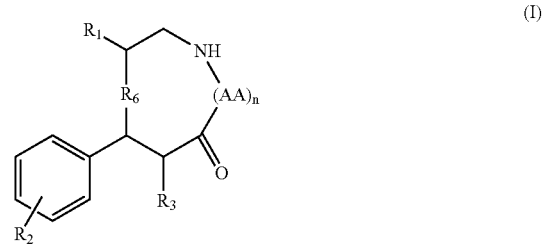

wherein $R_1$ is a lipophile; $R_2$ in combination with the phenyl ring is a phenylphosphate mimic group or a protected phenylphosphate mimic group; $R_3$ is hydrogen, azido, amino, carboxyalkyl, alkoxycarbonylalkyl, aminocarbonylalkyl, or alkylcarbonylamino, wherein the alkyl portion of $R_3$ may be optionally substituted with a substituent selected from the group consisting of halo, hydroxy, carboxyl, amino, aminoalkyl, alkyl, alkoxy, and keto; $R_6$ is a linker; AA is an amino acid; and n is 1 to 6; or a salt thereof. The compounds of the present invention, in embodiments, have the advantage that their conformation is constrained to provide enhanced binding affinity with SH2 domain protein.

The present invention further provides a pharmaceutical composition comprising a pharmaceutically or pharmacologically acceptable carrier and a compound of the present invention. The present invention also provides a method for inhibiting an SH2 domain from binding with a phosphoprotein comprising contacting an SH2 domain with a compound of the present invention. The present invention also provides a method of preventing or treating a disease, state, or condition by the use of one or more of these compounds. The present invention also provides a method for preparing the compounds of the present invention. The present invention further provides intermediates useful in the preparation of the compounds.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

BRIEF DESCRIPTION OF THE DRAWINGS

FIGS. 18a-c depict the effect of inhibitors on the binding of Grb2 to erbB-2 tyrosine kinase in whole cell assays (IP: Grb2 c-23 WB: pTy (PY99)). FIG. 18a depicts the effect of compounds Ih and 126 on erbB-2 and Grb2 association in MDA453 cells; FIG. 18b depicts the effect of compounds 3a and 5b on erbB-2 and Grb2 association in MDA453 cells; and FIG. 18c depicts the effect of compound Ii on erbB-2 and Grb2 association in MDA453 cells.

FIG. 25 depicts the whole cell (intracellular) assay of GrB2 binding to p185erbB-2.

SPECIFIC DESCRIPTION OF THE INVENTION

Figure 1:
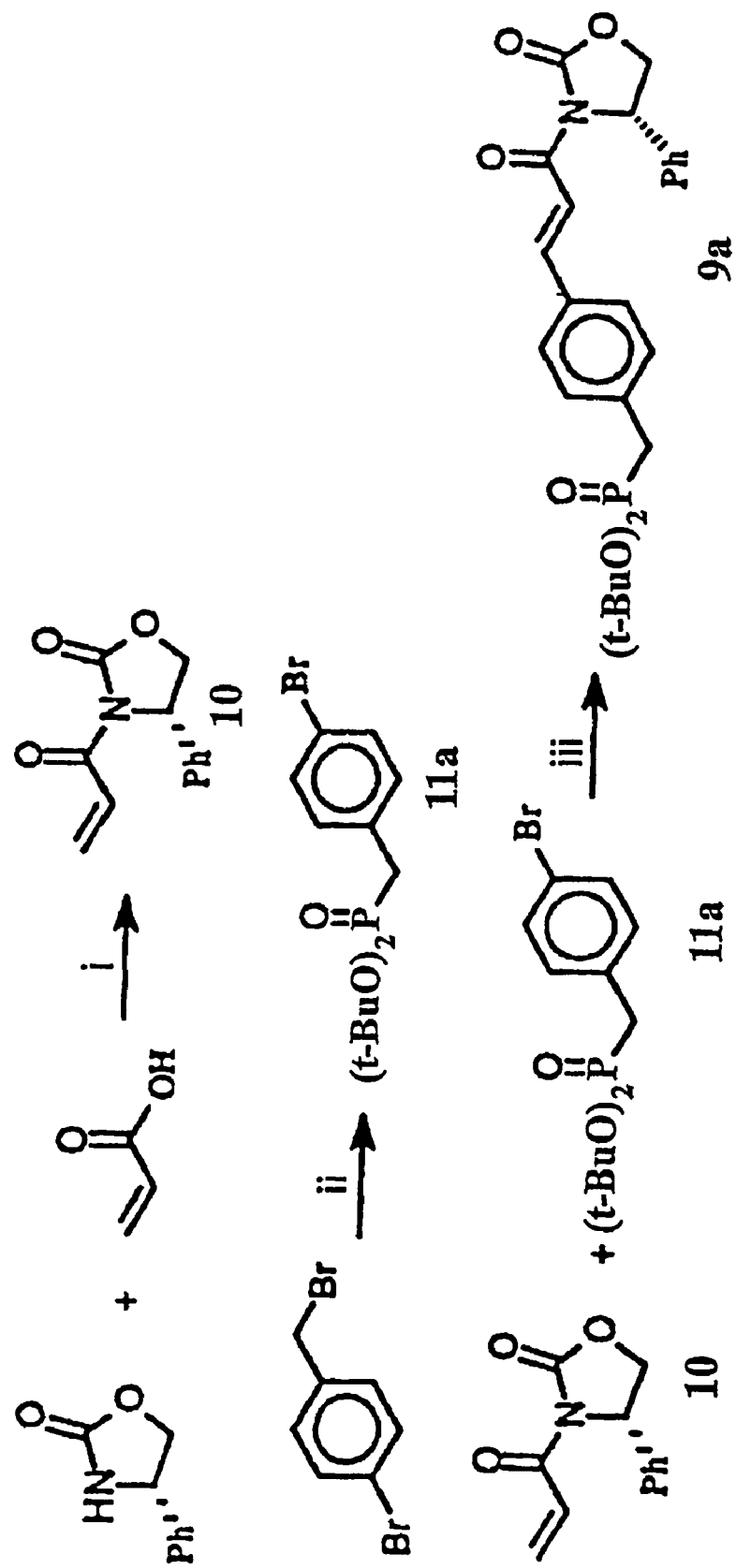
FIG. 1 depicts a method of preparing compound 9a in accordance with an embodiment of the present invention. i. pivaloyl chloride, Et$_3$N, BuLi, −78° C.~R.T., 81%; ii. t-butyl phosphite, BuLi, 0° C.~R.T., 90%; iii. Et$_3$N, Pd(OAc)$_2$, tri-o-tolylphosphine, reflux, 85.5%.
Figure 2:
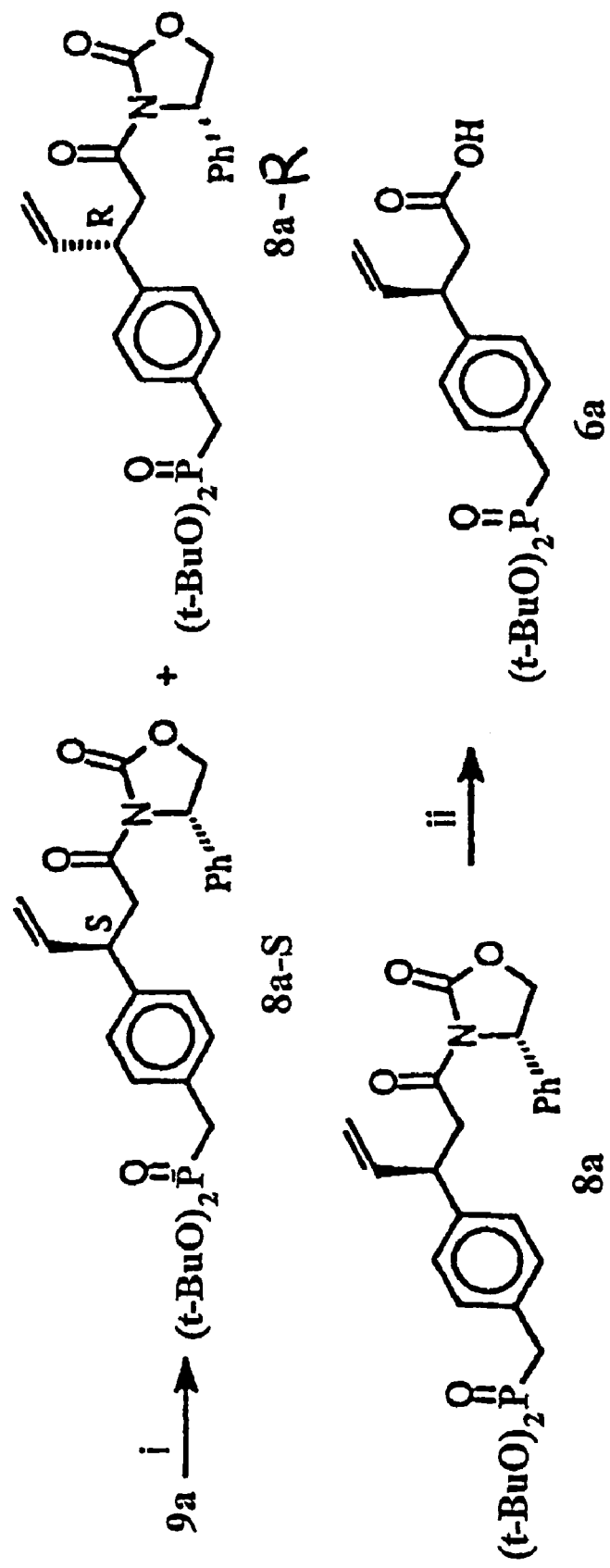
FIG. 2 depicts a method of preparing compound 6a in accordance with an embodiment of the present invention. i. vinyl magnesium bromide, PhSCu, Et$_2$O-THF, −40° C., 67%, 64% d.e.; ii H$_2$O$_2$, 2 eq. LiOH, THF-H$_2$O, 81%.
Figure 3:
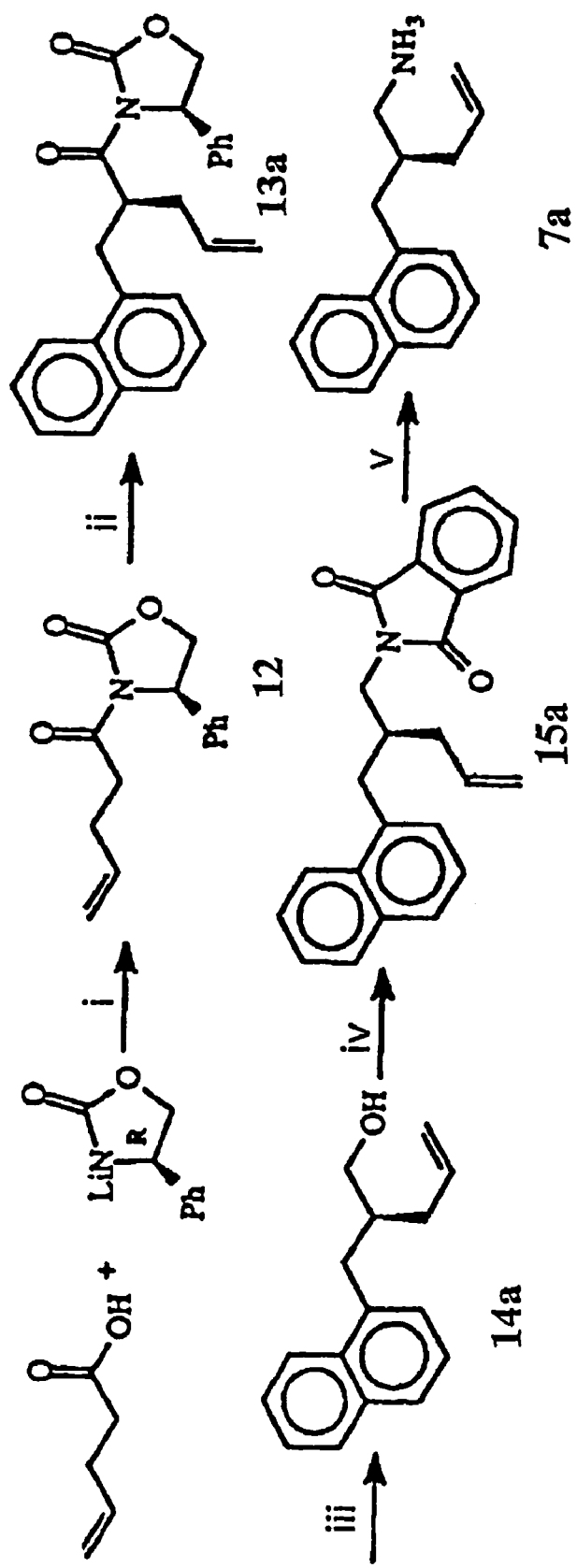
FIG. 3 depicts a method of preparing compound 7a in accordance with an embodiment of the present invention. i. Trimethylacetyl chloride, NMP, 70%, ii. a) LiHMDS, THF; b) 1-bromomethyl-naphthalene, 88%; iii. LiAlH$_4$, THF, −78° C.-R.T., 100%; iv. DEAD, PPh$_3$, Phthalimide, THF, 73%; v. EtOH, H$_2$O, N$_2$H$_4$.H$_2$O, 91%.
Figure 4:
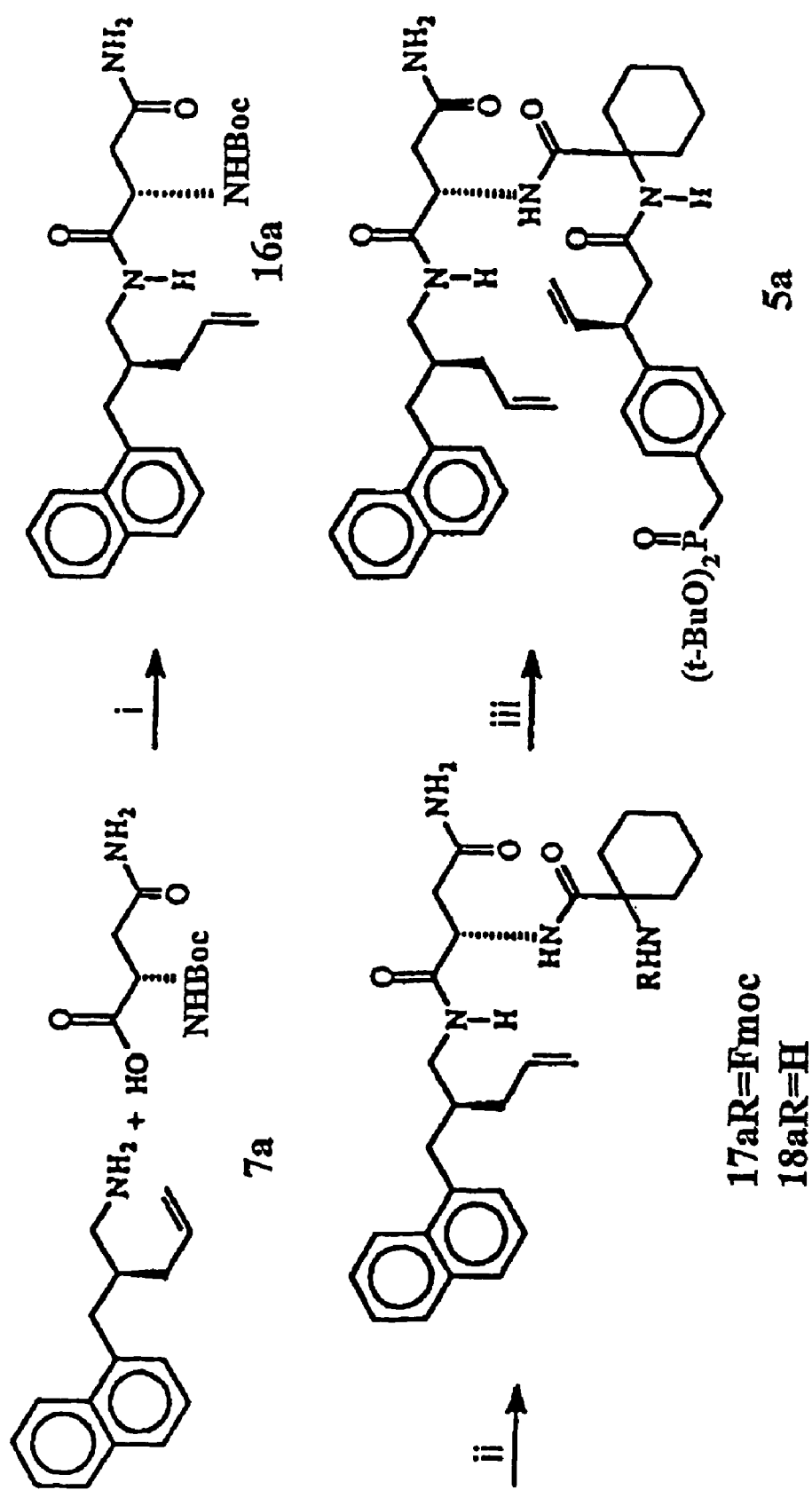
FIG. 4 depicts a method of preparing compound 5a in accordance with an embodiment of the present invention. i. HOBt, DIPCDI, 95%; ii. a) TFA-CH$_2$Cl$_2$; b) NHCO$_3$; c) Fmoc-1-amino-cyclohexane carboxylic acid, HOBt, DIPCDI; 70%; d) TFA-CH$_2$Cl$_2$; e) NaHCO$_3$, 98%; iii. 6a, HOBt, DIPCDI, 67%.
Figure 5:
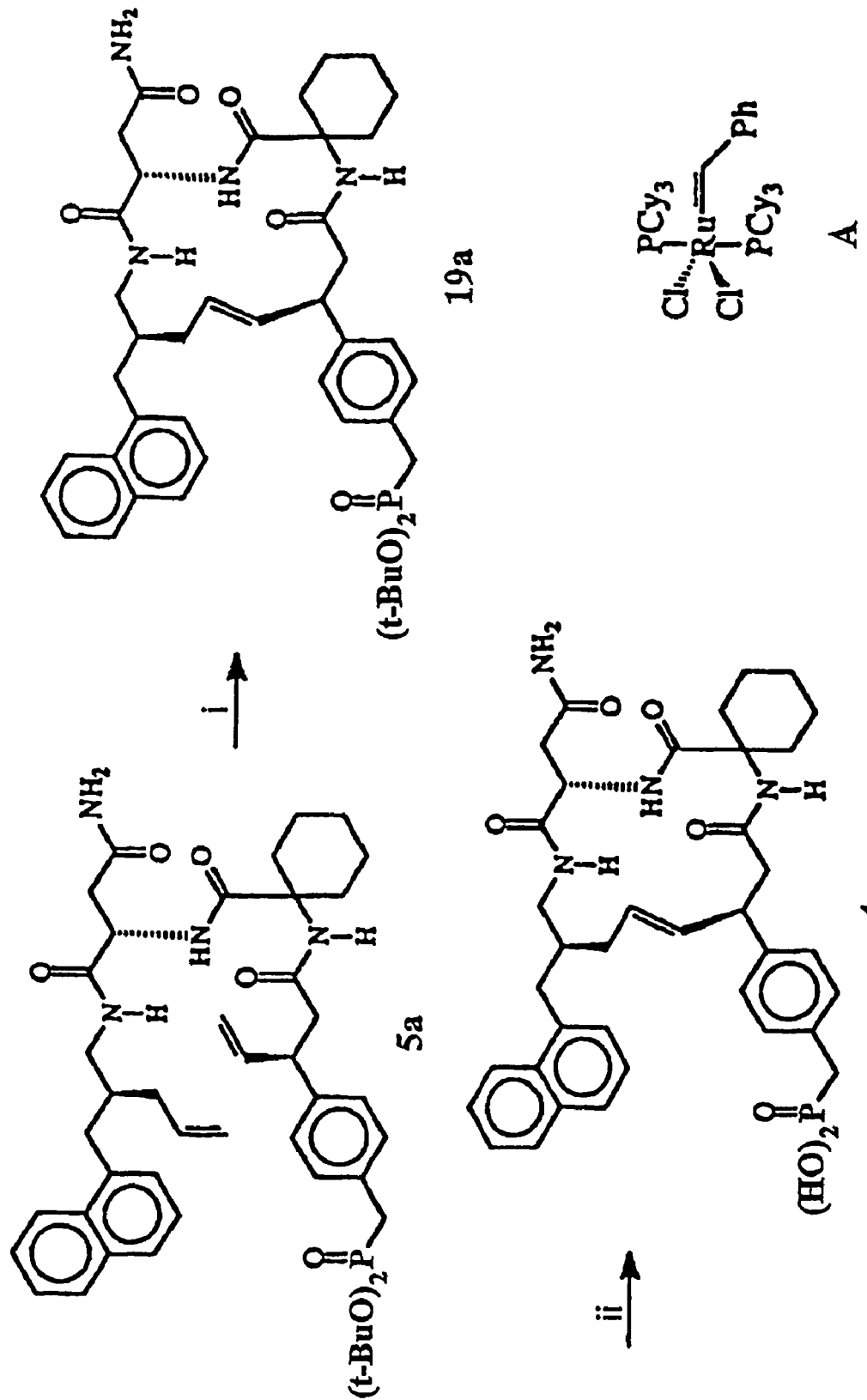
FIG. 5 depicts a method of preparing compound 4a in accordance with an embodiment of the present invention. i. Grubbs Catalyst, CH$_2$Cl$_2$, reflux, 60 hr, 67%; ii. TFA-H$_2$O-Trimethylsilane, 1 hr; A: Grubbs Catalyst.
Figure 6:
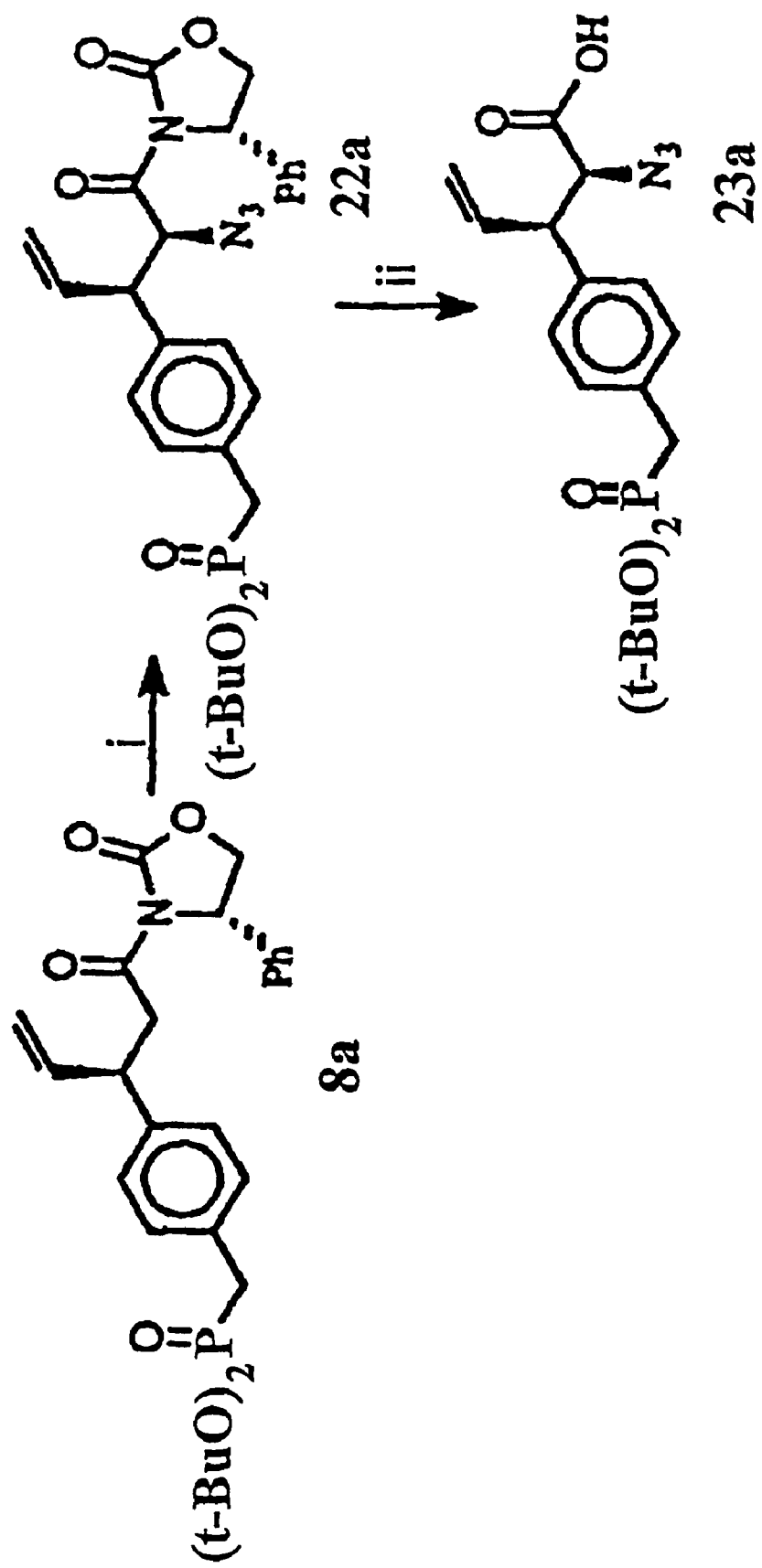
FIG. 6 depicts a method of preparing compound 23a in accordance with an embodiment of the present invention. i. 1) NaHMDS, −70° C., 2) Trisyl azide, 73%; ii. H$_2$O$_2$, 2 eq. LiOH, THF-H$_2$O, 92%.
Figure 7:
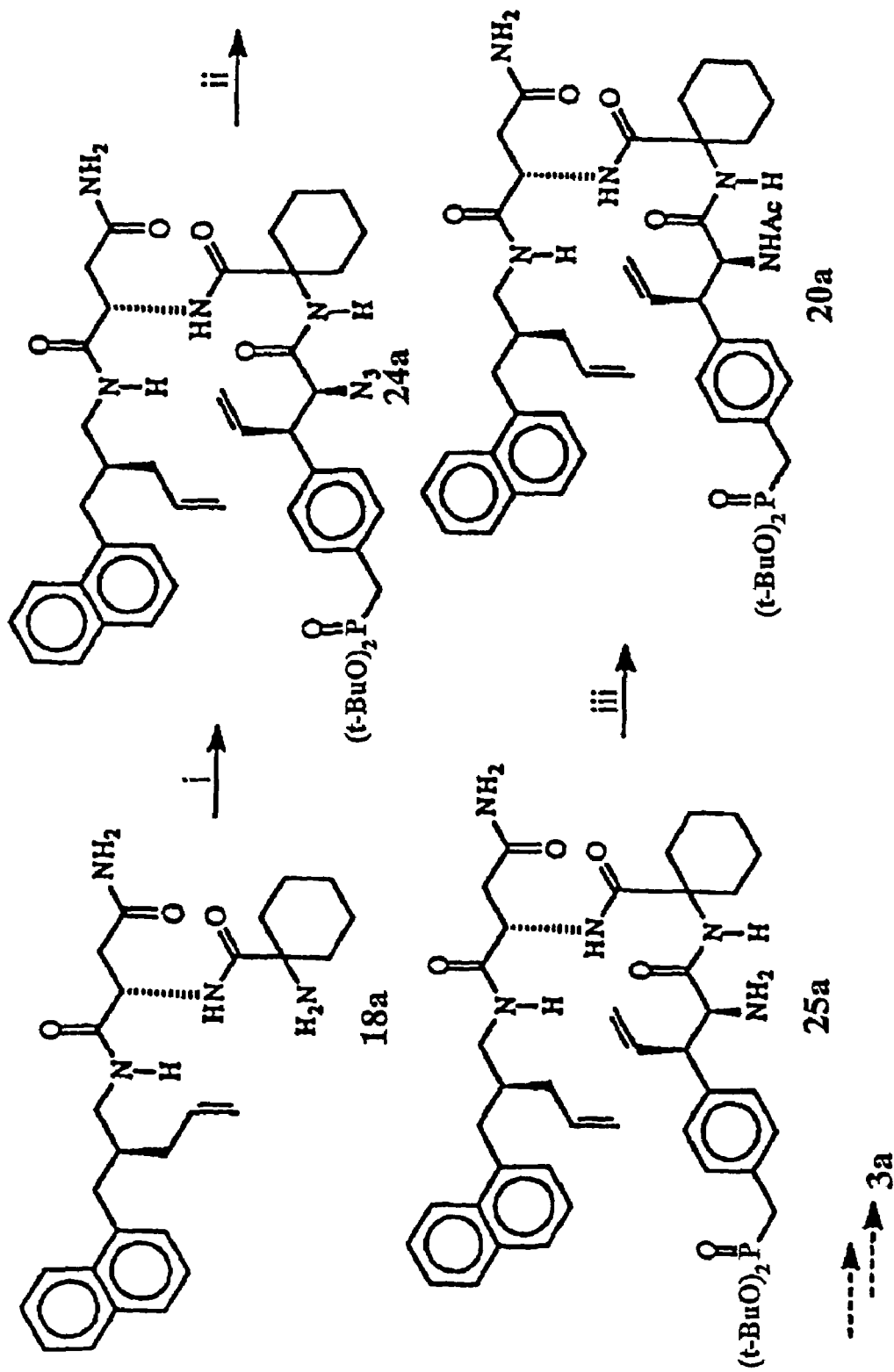
FIG. 7 depicts a method of preparing compound 3a in accordance with an embodiment of the present invention. i. 23a HOBt, DIPCDI, 67%; ii. PPh$_3$, THF-H$_2$O, 77%; iii. Ac$_2$O, Pyridine.
Figure 8:
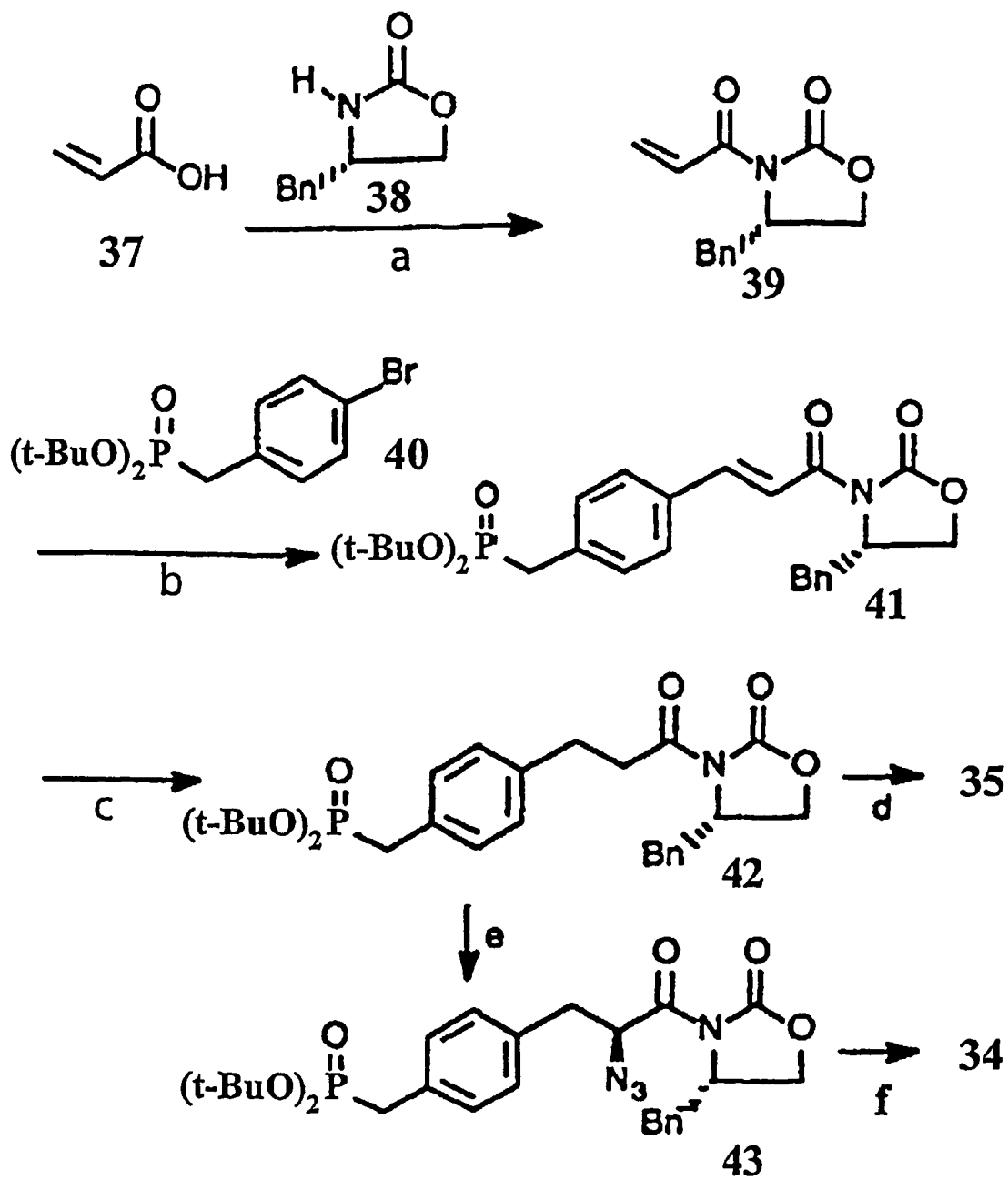
FIG. 8 depicts a method of preparing compounds 34-35 in accordance with an embodiment of the present invention. (a) (1) pivaloyl chloride, N-methylmorpholine, −78° C.; (2) lithium salt of 38 (49%); (b) Pd(OAC)$_2$, P(o-toluyl)$_3$, NEt$_3$, 85° C. (79)%; (c) H$_2$/Pd$^0$ (82%); (d) LiOH, H$_2$O$_2$, THF/H$_2$O, 0° C. (81%); (e) KHMDS, trisyl azide (77%); (f) LiOH, H$_2$O$_2$, THF/H$_2$O, 0° C. (88%).
Figure 9:
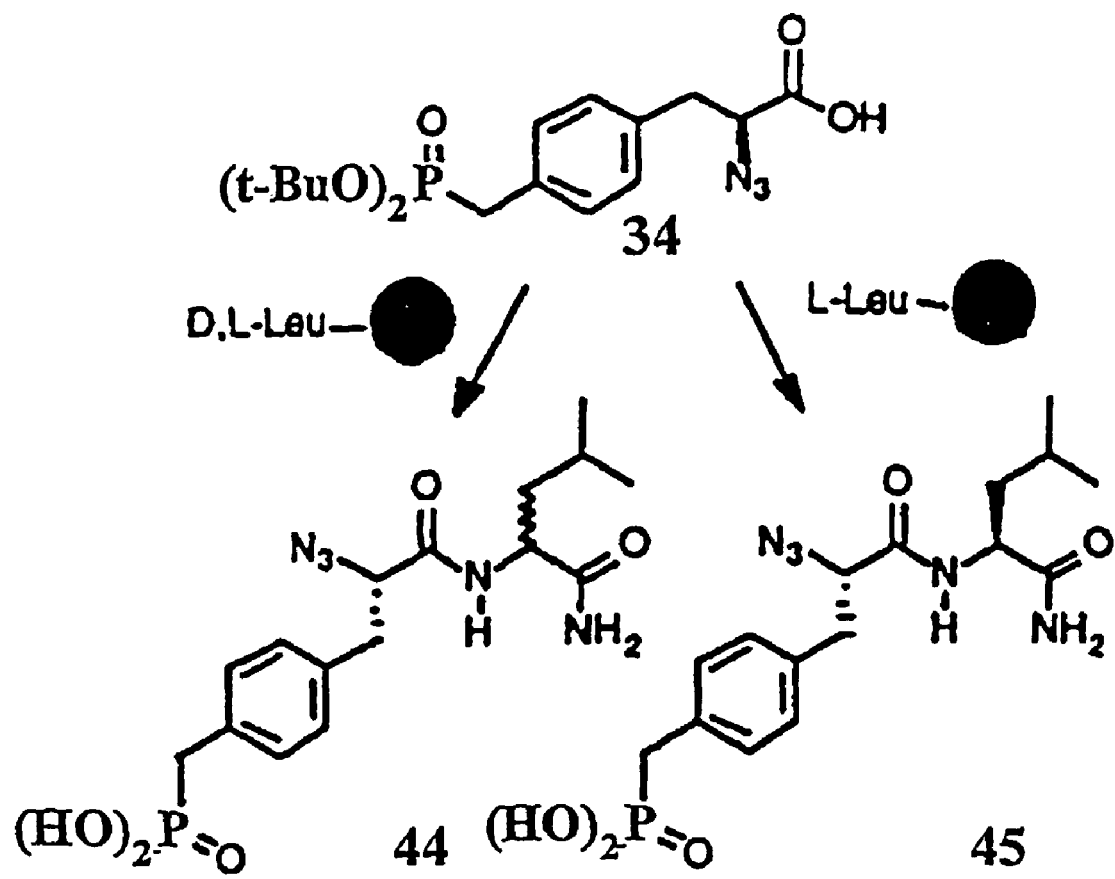
FIG. 9 depicts a method of preparing compounds 44-45 in accordance with an embodiment of the present invention.

An aspect of the present invention is predicated on the concept that binding affinity for SH2 domain proteins can be envisioned to increase by a conformational constraint in a ligand. The conformational constraint is believed to lead to certain advantages, e.g., a reduction in binding entropy penalty. Binding of natural pTyr-containing ligands to Grb2 SH2 domains takes place in a β-bend fashion, with key interactions occurring in a pTyr binding pocket as well as in a proximal pocket which ligates the amino acid side chain of a pY+2 Asn residue. The present invention provides a novel platform which is expected provide enhanced binding outside the pTyr pocket.

In accordance with an embodiment, the present invention provides certain compounds, e.g., macrocyclic peptides. The present invention provides a compound of formula (I)

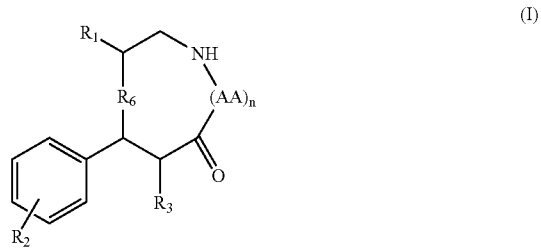

wherein $R_1$ is a lipophile; $R_2$, in combination with the phenyl ring, is a phenylphosphate mimic group or a protected phenylphosphate mimic group; $R_3$ is hydrogen, azido, amino, carboxyalkyl, alkoxycarbonylalkyl, aminocarbonylalkyl, or alkylcarbonylamino, wherein the alkyl portion of $R_3$ may be optionally substituted with a substituent selected from the group consisting of halo, hydroxy, carboxyl, amino, aminoalkyl, alkyl, alkoxy, and keto; $R_6$ is a linker; AA is an amino acid; and n is 1 to 6; or a salt thereof.

$R_1$ can be any suitable lipophile, e.g., a lipophilic group that is capable of providing or enhancing cell membrane penetration. Examples of lipophiles include aralkyl, arylheterocyclylalkyl, alkylaminocarbonyl, alkenylaminocarbonyl, arylaminoacrabonyl, alkoxyalkyl, aryloxyalkyl, or aralkoxyalkyl groups, wherein the aryl portion is optionally substituted a substituent selected from the group consisting of halo, hydroxy, carboxyl, amino, amido, aminoalkyl, alkyl, alkoxy, and keto. In embodiments, the aryl portion is phenyl or naphthyl and the alkyl portion is a $C_1$-$C_6$ alkyl, and the heterocyclyl is a 3-7 membered ring having one or more of N, O, or S. In a preferred embodiment, the heterocyclyl is a 5-membered ring, and in a further preferred embodiment, the heterocyclyl is a 5-membered ring containing N. In a preferred embodiment, the alkyl portion of the arylheterocyclylalkyl is a $C_2$-$C_3$ alkyl. Examples of suitable arylheterocyclylalkyls include indolylmethyl and naphthylmethyl, e.g., naphthyl-2-methyl.

$R_2$ can be any suitable phenylphosphate mimic group or a protected phenylphosphate mimic group. Examples of $R_2$ include hydroxyl, carboxyl, formyl, carboxyalkyl, carboxyalkoxy, dicarboxyalkyl, dicarboxyalkyloxy, dicarboxyhaloalkyl, dicarboxyhaloalkyloxy, phosphono, phosphonoalkyl, phosphonohaloalkyl, phosphoryl, phosphorylalkyl, or phosphorylalkoxy, wherein the alkyl portion may be optionally substituted with a substituent selected from the group consisting of halo, hydroxy, carboxyl, amino, amido, aminoalkyl, alkyl, alkoxy, and keto. Examples of the phenylphosphate mimic group include phosphonomethyl, phosphono-(α-fluoro)methyl, phosphono-(α,α-difluoro)methyl, phosphono-(α-hydroxy)methyl, O-sulfo, and dicarboxymethoxy. $R_2$ can be located at the o, p, or meta position, and preferably at the para position on the phenyl ring. The phenylphosphate mimic group can be present as protected groups, e.g., protected as an ester, amide, or ether, of an alcohol such as $C_1$-$C_6$ alcohol, preferably t-butyl alcohol.

In accordance with embodiments, $R_3$ is hydrogen, azido, amino, carboxyalkyl, alkoxycarbonylalkyl, aminocarbonylalkyl, oxalylamino, or alkylcarbonylamino; wherein the alkyl portion of $R_3$ is $C_1$-$C_6$ alkyl which may be optionally substituted with a substituent selected from the group consisting of halo, hydroxy, carboxyl, amino, amido, aminoalkyl, alkyl, alkoxy, and keto. In a preferred embodiment, $R_3$ is carboxyalkyl, alkoxycarbonylalkyl, aminocarbonylalkyl, or alkylcarbonylamino, and wherein the alkyl is methyl.

Any suitable, natural or synthetic or modified amino acid can be employed. Examples of amino acids include glycine, alanine, valine, norvaline, leucine, iso-leucine, norleucine, α-amino n-decanoic acid, serine, homoserine, threonine, methionine, cysteine, S-acetylaminomethyl-cysteine, proline, trans-3- and trans-4-hydroxyproline, phenylalanine, tyrosine, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid mono amide, glutamic acid, glutamine, histidine, arginine, lysine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid and α,β-diaminopropionic acid, homophenylalanine, and α-tert-butylglycine. Preferred examples include, α-aminocyclohexane carboxylic acid and asparagine.

The linker can be any suitable moiety that conformationally constrains the compound of the present invention, e.g., in the beta bend fashion. The linker is not limited by any chemical structure. The linker can be linear or branched, substituted or unsubstituted, group, e.g., a group having 1-6 carbon atoms, optionally with one or more N, O, or S. Examples of suitable linkers include alkylenyl, alkenylenyl, and alkynylenyl, preferably ethylenyl, ethenylenyl, or ethynylenyl. The points of attachment of the linker can have a suitable configuration, e.g., in R, S, or a mixture of R and S forms.

In preferred embodiments of the compounds of the present invention, n is 2-4, and in further preferred embodiments, n is 2 or 3.

In a preferred embodiment, the present invention provides a compound of formula (Ia)

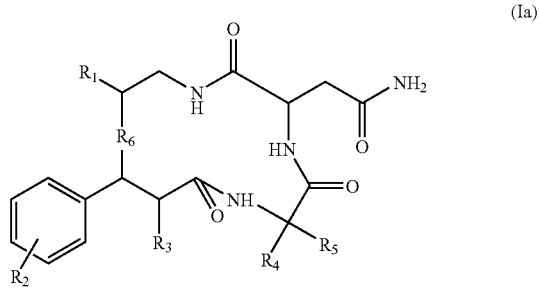

(Ia)

wherein $R_4$ and $R_5$, independently, are hydrogen, alkyl, cycloalkyl, or heterocyclyl, or $R_4$ and $R_5$ together form a cycloalkyl or heterocyclyl.

In another preferred embodiment, the present invention provides a compound of the formula (Ib):

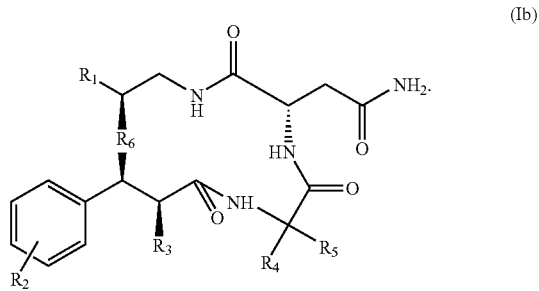

(Ib)

In accordance with embodiments of the present invention, in the compounds described above, $R_1$ is aralkyl, arylheterocyclylalkyl, alkylaminocarbonyl, alkenylaminocarbonyl, arylaminoacrabonyl, alkoxyalkyl, aryloxyalkyl, or aralkoxyalkyl, wherein the aryl portion is phenyl or naphthyl and the alkyl portion is a $C_1$-$C_6$ alkyl, and the heterocyclyl is a 3-7 membered ring having at least one of N, O, or S;

$R_2$ is hydroxyl, carboxyl, formyl, carboxyalkyl, carboxyalkoxy, dicarboxyalkyl, dicarboxyalkyloxy, dicarboxyhaloalkyl, dicarboxyhaloalkyloxy, phosphono, phosphonoalkyl, phosphonohaloalkyl, phosphoryl, phosphorylalkyl, or phosphorylalkoxy, wherein the alkyl or alkoxy portion of $R_2$ is a $C_1$-$C_6$ alkyl or alkoxy and may be optionally substituted with a substituent selected from the group consisting of halo, hydroxy, carboxyl, amino, aminoalkyl, alkyl, alkoxy, and keto;

$R_3$ is hydrogen, azido, amino, carboxyalkyl, alkoxycarbonylalkyl, aminocarbonylalkyl, or alkylcarbonylamino; wherein the alkyl portion of $R_3$ is $C_1$-$C_6$ alkyl which may be optionally substituted with a substituent selected from the group consisting of halo, hydroxy, carboxyl, amino, aminoalkyl, alkyl, alkoxy, and keto;

$R_4$ and $R_5$, independently, are hydrogen, alkyl, cycloalkyl, heterocyclyl, or together form cycloalkyl or heterocyclyl, wherein the alkyl is a $C_1$-$C_6$ alkyl, the cycloalkyl is a $C_3$-$C_7$ cycloalkyl, and the heterocyclyl is a 3-7 membered ring with one or more of N, O, or S; and $R_6$ is a $C_2$-$C_4$ alkylenyl or alkenylenyl group, which may be optionally substituted with a substituent selected from the group consisting of halo, hydroxy, carboxyl, amino, aminoalkyl, alkyl, alkoxy, and keto.

In particular embodiments, $R_1$ is naphthylmethyl or indolyl and $R_2$ is carboxyalkyl, carboxyalkoxy, dicarboxyalkyl, dicarboxyalkoxy, dicarboxyhaloalkyl, dicarboxyhaloalkoxy, phosphonoalkyl, phosphonohaloalkyl, phosphoryl, phosphorylalkyl, or phosphorylalkoxy, wherein the alkyl or alkoxy portion of $R_2$ is a $C_1$-$C_6$ alkyl or alkoxy and may be optionally substituted with a substituent selected from the group consisting of halo, hydroxy, carboxyl, amino, aminoalkyl, alkyl, alkoxy, and keto.

In certain embodiments, $R_1$ is naphthylmethyl or indolyl and $R_2$ is carboxyalkoxy, dicarboxyalkyl, dicarboxyalkoxy, dicarboxyhaloalkyl, dicarboxyhaloalkoxy, phosphonoalkyl, phosphonohaloalkyl, phosphoryl, phosphorylalkyl, or phosphorylalkoxy, wherein the alkyl or alkoxy portion of $R_2$ is a $C_1$-$C_6$ alkyl or alkoxy and may be optionally substituted with a substituent selected from the group consisting of halo, hydroxy, carboxyl, amino, aminoalkyl, alkyl, alkoxy, and keto. In certain preferred embodiments, $R_2$ is phosphono, phosphonoalkyl, phosphonohaloalkyl, phosphonodihaloalkyl, or phosphoryl, e.g., phosphonomethyl, phosphonohalomethyl, or phosphonodihalomethyl.

In embodiments, the present invention provides compounds described above wherein $R_3$ is carboxy $C_1$-$C_6$ alkyl, e.g., carboxymethyl or dicarboxy $C_1$-$C_6$ alkyl, e.g., dicarboxymethyl.

In certain embodiments described above, $R_3$ is alkoxycarbonyl $C_1$-$C_6$ alkyl, aminocarbonyl $C_1$-$C_6$ alkyl, oxalylamino, or $C_1$-$C_6$ alkylcarbonylamino; wherein the alkyl portion of $R_3$ may be optionally substituted with a substituent selected from the group consisting of halo, hydroxy, carboxyl, amino, aminoalkyl, alkyl, alkoxy, and keto. In certain preferred embodiments, $R_3$ is $C_1$-$C_6$ alkylcarbonylamino, e.g., acetylamino.

In certain embodiments described above, $R_4$ and $R_5$, independently, are hydrogen, alkyl, or together form cycloalkyl, wherein the alkyl is a $C_1$-$C_6$ alkyl, and the cycloalkyl is a $C_3$-$C_7$ cycloalkyl, e.g., a $C_6$ cycloalkyl.

In an embodiment, $R_1$ is napthylmethyl, $R_2$ is dicarboxyalkyl (e.g., malonyl), $R_3$ is carboxyalkyl (e.g., carboxymethyl), $R_4$ and $R_5$ together form cycloalkyl (e.g., cyclohexyl), and $R_6$ is a $C_2$-$C_4$ alkylenyl group (e.g., $C_3$ alkenylenyl).

In accordance with embodiments of the present invention, the present invention provides a compound of formula (Ic):

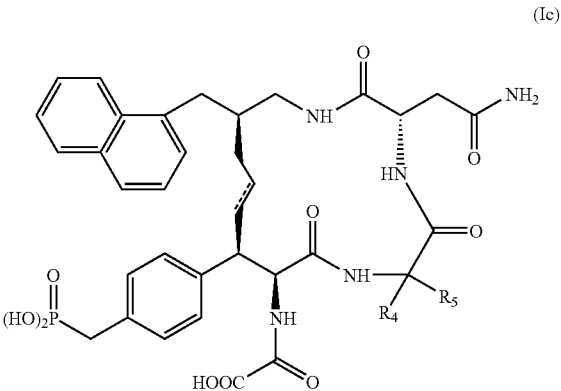

(Ic)

wherein $R_4$ and $R_5$ are independently $C_1$-$C_6$ alkyl or hydrogen; a compound of formula (Id)

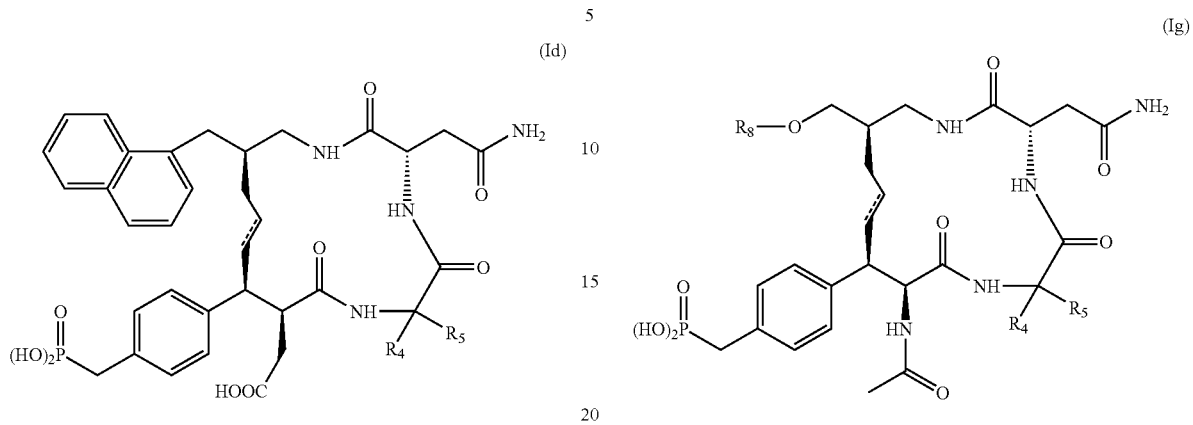

(Id)

wherein $R_4$ and $R_5$ are independently $C_1$-$C_6$ alkyl or hydrogen or $R_4$ and $R_5$ together form a cycloalkyl, e.g., cyclohexyl, a compound of the formula (Ie)

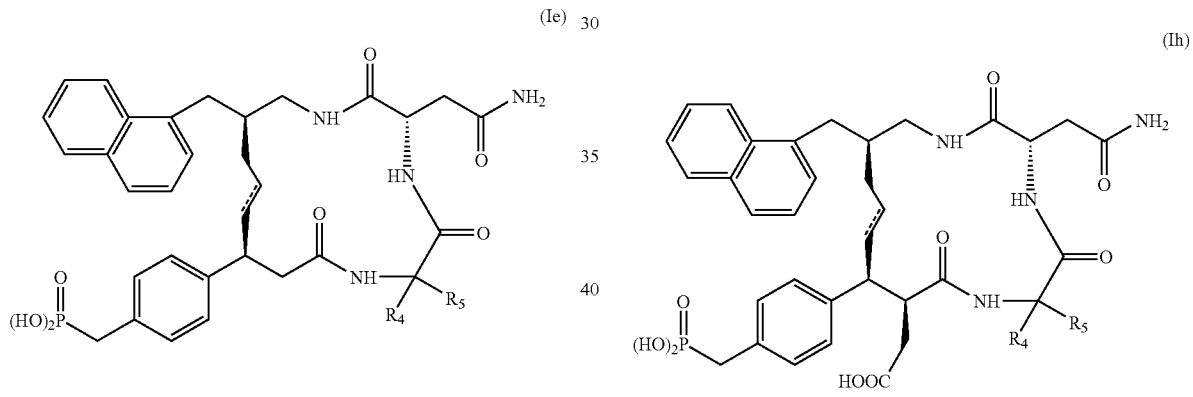

(Ie)

wherein $R_4$ and $R_5$ together form cyclohexyl; a compound of the formula (If):

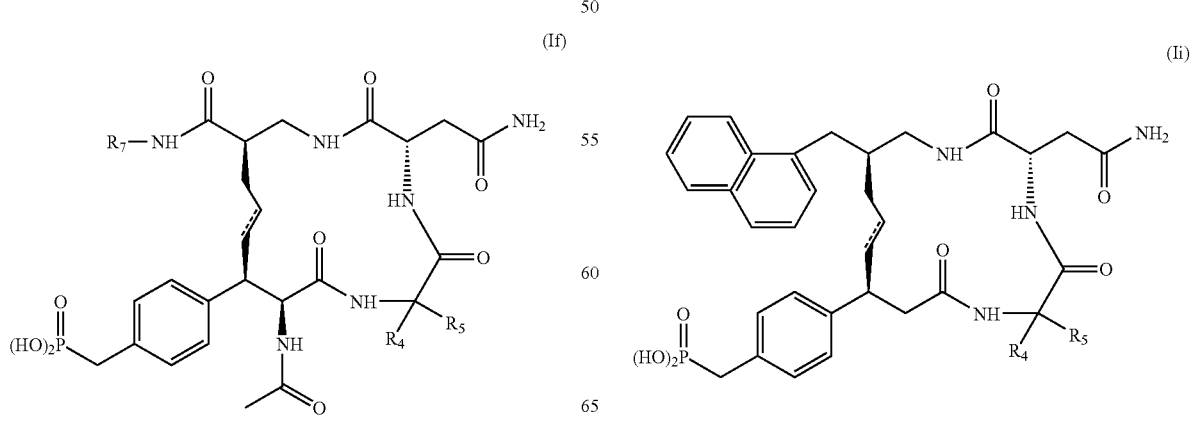

(If)

wherein $R_7$ is aryl or alkenyl, and $R_4$ and $R_5$ are independently $C_1$-$C_6$ alkyl or hydrogen; and a compound of the formula (Ig)

(Ig)

wherein $R_5$ is aryl alkyl and $R_4$ and $R_5$ are independently $C_1$-$C_6$ alkyl or hydrogen. In a preferred embodiment of the compound of formula (Ig), R is benzyl or naphthylmethyl.

In a preferred embodiment, the present invention provides a compound of formula (Ih):

(Ih)

wherein $R_4$ and $R_5$ are methyl.

In another embodiment, the present invention provides a compound of formula (Ii):

(Ii)

wherein $R_4$ and $R_5$ are methyl.

In a further embodiment, the present invention provides compound 233:

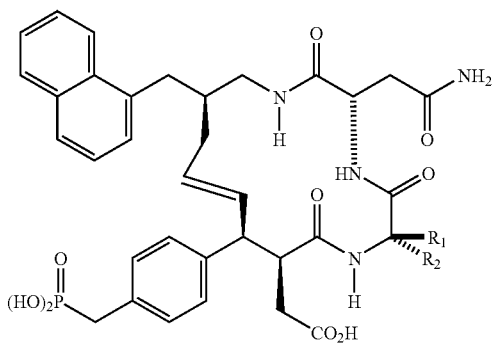

233 R$_1$, R$_2$ together=cyclohexyl.

In another embodiment, the present invention provides compound 313:

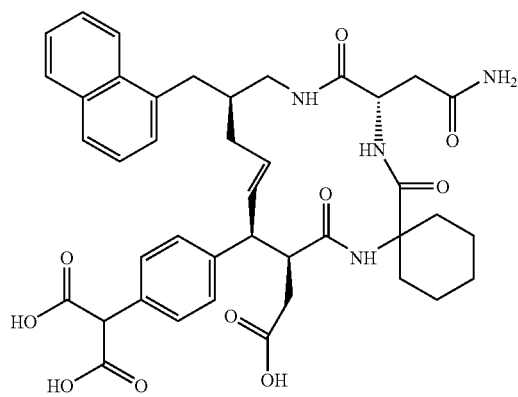

In another aspect, the present invention provides a compound of the formula:

$$W\text{—}Y'\text{-}(AA)_n\text{-}Z \qquad (II)$$

wherein n is 0 to 15; Y' is a phenylalanyl radical having a phenyl ring, an amine end, and a carboxyl end, the phenyl ring having one or more substituents selected from the group consisting of hydroxyl, carboxyl, formyl, carboxyalkyl, carboxyalkyloxy, dicamboxyalkyl, dicarboxyalkyloxy, dicarboxyhaloalkyl, dicarboxyhaloalkyloxy, and phosphonoalkyl, phosphonohaloalkyl, wherein the alkyl portion of the substituents may be unsubstituted or substituted with a substituent selected from the group consisting of halo, hydroxy, carboxyl, amino, aminoalkyl, alkyl, alkoxy, and keto and the amine end includes an azido group; W is a moiety attached to the nitrogen of Y' and is selected from the group consisting of alkylcarbonyl, oxalyl, alkylaminooxalyl, arylaminooxalyl, arylalkylaminooxalyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of W contains at least 4 hetero atoms selected from the group consisting of O, N, and S; AA is an amino acid, the amine end of which is attached to the carboxyl end of Y'; and Z is an arylalkylamino or arylheterocyclyl alkylamino; or a salt thereof.

The alkyl portion of the various groups described for the compound of formula (II) can have any suitable number of carbon atoms, e.g., from 1 to about 12 carbon atoms, preferably from 1 to 6 carbon atoms, and more preferably from 1 to 4 carbon atoms. The aryl portion of the various groups described can have any number of aromatic rings, e.g., from 1 to 3 rings, e.g., six membered rings, preferably 1 or 2 rings, and more preferably 1 ring. Thus, for example, the present invention provides a compound wherein Y' is a phenylalanyl radical having a phenyl ring, an amine end, and a carboxyl end, the phenyl ring having one or more substituents selected from the group consisting of hydroxyl, carboxyl, formyl, carboxy C$_1$-C$_6$ alkyl, carboxy C$_1$-C$_6$ alkyloxy, dicarboxy C$_1$-C$_6$ alkyl, dicarboxy C$_1$-C$_6$ alkyloxy, dicarboxyhalo C$_1$-C$_6$ alkyl, dicarboxyhalo C$_1$-C$_6$ alkyloxy, and phosphono C$_1$-C$_6$ alkyl, phosphonohalo C$_1$-C$_6$ alkyl, wherein the alkyl portion of the substituents may be unsubstituted or substituted with a substituent selected from the group consisting of halo, hydroxy, carboxyl, amino, amino C$_1$-C$_6$ alkyl, C$_1$-C$_6$ alkyl, C$_1$-C$_6$ alkoxy, and keto;

W is a moiety attached to the nitrogen of Y' and is selected from the group consisting of C$_1$-C$_6$ alkylcarbonyl, oxalyl, C$_1$-C$_6$ alkylaminooxalyl, arylaminooxalyl, aryl C$_1$-C$_6$ alkylaminooxalyl, C$_1$-C$_6$ alkoxyoxalyl, carboxy C$_1$-C$_6$ alkyl carbonyl, heterocyclyl carbonyl, heterocyclyl C$_1$-C$_6$ alkyl carbonyl, aryl C$_1$-C$_6$ alkyl heterocyclyl C$_1$-C$_6$ alkyl carbonyl, aryloxycarbonyl, and aryl C$_1$-C$_6$ alkoxycarbonyl, wherein the aryl and alkyl portions of the substituents may be unsubstituted or substituted with a substituent selected from the group consisting of halo, hydroxy, carboxyl, amino, amino C$_1$-C$_6$ alkyl, C$_1$-C$_6$ alkyl, C$_1$-C$_6$ alkoxy, and keto; and the heterocyclyl portion of W contains at least 4 hetero atoms selected from the group consisting of O, N, and S; AA is an amino acid, the amine end of which is attached to the carboxyl end of Y'; and Z is an aryl C$_1$-C$_6$ alkylamino or arylheterocyclyl C$_1$-C$_6$ alkylamino; or a salt thereof. The compounds can be in D, L, or a mixed form thereof.

The present invention further provides a composition comprising a pharmaceutically acceptable carrier and an effective (e.g., therapeutically or prophylactically effective) amount of at least one of the compounds set forth above. The present invention further provides a method of inhibiting an SH2 domain from binding with a phosphoprotein comprising contacting a sample or substance containing an SH2 domain with a compound of the present invention.

The present invention discloses the use of above compounds in the manufacture of a medicament for the treatment of a condition that responds to the inhibition of phosphoprotein binding to an SH2 domain of a mammal. The present invention further teaches the use of the above compounds in medicine. The compounds find use as a Grb2-SH2 domain inhibitor.

The pharmaceutically acceptable (e.g., pharmacologically acceptable) carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-$\beta$-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook an Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

Embodiments of the compounds have the advantage that they are stable to or in presence of enzymes encountered during in vivo use. Embodiments of the compounds can find use in in vitro and in vivo applications. For example, the compounds can find use as molecular probes as well as in assays to identify, isolate, and/or quantitate receptor or binding sites in a cell or tissue. The compounds also can find use in vivo for studying the efficacy in the treatment of various diseases or conditions involving SH2 domains.

The present invention further provides a method of preventing or treating a disease, state, or condition in a mammal by the use of the compounds of the present invention. In an embodiment, the method involves preventing a disease, state, or condition. In another embodiment, the method involves treating an existing disease, state, or condition.

Preferably, the method involves inhibition of SH2 domain binding with a phosphoprotein. The SH2 domain may involve one or more of the following proteins: Src, Lck, Eps, ras GTPase-activating protein (GAP), phospholipase C, phosphoinositol-3 (P1-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Ab1, Shc, Nck, Crk, CrkL, Syp, Blk, 113TF, 91TF, Tyk2, esecially Src, phospholipase c, phoshoinositol-3 (p1-3)kinase, Grb2, BCR-Ab1, Shc, Nck, Crk, CrkL, Syp, Blk, 113TF, 91TF, and Tyk2.

The method comprises administering to the mammal one or more compounds of the present invention. The disease, state, condition can be a cancer, e.g., a breast cancer or an ovarian cancer, or a tumor such as a solid tumor, e.g., a brain tumor, a prostate tumor, and the like, leukemia including chronic myelocytic leukemia, lymphoma, an autoimmune disease, an inflammatory disease, a metabolic disease, diabetes, obesity, or cardiovascular disease.

The present invention further provides a method of enhancing the therapeutic effect of a treatment rendered to a mammal comprising administering a compound in conjunction with the treatment. By conjunction, it is meant that the inhibitor can be used in any suitable manner, for example, prior to, simultaneous with, or post-administration of the therapeutic agent. Synergistic effects are observed when the SH2 domain binding inhibitor is used in combination with other treatments known to those skilled in the art. The inhibitor enhances the cytotoxicity of the chemotherapeutic treatments. Cancer treatment is particularly suitable for this combination treatment.

The cancer may involve any number of mechanisms. A majority of human breast cancer are dependent upon activation of the Ras signaling pathways through activation of growth factor receptor as the means to achieve continuous cellular proliferation. For example, the cancer may involve overexpression of Her-2/neu. The cancer can be mediated through BCR-Ab1 or the expression of erbB-2 receptor. In cells transformed by p185 erbB-2 overexpression, therapeutic agents affecting Grb2 function at its SH2 domain may interrupt the flow of signal transduction to the ras pathway and thus result in reversal of the cancer phenotype.

The therapeutic treatment can include a chemotherapy, a radiation therapy, and/or a biological therapy. Examples of chemotherapy includes the use of cancer treatment agents such as alkylating agents, hormonal agents, antimetabolites, natural products, and miscellaneous agents. Particular examples of cancer treatment agents include paclitaxel, 5-fluoruracil, and doxorubicin. Examples of biological therapy includes the use of a protein such as an antibody (monoclonal or polyclonal) or a recombinant protein. An example of an antibody is herceptin, which is targeted for inhibiting the erbB-2 receptor. In embodiments, the enhancement of the therapeutic effect comprises blocking of a cell survival factor in the mammal and/or triggering, e.g., enhancing or speeding up, of cell apoptosis. The treatment can be carried out in vivo and/or in vitro.

The present invention further provides a method of inhibiting the MAP kinase activity in a mammal. MAP kinases function in a protein kinase cascade that plays a critical role in the regulation of cell growth and differentiation. MAP kinases are activated by a variety of signals including growth factors, cytokines and hormones through Grb2 and other signaling proteins. For example, the state of threonine and tyrosine phosphorylation of cellular MAP kinase is determined in MDA-453 cells treated with growth factor heregulin (HRG) using a polyclonal antibody specifically recognizing the phosphorylated threonine and tyrosine residues of MAP kinase.

The Grb2 SH2 binding inhibitors are effective in inhibiting the association or binding of Grb2 with activated receptor PTKs. Interaction of native Grb2 protein with phosphotyrosinylated proteins including receptor PTKs can be monitored by immunoprecipitating Grb2 and detecting the amount of phosphotyrosinylated proteins which are coprecipitated using anti-phosphotyrosine Western Blotting The compounds of the present invention exert a cytostatic effect. In embodiments, the compounds of the present invention are free or substantially free of toxicity.

The present invention provides a method for inhibiting cell motility. The present invention also provides a method for inhibiting angiogenesis in an animal. The present invention further provides a method for preventing or treating a variety of diseases, disorders, states or conditions in a mammal, particularly in a human. The present invention provides a method of inhibiting cell motility in a mammal comprising administering to the mammal a peptide having cell signal inhibiting activity and cell motility inhibiting activity; Advantageously, the peptide is free or substantially free of cytotoxicity.

The present invention contemplates to retard or reduce the movement of cells. A number of factors, forces, and/or mechanisms are involved in the movement of cells from one location to another. The method of the present invention is not limited to inhibiting or interfering with one particular factor, force, or mechanism that is involved in the cell movement.

The process of cell movement begins with extension of the cell membrane, the push forward of cytosol (the inner material of the cell), and retraction of the rear of the cell. As the cell membrane initially is propelled forward, an attachment forms between the membrane and the substratum, thereby anchoring the "head" of the cell. Some believe that the cytosol is pushed forward by restructuring of the cytoskeletal network within the cell, although the exact mechanism is unknown. The final step involves the detachment of the "tail" of the cell from the substratum.

It is believed that growth factors activate a signal transduction pathway involving G-proteins, which promote cytoskeletal changes including actin polymerization. External factors promote cell motility by binding to a cell surface receptor and activating a signal transduction pathway, e.g., one involving G-proteins. The signal transduction pathway, in turn, promotes reorganization of the cytoskeleton. A variety of extracellular factors influence cell motility. The movement of a cell following soluble molecules along a concentration gradient is called chemotaxis. Intracellular calcium may play a role in the ability of a cell to recognize concentration gradients. Hormones such as insulin, cytokines, and specific peptide fragments of the extracellular matrix have been identified which stimulate tumor cell motility and chemotaxis.

Aside from instigating cell motility, growth factors stimulate neovascularization, which involves, in part, cell movement. Angiogenesis begins with proteolytic enzyme-mediated breakdown of the basement membrane of a blood vessel. It is believed that breakdown of the basement membrane is regulated by angiogenic factors, such as fibroblast growth factor. Endothelial cells migrate to the area of degradation and invade the surrounding extracellular matrix. Invading endothelial cells proliferate, forming an elongated column of cells. A lumen forms within the solid cell column, thereby forming a vessel, which eventually connects with an existing blood vessel forming a capillary loop (Fotsis et al., *J. Nutr.*, 125: 790S-797S (1995)).

The present invention provides a method for inhibiting angiogenesis in an animal, e.g., a mammal. The method comprises administering to the animal, e.g., mammal, a peptide having cell signal inhibiting activity and cell motility inhibiting activity, wherein the peptide is substantially free of cytotoxicity. Preferably, the peptide affects multiple aspects of the angiogenic process to effectively therapeutically or prophylactically treat angiogenesis. For example, in addition to inhibiting cell signaling and cell motility, the peptide preferably inhibits invasion of epithelial and/or endothelial cells into the extracellular matrix.

In one embodiment, the present invention provides a method of inhibiting cell motility and angiogenesis induced by the hepatocyte growth factor (HGF), particularly the motility derived from a biological response mediated by its cell surface receptor, the c-Met proto-oncogene product, a transmembrane tyrosine kinase. Upon HGF binding, several tyrosine residues within the c-Met intracellular domain are phosphorylated. Some of the phosphorylated domains mediate binding with various signaling proteins, e.g., the Grb2 protein, the p85 subunit of phosphoinositide 3-kinase (PI3K), phospholipase C-gamma, Shc, and Gab1.

The compounds of the present invention inhibit Grb2 SH2 domain binding. In this regard, it is imperative to cellular function that a transducer protein accurately identify activated cellular receptors. Very often, recognition specificity stems from the ability of the transducer protein to recognize a phosphotyrosine surrounded by a specific amino acid sequence. The recognition motif for Grb2 is pYXN wherein pY is phospho-Tyr, X is any amino acid, and N is Asn. The method of the present invention, in an embodiment, is directed to inhibiting cell motility induced or mediated by signaling due to one or more of the above HGF bindings, preferably the binding of HGF c-Met receptor with the Grb2 protein.

Compounds having cell signaling inhibitory activity and cell motility inhibiting activity, such as Grb2-SH2 domain mimetic compounds, are particularly useful in inhibiting neovascularization. Compounds having cell signaling inhibitory activity and cell motility inhibiting activity, such as the Grb2-SH2 domain mimetic compounds, e.g., macrocyclic peptides described herein, inhibit endothelial cell and epithelial cell invasion of matrices and the formation of cell cords.

The compounds of the present invention interact with intracellular signal transducers, thus interfering in the pathways leading to cell proliferation and movement. These biological effects can be utilized to inhibit growth of neoplastic cells, inhibit angiogenesis, and to prevent metastatic spreading. The present invention provides a method for preventing or treating a disease, condition, or state in a mammal that is mediated by the binding of an intracellular signal transducer to a receptor protein tyrosine kinase comprising administering to the mammal a peptide of the present invention.

The compounds of the present invention inhibit cell motility. The peptides prevent scattering of cells.

The cytotoxic effects of agents that disrupt the cytoskeleton, such as colchicine, taxol, cytochalasins, and phalloidin are well-characterized, and are fundamentally different from the anti-motility effects exerted by the compounds employed in the present invention. These compounds may be highly efficacious for the safe treatment of human diseases such as metastatic cancers, e.g., where the role of HGF plays a role in stimulating the invasion of cells into tissue surrounding the tumors and the migration of metastases to distant sites.

The compounds of the present invention are of use in medicine, e.g., in the manufacture of a medicament for the treatment of a condition that responds to the inhibition of phosphoprotein binding to an SH2 domain of a mammal.

The present invention further provides a method for determining the presence of an SH2 domain in a material comprising (a) exposing a sample of said material to a SH2 binding compound and obtaining a first binding result; (b) exposing another sample of said material to a compound described above and obtaining a second binding result; and (c) comparing the first and second binding results to determine whether an SH2 domain is present in the material.

The present invention further provides a method for inhibiting the binding of an intracellular transducer to a receptor protein tyrosine kinase comprising contacting (a) a sample containing the receptor protein tyrosine kinase, (b) the intracellular transducer, and (c) a compound of the present invention under conditions wherein, in the absence of the compound, the receptor protein tyrosine kinase binds to the intracellular transducer; wherein the contacting results in the inhibition of binding of the intracellular transducer to the receptor protein tyrosine kinase.

The present invention further provides for detecting the inhibition of binding of an intracellular transducer to a receptor protein tyrosine kinase comprising: (a) contacting a sample containing the receptor protein tyrosine kinase with the intracellular transducer, separately, in the presence and absence of the compound of the present invention under conditions that allow for binding of the receptor protein tyrosine kinase to the intracellular transducer in the absence of the compound; (b) determining that binding has occurred between the receptor protein tyrosine kinase and the intracellular transducer; and (c) comparing the relative binding levels of the receptor protein tyrosine kinase to the intracellular transducer in the presence and absence of the compound.

The present invention provides (a) a compound of the formula

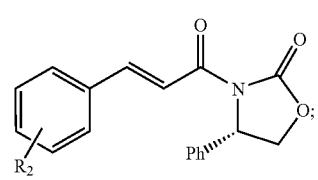

(b) a compound of the formula

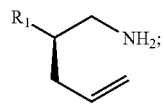

(c) a compound of the formula:

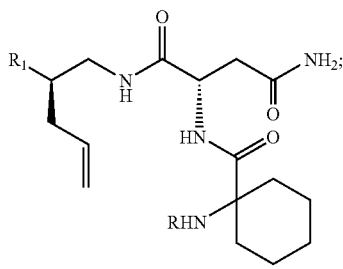

(d) a compound of the formula:

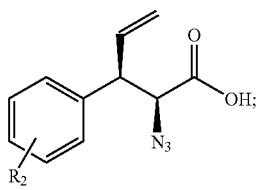

and (e) a compound of formula 24:

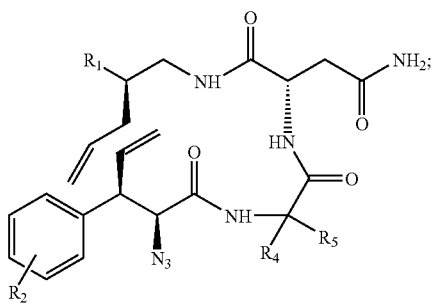

wherein $R_1$ is a lipophile, $R_2$, in combination with the phenyl ring, is a phenylphosphate mimic group or a protected phenylphosphate mimic group; and $R_4$ and $R_5$, independently, are hydrogen, alkyl, cycloalkyl, heterocyclyl, or together form cycloalkyl or heterocyclyl.

The present invention further provides a compound of formula 25:

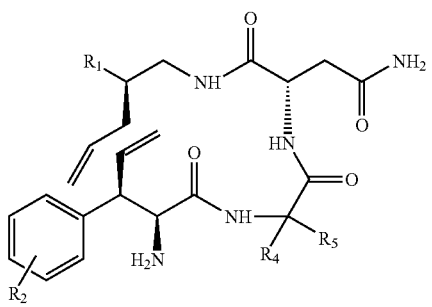

wherein $R_1$ is a lipophile, $R_2$, in combination with the phenyl ring, is a phenylphosphate mimic group or a protected phenylphosphate mimic group; and $R_4$ and $R_5$, independently, are hydrogen, alkyl, cycloalkyl, heterocyclyl, or together form cycloalkyl or heterocyclyl.

The present invention further provides a compound of formula 20

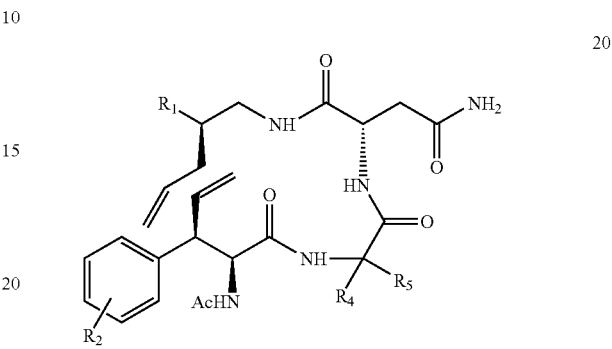

wherein $R_1$ is a lipophile, $R_2$, in combination with the phenyl ring, is a phenylphosphate mimic group or a protected phenylphosphate mimic group; and $R_4$ and $R_5$, independently, are hydrogen, alkyl, cycloalkyl, heterocyclyl, or together form cycloalkyl or heterocyclyl.

The present invention further provides (a) a compound of the formulas

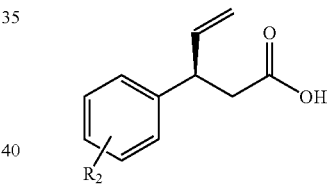

(b) a compound of the formula

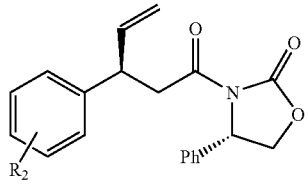

and (c) a compound of the formula 31

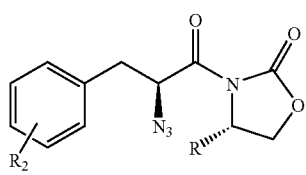

wherein $R_2$, in combination with the phenyl ring, is a phenylphosphate mimic group or a protected phenylphosphate mimic group, and R is aralkyl, aryl, or alkyl. In embodiments, R is benzyl.

In preferred embodiments of the intermediate compounds, the phenylphosphate mimic is phosphonomethyl or an ester thereof. In certain embodiments, the lipophile is aralkyl, arylheterocyclylalkyl, alkylaminocarbonyl, alkenylaminocarbonyl, arylaminoacrabonyl, alkoxyalkyl, aryloxyalkyl, or aralkoxyalkyl, wherein the aryl portion is phenyl or naphthyl and the alkyl portion is a $C_1$-$C_6$ alkyl, and the heterocyclyl is a 3-7 membered ring having one or more of N, O, or S.

The present invention further provides a method for preparing a compound of formula 31 wherein $R_2$, in combination with the phenyl ring, is a phenylphosphate mimic group or a protected phenylphosphate mimic group, and R is aralkyl, aryl, or alkyl comprising: (a) treating a compound of the formula 26

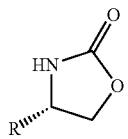

26 with a compound of the formula 27

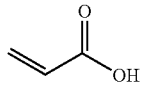

27 to obtain a compound of the formula 28

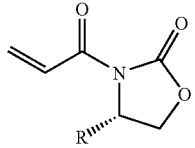

28

(b) treating the compound of formula 28 with a compound of formula 11

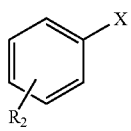

11 to obtain a compound of formula 29

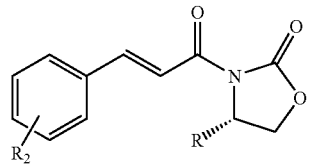

29

(c) reducing the compound of formula 29 to obtain a compound of formula 30

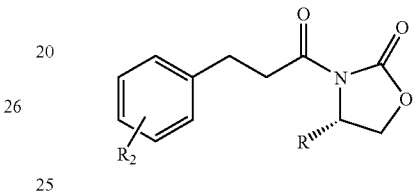

30

(d) treating the compound of formula 30 with an alkali metal salt of bis(trimethylsilyl)amide and trisyl azide, to obtain the compound of formula 31. In embodiments, R is benzyl.

The present invention further provides a method for preparing a compound of formula 3; wherein $R_1$ is a lipophile; $R_2$, in combination with the phenyl ring, is a phenylphosphate mimic group or a protected phenylphosphate mimic group; and $R_4$ and $R_5$, independently, are hydrogen, alkyl, cycloalkyl, or heterocyclyl, or $R_4$ and $R_5$ together form a cycloalkyl or heterocyclyl, the method comprising:

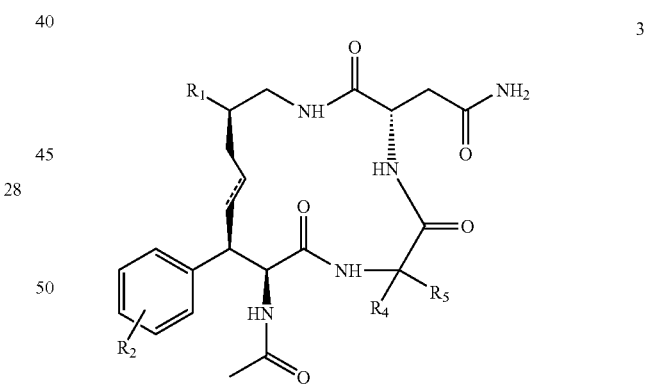

3

(a) providing a compound of formula 24; (b) reducing the azido group in the compound of formula 24 to an amino group to obtain a compound of formula 25; (c) acetylating the amino group of the compound of formula 25 to obtain a compound of formula 20; and (d) carrying out an olefin metathesis reaction on the compound of formula 20, thereby obtaining the compound of formula 3.

The azido group can be reduced by methods known to those skilled in the art, for example, by treating with triphenyl phosphine in a suitable medium, e.g., a mixture of THF and water. The amino group is acetylated to obtain the compound of formula 20. Acetylation can be carried out by methods known to those skilled in the art, e.g., by the use of acetic anhydride and a base such as pyridine. An olefin metathesis reaction can be carried out by the use of a suitable catalyst, e.g., catalysts that are functionally tolerant such as those developed by Schrock or Grubbs, preferably a ruthenium based catalyst such as the Grubbs catalyst A below:

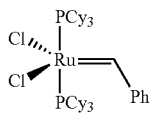

A

The above catalyst A is not significantly affected by air or moisture and compounds containing nitrogen functional groups or bulky groups can be ring closed by the metathesis reaction. The metathesis reaction can be carried out in a suitable solvent, e.g., halogenated solvents such as dichloromethane. The reaction can be carried out under mild or moderate conditions, e.g., at the reflux temperature of dichloromethane.

The present invention further provides a method for preparing a compound of formula 24, wherein $R_1$ is a lipophile, $R_2$, in combination with the phenyl ring, is a phenylphosphate mimic group or a protected phenylphosphate mimic group; and $R_4$ and $R_5$, independently, are hydrogen, alkyl, cycloalkyl, heterocyclyl, or together form cycloalkyl or heterocyclyl, the method comprising treating a compound of formula 18 with a compound of formula 23:

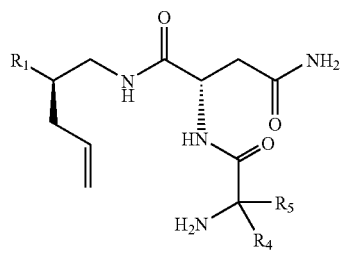

18

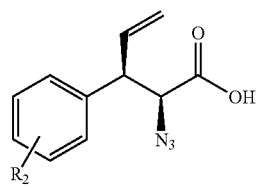

23

The compound of formula 18 can be treated with the compound of formula 23 under a suitable base to promote the condensation of the free amine with the acid group. Preferably, the acid group is pre-activated to an ester. For example, the compound of formula 23 can be pre-activated by reaction with an alcohol such t-butanol, a coupling agent such as DIPCDI in a dry solvent such as N,N-dimethylformamide. To the pre-activated solution of the compound of formula 23 is added the compound of formula 18, and the mixture is stirred, e.g., at room temperature (20±3° C.). The reaction can be carried out for a suitable length of time, e.g., by stirring for about 12 hours. The solvent is removed, e.g., by evaporation, and the residue is dissolved in ethyl acetate, washed with a saturated solution of sodium bicarbonate, and followed by water, and by brine washes. The resulting product is dried, e.g., over anhydrous sodium sulfate to obtain the compound of formula 24.

The present invention further provides a method for preparing a compound of formula 18 wherein $R_1$ is a lipophile; and $R_4$ and $R_5$, independently, are hydrogen, alkyl, cycloalkyl, heterocyclyl, or together form cycloalkyl or heterocyclyl, the method comprising: (a) treating a compound of formula 7

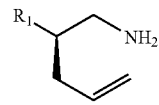

7 with a compound of the formula B:

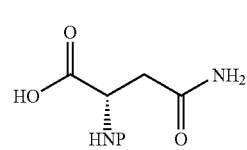

B to obtain a compound of formula 16

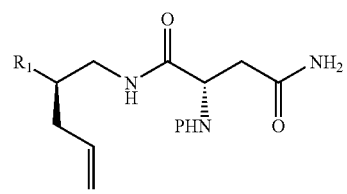

16 wherein P is an amine protecting group;

(b) treating the compound of formula 16 with an amine protected amino acid of the formula C

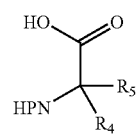

C to obtain a compound of formula 17

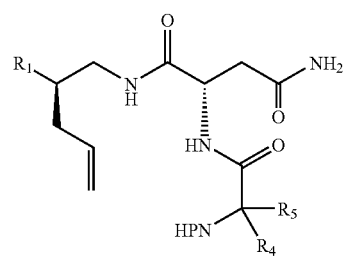

17 and (c) removing the amine protecting group to obtain the compound of formula 18.

The compound of formula 7 is combined with compound B, which is an amine protected asparagine. Any suitable amine protecting group, e.g., Boc or Fmoc, can be employed. The compound B is pre-activated, e.g., by reacting with t-butanol and DIPCDI in dry DMF. The compound of formula 7 is added to pre-activated B. The resulting mixture is stirred, e.g., at room temperature (20±3° C.). The reaction can be carried out for a suitable length of time, e.g., by stirring for about 12 hours. The solvent is removed, e.g., by evaporation, and the residue is washed with ethyl acetate (e.g., up to 5 times). The product can be purified, e.g., by chromatography.

The present invention further provides a method for preparing a compound of the formula 7 comprising: (a) treating compound D

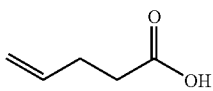

D with compound E

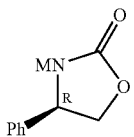

E to obtain a compound of formula 12

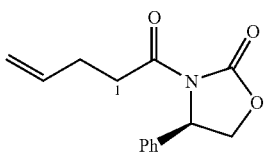

12

(b) replacing a hydrogen on the CH$_2$ adjacent to the carbonyl carbon (1) of the compound of formula 12 with a lipophile to obtain a compound of formula 13:

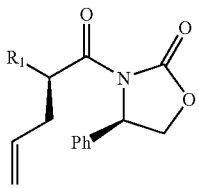

13

(c) reducing the compound of formula 13 to obtain the compound of formula 14

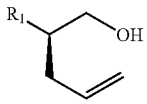

14 and (d) replacing the hydroxyl group of the compound of formula 14 with an amino group, thereby obtaining the compound of formula 7; wherein $R_1$ is a lipophile and M is a metal.

The compound of formula 7 can be prepared from the Evan's reagent, (R)-(−)-4-phenyl-2-oxazolidinone (compound of formula 12). The compound of formula 12 is prepared by coupling or condensing compounds D and E. The metal M can be an alkali metal such as lithium. The coupling is carried out by the use of trimethylacetyl chloride in a suitable solvent such as n-methyl pyrrolidone. The resulting compound of formula 12 is converted to the compound of formula 13 by treating the compound of formula 12 with a base and a haloalkylaryl compound, e.g., 1-bromomethyl naphthalene. A suitable base is LiHMDS. The compound of formula 14 can be obtained by treating the compound of formula 13 with a reducing agent, e.g., a metal hydride such as LiAlH4, preferably at a low temperature, e.g., at −78° C. to room temperature. The compound of formula 14 is contacted with phthalidimide and triphenyl phosphine. The compound of formula 7 can be obtained by treating with ethanol, water, and hydrazine.

The present invention further provides a method for preparing a compound of formula 23 comprising (a) providing a compound of formula 8

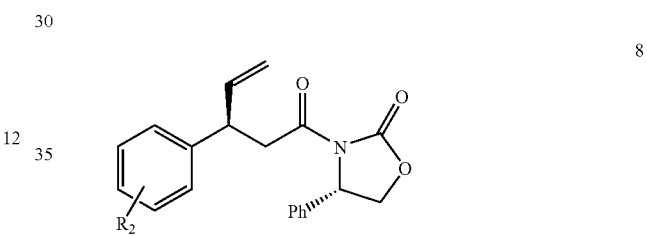

8

(b) treating the compound of formula 8 with a base and trisyl azide to obtain a compound of formula 22

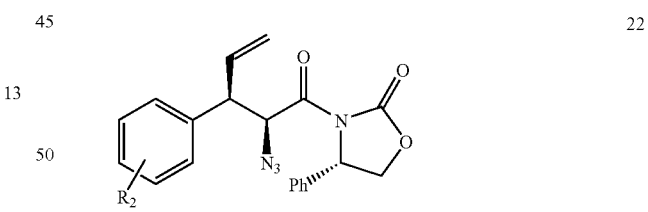

22 and (c) treating the compound of formula 22 with an alkaline peroxide, thereby obtaining the compound of formula 23; wherein $R_2$, in combination with the phenyl ring, is a phenylphosphate mimic group or a protected phenylphosphate mimic group. An example of a suitable base is NaHMDS. The treating (b) is carried out at a low temperature, e.g., at −78° C. In (c), an alkali such as lithium hydroxide can be employed in combination with hydrogen peroxide.

The present invention further provides a method for preparing a compound of formula 8 comprising: (a) providing a compound of formula 9

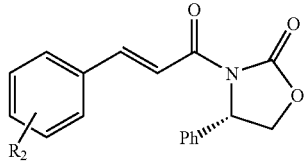

9 and (b) treating the compound of formula 9 with vinyl magnesium bromide and PhSCu; wherein $R_2$, in combination with the phenyl ring, is a phenylphosphate mimic group or a protected phenylphosphate mimic group.

The present invention further provides a method for preparing a compound of formula 9 comprising treating a compound of formula 10

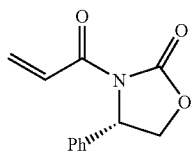

10 with a compound of formula 11, wherein $R_2$, in combination with the phenyl ring, is a phenylphosphate mimic group or a protected phenylphosphate mimic group, and X is a halogen. A preferred halogen is bromine. Compounds of formulas 10 and 11 are combined. A base such as triethylamine, a palladium catalyst, e.g., $Pd(OAc)_2$, and a phosphine such as tri-o-tolylphosphine are employed. The reaction can be carried out at reflux.

The present invention further provides a method for preparing a compound of formula 10 comprising treating compound F

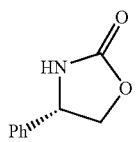

F with compound G

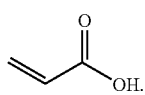

G

The treating (coupling or condensing) can be carried out in the presence of an acid chloride, e.g., pivalyl chloride, a trialkylamine such as triethylamine, and a base such as BuLi at a low temperature, e.g., −78° C. to room temperature.

The present invention further provides a method for preparing a compound of formula 4 comprising:

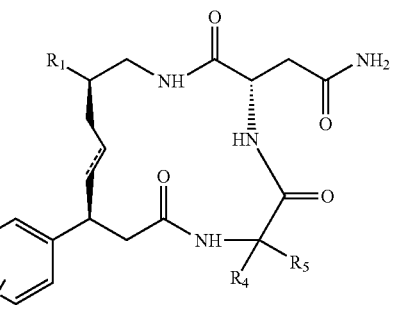

4

(a) treating the compound of formula 18 with a compound of formula 6

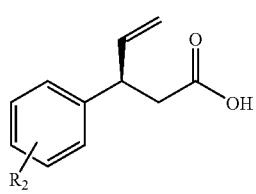

6 to obtain a compound of formula 5

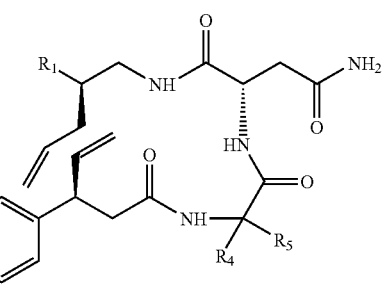

5

(b) treating the compound of formula 5 with a Grubbs catalyst to compound of formula 19

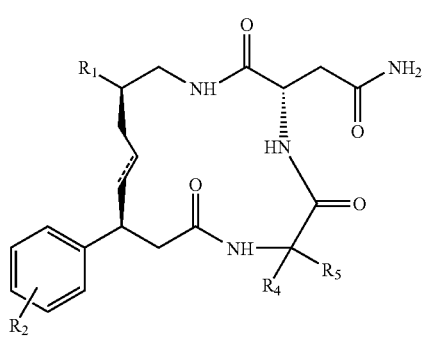

19 and (c) treating the compound of formula 19 with a mixture of trifluoroacetic acid, water, and trimethylsilane to obtain the compound of formula 4; wherein $R_1$ is a lipophile, $R_2$, in combination with the phenyl ring, is a phenylphosphate mimic group or a protected phenylphosphate mimic group; and $R_4$ and $R_5$, independently, are hydrogen, alkyl, cycloalkyl, heterocyclyl, or together form cycloalkyl or heterocyclyl. The treating (coupling or condensing) of the compounds of formulas 18 and 6 can be carried out by pre-activating the acid to an ester, e.g., by contacting with t-butanol and DIPCDI, and the pre-activated compound is contacted with the compound of formula 18. The conversion of the compound of formula 5 to the compound of formula 19 can be carried out by the use of a Grubbs catalyst.

The following examples further illustrate the present invention but, of course, should not be construed as in any way limiting its scope.

EXAMPLE 1

This Example illustrates a method of preparing some of the compounds or intermediates of the present invention. The method is illustrated schematically in FIGS. 1-9. (S)-N-Acroyl-4-phenyl-2-oxazolidinone, 10. To a solution of acrylic acid (5.188 g, 72 mmol) in 200 ml of anhydrous THF containing 7.283 g of N-methylmorpholine was added pivaloyl chloride (8.68 g, 72 mmol) at 0° C. under argon atmosphere, then stirred at –78° C. for 1 hr. Then a cooled solution of Lithium (s)-4-phenyl-2-oxazolidinone (prepared by addition of BuLi (1.6 M, 37.5 ml, 60 mmol) to a suspension of (s)-(+)-4-phenyl-2-oxazolidinone (9.791 g, 60 mmol) in 200 ml of anhydrous THF at –78° C. under argon, stirred for 30 min) was added by cannula. After being stirred at –78° C. for 2 hr, the resulting solution was raised to room temperature, stirred overnight. 100 ml of saturated $NH_4Cl$ solution was added to, quench the reaction, and the THF was evaporated under reduced pressure, the residue was extracted with ethyl acetate, washed with water and saturated brine, dried over $Na_2SO_4$. Concentration and purification by silica gel chromatography (Hexanes and ethyl acetate, from 10:1 to 4:1) afforded 12.304 g of product 10 (78.7% of Yield). NMR (in $CDCl_3$): 7.584~7.475 (1H, dd, J=10.5, 16.85 Hz), 7.443~7.302 (5H, m), 6.534~6.459 (1H, dd, J=1.71, 17.09 Hz), 5.917~5.868 (1H, dd, J=1.71, 10.26 Hz), 5.531~5.481 (1H, dd, J=3.91, 8.55 Hz), 4.811 (1H, t, J=8.79 Hz), 4.421~4.370 (1H, dd, J=3.91, 8.79 Hz).

Di-tert-butyl p-Bromobenzylphosphite 11a. To the solution of di-tert-butylphosphite (9.715 g, 50 mmol) in 150 ml of anhydrous THF was added BuLi (2.5 M in hexanes, 20 ml, 50 mmol) dropwise at –78° C. under Argon, the solution was stirred at –78° C. for 30 min, then raised to 0° C., stirred for additional 1 hr. To the resulting solution was added a solution of 4-bromobenzyl bromide in 50 ml of anhydrous THF at 0° C., after stirring for additional 2 hr at the same temperature, the solution was raised to room temperature, stirred overnight. 100 ml of water was added to quench the reaction and the THF was evaporated under reduced pressure. The residue was extracted with ethyl acetate, washed with water and saturated brine, dried over $Na_2SO_4$. Concentration and purification by silica gel chromatography (Hexanes and ethyl acetate, from 10:1 to 4:1) afforded 16.5 g of product as white solid 11a (91% of Yield). NMR (in $CDCl_3$): 7.415 (2H, d, J=8.30 Hz), 7.157 (2H, dd, J=2.44, 8.56 Hz), 2.987 (2H, d, J=21.49 Hz), 1.431 (18H, s).

Compound 9a. To the mixture of N-acroyl-(s)-4-phenyl-2-oxazolidinone, 10 (6.402 g, 27.81 mmol), di-tert-butyl p-bromobenzylphosphite 11a (10.10 g, 27.81 mmol), Palladium acetate (309 mg) and tri-o-tolylphosphine in 200 ml of round bottom flask was added, 100 ml of anhydrous triethylamine, the resulting solution was refluxed under Argon overnight, a large amount of solid precipitate appeared, and some silver mirror was generated on the flask wall. The triethylamine solvent was evaporated and the residue was dissolved in 150 ml of dichloromethane, then the solid palladium compound was removed by filtration. The solution was washed with water and brine, dried over $Na_2SO_4$, and evaporated to dryness to give yellow solid product. The crude product was recrystallized through Hexanes-EtOAc-$CH_2Cl_2$ mixture to give 8.930 g of white solid product 9a, from the liquid solution, 2.95 g of product was recovered by chromatography (combined yield 85.5%). NMR (in $CDCl_3$): 7.920 (1H, d, J=14.89 Hz), 7.768 (1H, d, J=16.36 Hz), 7.529 (2H, d, J=7.57 Hz), 7.48~7.18 (7 H, m), 5.570 (1H, dd, J=3.66, 8.54 Hz), 4.751 (1H, t, J=8.79 Hz), 4.33 (1H, dd, J=3.91, 8.79 Hz), 3.066 (2H, d, J=21.72 Hz), 1.462 (18H, s); FAB-MS (+Ve): 500 ($MH^+$), 444 ($MH^+$-$C_4H_8$), 388 ($MH^+$-$2C_4H_8$).

Compound 8a. To a slurry of cuprous thiophenoxide (1.7271 g, 10 mmol) in 300 ml of dry ether under argon at –40° C. was added vinyl magnesium bromide in THF (1.0 M, 30 ml, 30.0 mmol, 3 eq.) dropwise, the mixture was allowed to warm up to –25° C. until a color change (from brown to black-green) indicating the formation of complex $PhSCu(RMgX)_n$, was observed, the mixture was allowed to stir at this temperature for additional 1 hr. Then to the mixture was added a pre-cooled (–40° C.) solution of compound 9a in 100 ml of anhydrous THF dropwise, the reaction mixture was stirred at –40° C. for 3 hr (the reaction was monitored by T.L.C., till the starting material disappeared). The reaction mixture was poured into ice-cooled $NH_4Cl$ solution, the solid coprous salt was removed by filtration. After evaporation of THF, the residue was extracted with ethyl acetate, washed with water, saturated brine, and dried over $Na_2SO_4$. Concentration and purification by silica gel chromatography afforded 2.967 g of product 8a as white solid (56% of yield). NMR (in $CDCl_3$): 7.410~7.100 (9H, m), 5.961 (1H, ddd, J=6.59 Hz), 5.306 (1H, dd, J=3.41, 8.54 Hz), 4.984 (1H, ddd, J=1.22, 1.22, 10.35 Hz), 4.934 (1H, ddd, J=1.22, 1.22, 17.09 Hz), 4.585 (1H, t, J=8.79 Hz), 4.235 (1H, dd, J=3.32, 9.04 Hz), 3.89 (1H, m), 3.49 (1H, dd, J=8.05, 16.35 Hz), 3.334 (1H, dd, &=7.08, 16.36 Hz0, 3.006 (2H, d, J=21.49 Hz), 1.426 (18H, s). FAB-MS (+VE): 472 ($MH^+$-$C_4H_8$), 416 ($MH^+$-$2C_4H_8$).

Compound 6a. To the solution of compound 8a (527 mg, 1 mmol) in 16 ml of THF-$H_2O$ mixture (3:1) at 0° C. was added $H_2O_2$ (30%, 509 μl, 5.0 mmol) via a syringe over 1 min, this was followed by the addition of LiOH (84 mg, 2 mmol in 2 ml of water). After stirring at 0° C. for 1 hr, the reaction mixture was raised to room temperature, stirred overnight. 628 mg of $Na_2SO_3$ (5.0 mmol) in 4.0 ml of water was added to destroy the remained hydrogen peroxide, and THF was evaporated at 30° C. The remained mixture was extracted with dichloromethane to remove the Evan's reagent, then the aqueous solution was poured into 25 ml of ice-cooled 0.2 M HCl solution, extracted with ethyl acetate, washed with ice-cooled water and brine, dried over $Na_2SO_4$, concentrated, and taken to dryness under high vacuum to give 204 mg (80% of yield) of product 6 as foam. NMR (in $CDCl_3$): 7.22~7.17 (2H, dd, J=2.20, 8.30 Hz), 7.141 (2H, d, J=8.55 Hz), 5.990 (1H, m), 5.12~5.00 (2H, m), 3.85 (1H, m), 2.955 (2H, d, J=21.48 Hz), 2.798 (1H, dd, J–7.57, 15.13 Hz), 2.696 (1H, dd, J=8.06, 15.38 Hz), 1.409 (9H, s), 1.397 (9H, s). FAB-MS (+VE):

(R)-N-(4-pentenoic)-4-phenyl-2-oxazolidinone 12a. To a solution of 4-pentenoic acid (3.604 g, 36 mmol) in 100 ml of anhydrous THF containing 3.645 g (36 mmol) of N-methylmorpholine was added pivaloyl chloride (4.34 g, 36 mmol) at −78° C. under argon atmosphere, the mixture was stirred at −78° C. for 30 min, then raised to 0° C., stirred for additional 1 hr, then cooled to −78° C. again, stirred for 15 min before adding the solution of lithium oxazolidinoe [prepared from BuLi (1.6 M, 18.75 ml, 30 mmol) and (R)-(−)-4-phenyl-2-oxazolidinone (4.895 g, 30 mmol) in 200 ml of anhydrous THF at −78° C. under argon, 30 min] through cannula. After stirred at −78° C. for 2 hr, the resulting solution was raised to room temperature, stirred overnight. 100 ml of ice-cooled water was added to quench the reaction, and the THF was evaporated under reduced pressure, the residue was extracted with ethyl acetate, washed with water and saturated brine, dried over $Na_2SO_4$. Concentration and purification by silica gel chromatography (Hexanes and ethyl acetate, from 10:1 to 4:1) afforded 6.82 g of product 12a (70% of Yield). NMR ((in $CDCl_3$): 7.435~7.270 (5H, m), 5.891~5.730 (1H, ddt, J=6.60, 10.26, 16.85 Hz), 5.438 (1H, dd, J=3.66, 8.55 Hz), 5.10~4.95 (2H, m), 4.704 (1H, t, J=8.79 Hz), 4.297 91H, dd, J=3.66, 9.03 Hz), 3.061 (2H, t, J=7.08 Hz), 2.370 (2H, m). FAB-MS (+VE): 246 ($MH^+$).

Compound 13a. To the solution of (R)-N-(4-pentenoic)-4-phenyl-2-oxazolidinone 12a (6.885 g, 27.3 mmol) in 150 ml of dry THF was added the solution of LiHMDS (1.0 M in THF, 27.3 ml, 27.3 mmol) at −78° C. under argon, the resulting solution was stirred at −78° C. for 2 hr, then a pre-cooled solution of 1-(bromomethyl)-naphthalene (12.07 g, 54.3 mmol) in 50 ml of THF was added, the resulting solution was stirred at −78° C. for 4 hr, then raised to room temperature, stirred overnight. 100 ml of ice-cooled water was added to quench the reaction, and the THF was evaporated under reduced pressure, the residue was extracted with ethyl acetate, washed with water and saturated brine, dried over $Na_2SO_4$. Concentration and purification by silica gel chromatography (Hexanes and ethyl acetate, from 20:1 to 6:1) afforded 9.256 g of product 13a (88% of Yield). NMR (in $CDCl_3$): 8.805 (1H, d, J=7.81 Hz), 7.845 (1H, dd, J=2.19, 6.83 Hz), 7.710 (1H, d, J=8.06 Hz), 7.556~7.440 (2H, m), 7.304~7.201 (5H, m), 7.141 (1H, dd, J=0.73, 6.83 Hz), 6.993 (2H, m), 5.926~5.761 (1H, ddt, J=7.32, 10.01, 16.84 Hz), 5.398 (1H, dd, J=4.15, 8.79 Hz), 5.142~5.045 (2H, m), 4.611 (1H, t, J=8.79 Hz), 4.542 (1H, m), 4.144 (1H, dd, J=4.15, 8.79 Hz), 3.424 (1H, dd, J=8.30, 13.67 Hz), 3.165 (1H, dd, J=6.59, 13.91 Hz), 2.519 (1H, m), 2.239 (1H, m). FAB-MS (+VE): 386 ($MH^+$)

Compound 14a. A solution of $LiAlH_4$ (0.90 g, 95%, 22,47 mmol) in 100 ml of dry THF was cooled to −78° C., to the solution was added a pre-cooled solution of naphthalene compound 13a (8.654 g, 22.47 mmol) in 50 ml of dry THF at −78° C., the mixture was stirred at −78° C. for 1 hr, then raised to 0° C. over 1 hr. After 0.5 hr at 0° C., the clear solution was cooled to −78° C., and 15 ml of ethyl acetate was added to destroy the remained $LiAlH_4$. The reaction was quenched with aqueous $NH_4Cl$ solution at −78° C., and after warming up to room temperature, diluted with water, extracted with ether, washed with water and brine, dried over $Na_2SO_4$. Concentration and purification by silica gel chromatography (Hexanes and ethyl acetate, from 20:1 to 10:1) afforded 3.630 g (70% of yield) of product 14a as oil. NMR (in $CDCl_3$): 8.069 (1H, m), 7.871 (1H, m), 7.744 (1H, d, J=7.81 Hz), 7.560~7.324 (1H, m), 5.976~5.810 (1H, m), 5.200~5.100 (2H, m), 3.610 (2H, d, J=5.13 Hz), 3.156 (1H, dd, J=7.81, 13.92 Hz), 3.060 (1H, dd, J=6.59, 13.91 Hz), 2.30~2.20 (2H, m), 2.15~2.06 (1H, m); FAB-MS (+VE): 226 ($M^+$).

Compound 15a. To the solution of the alcohol 14a (3.492 g, 15.43 mmol) in 30 ml of THF was added phthalimide (2.282 g, 15.43 mmol) and triphenylphosphine (4.06 g, 15.43 mmol) at 0° C., this was followed by the addition of diisopropyl azodicarboylate (3.131 g, 15.43 mmol). After stirring had been continued overnight at room temperature, THF was evaporated, the residue was purified by chromatography to give 4.01 g (73% of yield) of product 15a as sticky oil. NMR (in $CDCl_3$): 7.962 (1H, m), 7.827~7.633 (6H, m), 7.518~7.309 (4H, m), 5.932~5.767 (1H, ddt, J=7.08, 10.25, 17.09 Hz), 5.15~5.00 (2H, m), 3.785 (1H, dd, J=7.57, 13.67 Hz), 3.688 (1H, dd, J=7.33, 13.67 Hz), 3.094 (2H, d, J=7.32 Hz), 2.696 (1H, m), 2.151 (2H, m). FAB-MS (+VE): 356 ($MH^+$).

Chiral amine 7a. To the solution of phthalimide 15a (3.945 g, 11.1 mmol) in 100 ml of ethanol containing 820 µl of water was added 867 mg (26.7 mmol) of hydrazine, the resulting solution was refluxed under argon for 4 hr, and a large amount of solid precipitate appeared. The solution was cooled to room temperature, the solid was filtered off, washed with small amount of ethanol. The combined liquid solution was evaporated to dryness, the residue oil was purified by silica gel chromatography (Hexanes and ethyl acetate, 2:1, plus 1% v/v of $NH_3$-MeOH solution) to give 1.916 g (77% of yield) of desired product 7a as oil. NMR (in $CDCl_3$): 8.072 (1H, m), 7.863 (1H, m), 7.733 (1H, d, J=8.06 Hz), 7.551~7.443 (2H, m), 7.398 (1H, t, J=7.08 Hz), 7.313 (1H, m), 5.950~5.785 (1H, ddt, J=7.08, 10.36, 17.09 Hz), 5.175~5.050 (2H, m), 3.065 (2H, d, J=7.32 Hz), 2.718 (2H, d, J=5.61 Hz), 2.30~2.10 (2H, m), 2.05~1.92 (1H, m); FAB-MS (+VE): 226 ($MH^+$).

Compound 16a. To the solution of amine 7a (1.9164 g, 8.51 mmol) was added the pre-activated Boc-Asn [Formed by the reaction of Boc-Asn (1.974 g, 8.51 mmol), HOBt (1.15 g, 8.51 mmol), and DIPCDI (1.078 g, 8.51 mmol) in 20 ml of dry DMF, 10 min]. The resulting mixture was stirred at room temperature for 12 hr, then DMF was evaporated. The resulting solid compound was washed with ethyl acetate (30 ml×5) to give 3.44 g of pure compound 16a, the combined liquid phase was concentrated, purified by silica gel flash chromatography (chloroform and methanol, from 20:1 to 9:1) to give 112 mg of product 16a (95% of combined yield). NMR (in $CDCl_3$): 8.025~7.961 (1H, m), 7.870~7.831 (1H, m), 7.724 (1H, d, J=7.82 Hz), 7.551~7.297(4H, m), 6.955 (1H, s, br), 6.30~6.10 (2H, m, br), 5.920~5.750 (1H, m), 5.568 (1H, s, br), 5.175~5.050 (2H, m), 4.50-4.350 (1H, m), 3.252 (2H, m), 3.108~2.838 (3H, m), 2.561~2.474 (1H, dd, J=6.35, 15.63 Hz), 2.121 (3H, m), 1.444 (9H, s); FAB-MS (+VE): 440 ($MH^+$), 384 ($MH^+$-$C_4H_8$)

Compound 17a. To the suspension of compound 16a (3.56 g, 8.08 mmol) in 20 ml of dichloromethane was added 15 ml of trifluoroacetic acid, the suspension turned to be a clear solution. The solution was stirred at room temperature for 1 hr, then dichloromethane and TFA was evaporated. The residue was dissolved in 150 ml of ethyl acetate, neutralized with saturated $NaHCO_3$ solution, then washed with brine, dried over $Na_2SO_4$, concentrated, taken to dryness under high vacuum to give quantity yield of free amine as an oil. NMR (in $CDCl_3$): 8.10~7.27 (7H, m), 5.87~5.65 (1H, m), 5.20~4.90 (2H, m), 3.95 (1H, m, br), 3.40~2.60 (5H, m), 2.25~2.00 (4H, m). The obtained amine was dissolved in 20 ml of dry DMF, to the solution was added the pre-activated Fmoc-1-amino-cyclohexane carboxylic acid [Formed by reaction of Fmoc-1-amino-cyclohexane carboxylic acid (3.107 g, 8.51 mmol), HOBt (1.15 g, 8.51 mmol), DIPCDI (1.078 g, 8.51 mmol) in 20 ml of DMF, 10 min], the resulting mixture was stirred at room temperature for 12 hr, the DMF was evaporated, the residue was dissolved in 200 ml of dichloromethane, washed with saturated $NaHCO_3$ solution, water, and brine, dried over $Na_2SO_4$. Concentration and purification by silica gel chromatography (chloroform and methanol, from 20:1 to 9:1) afforded 4.088 g of 17a (70% of yield). NMR (in $CDCl_3$): 8.105 (1H, d, J=8.06 Hz), 7.997 (1H, d, J=8.06 Hz0, 7.806~7.645 94H, m), 7.480~7.189 (11H, m), 6.061 (1H, s, br), 5.835.66 (1H, m), 5.267 (1H, s, br), 5.232 (1H, s, br), 5.07~4.90 92H, m0, 4.747 (1H, m), 4.306~4.006 (3H, m), 3.32~3.00 (4H, m), 2890 (1H, dd, J=5.13, 14.16 Hz), 2.426 (1H, dd, J=4.39, 14.89 Hz), 2.158~1.530 (13H, m); FAB-MS (+VE): 687 ($MH^+$)

Compound 18a. Compound 17a (4.088 g, 5.957 mmol) was dissolved in 50 ml of acetonitrile, to the solution was added 4.0 ml of piperidine, the resulting solution was stirred at room temperature for 2 hr. The solvent was evaporated, the residue was purified by silica gel chromatography to give free amine 2.707 g 18a (98% of yield). NMR (in $CDCl_3$): 8.893 (1H, d, J=6.84 Hz), 7.982 (1H, m), 7.851 (1H, m), 7.724 (1H, d, J=7.81 Hz), 7.55~7.258 (7H, m), 6.309 (1H, s, br), 5.905 5.754 (1H, m), 5.540 (1H, s, br). 5.134~5.070 (2H, m), 4.683 (1H, dd, J=6.10, 10.74 Hz), 3.30~3.209 (2H, m), 3.076 (1H, dd, J=6.59, 14.16 Hz), 2.966 (1H, dd, J=6.35, 13.92 Hz), 2.825 91H, dd, J=4.39, 15.14 Hz), 2.561 (1H, dd, J=6.53, 14.59 Hz), 2.166 (2H, d, J=5.86 Hz), 2.054~1.234 (10H, m).

Compound 5a. To the solution of amine 18a (376 g, 0.801 mmol) in 5 ml of dry DMF was added the pre-activated ester solution of 6a [Formed by the reaction of 6a (306 mg, 0.801 mmol), HOBt (109 mg, 0.801 mmol), and DIPCDI (101 mg, 0.801 mmol) in 5 ml of dry DMF, 10 min]. The resulting mixture was stirred at room temperature for 12 hr, then DMF was evaporated. The residue was dissolved in 50 ml of ethyl acetate, washed with saturated $NaHCO_3$ solution, water, and brine, dried over $Na_2SO_4$. Concentration and purification by silica gel chromatography (chloroform and methanol, from 20:1 to 9:1) afforded 569 mg (86% of yield) of product 5a as foam). NMR (in $CDCl_3$): 8.054 (1H, d, J=8.05 Hz), 7.85~7.64 (4H, m), 7.550~7.384 (4H, m), 7.154 (2H, dd, J=2.44, 7.81 Hz), 6.991 (2H, d, J=, 8.05 Hz), 6.283 (1H, s, br), 5.959~5.772 (H, m), 5.414 (1H, s, br), 5.125~4.903 (4H, m), 4.719 (1H, m), 3.728 (1H, M), 3.367 (1H, m), 3.200~2.910 (3H, m), 2.650~2.450 (3H, m), 2.300~2.005 (5H, m), 1.950~1.090 (11H, m), 1.434 (9H, s), 1.414 (9H, s); FAB-MS (+VE): 828 ($M^+$), 772 ($M^+$-$C_4H_8$), 716 ($M^+$-$2C_4H_8$).

Compound 19a. To the solution of compound 5a (429 mg, 0.518 mmol) in 120 ml of anhydrous dichloromethane (deoxygenated with Argon) was added via a syringe of Ruthenium catalyst (180 mg, 0.218 mmol, 0.4 eq.) in 37 ml of dichloromethane, the solution was refluxed under Argon for 60 hr, monitored by T.L.C. Then, the solvent was evaporated, the residue was purified by silica gel chromatography (chloroform-EtOAc-MeOH, from 2:1:0 to 14:7:1) to give 279 mg (67% of yield) of product 19a. FAB-MS (+VE): 801 ($MH^+$), 745 ($MH^+$-$C_4H_8$), 689 ($MH^+$-$2C_4H_8$).

Product 4a. The compound 19a (179 mg) was treated with a solution made of TFA-TES-$H_2O$ (3.7 ml-0.1 ml-0.2 ml) at room temperature, after 1 hr, the solvents were evaporated. To the residue was added ether, a large amount of solid product precipitated, the product was separated by centrifuge, then washed with ether, separated by centrifuge again, the resulting solid product was dried under high vacuum to give 144 mg of crude product. The crude compound was dissolved in 16 ml of acetonitrile-water solution (1:1), purified by HPLC to give 73 mg (60% of yield) of pure compound 4a. NMR (in DMSO): 8.395 (1H, s), 8.234 (1H, d, J=7.81 Hz), 8.116 (1H, d, J=8.06 Hz), 7.893 (1H, d, J=7.57 Hz), 7.750 (1H, m), 7.561~7.375 (6H, m), 7.150~7.020 (5H, m), 5.550 (1H, dd, J=9.52, 14.16 Hz), 5.43~5.30 (1H, m0, 4.269 (1H, m), 3.861 (1H, m0, 3.587 (1H, dd, J=5.61, 11.72 Hz0, 3.156 (1H, dd, J=5.66, 14.40 Hz), 2.950~2.300 98H, m), 2.250~1.100 (11H, m); FAB-MS (-VE): 687.6 ($M^+$-H); HR-MS for $C_{37}H_{45}N_4O_7P$: Cacld.: 687.2948; Found: 687.2958.

Compound 22a. To the solution of sodium hexamethyl disilylamide (1.0 M in THF, 3.33 ml, 3.33 mmol) at −78° C. was added via cannula a pre-cooled solution (−78° C.) of compound 8 (1.596 g, 3.024 mmol) in 10 ml of THF, the solution turned to be deep purple quickly. After stirring at −78° C. for 20 min, a pre-cooled (−78° C.) solution of trisyl azide (1.126 g, 3.628 mmol) was added via cannula, the resulting solution was stirred at −78° C. for 5 min, then the reaction was quenched by the addition of glacial acetic acid (0.95 g, 16.6 mmol) followed by the addition of potassium acetate in 15 ml of THF, the mixture was then raised to 30° C., stirred for additional 1.5 hr. 20 ml of saturated $NaHCO_3$ solution was added to the reaction mixture, and then THF was evaporated, the remained product was extracted with ethyl acetate, washed with brine, dried over $Na_2SO_4$. Concentration and purification by silica gel chromatography (hexanes and ethyl acetate, from 4:1 to 2:1) afforded 1.26 g of product 22a (73.3% of yield). NMR (in $CDCl_3$): 7.40~7.14 (9H, m), 6.23~6.08 (1H, ddd, J=8.31, 10.01, 17.09 Hz), 5.480 (1H, d, J=10.25 Hz), 5.289 (1H, d, J=18.06 Hz), 5.272 (1H, d, J=9.27 Hz), 4.902 (1H, dd, J=2.44, 8.06 Hz), 4.235 (1H, t, J=8.54 Hz), 4.040 (1H, dd, J=2.69, 8.79 Hz), 3.824 (1H, t, J=8.55 Hz), 3.008 (2H, d, J=21.24 Hz), 1.454 (9H, s). FAB-MS (+VE): 569 ($MH^+$), 513 ($M^+$-$C_4H_8$), 457 ($M^+$-$2C_4H_8$).

Compound 23a. To the solution of compound 22a (1.2356 mg, 2.17 mmol) in 32 ml of THF-$H_2O$ mixture (3:1) at 0° C. was added $H_2O_2$ (30%, 1.107 ml, 10.85 mmol) via a syringe over 1 min, this was followed by the addition of LiOH (182.4 mg, 4.34 mmol in 4.4 ml of water). After stirring at 0° C. for 1 hr, the reaction mixture was raised to 30° C., for additional 4 hr. 1.367 g of $Na_2SO_3$ (10.85 mmol) in 8.5 ml of water was added to destroy the remained hydrogen peroxide, and THF was evaporated at 30° C. The remained mixture was extracted with dichloromethane to remove the Evan's reagent, then the aqueous solution was poured into 54 ml of ice-cooled 0.2 M HCl solution, extracted with ethyl acetate, washed with ice-cooled water and brine, dried over $Na_2SO_4$, concentrated, and taken to dryness under high vacuum to give 841 mg (92% of yield) of product 23a as white foam. NMR (in $CDCl_3$): 7.218 (2H, d, J=7.81 Hz), 7.143 (2H, dd, J=2.44, 7.81 Hz), 6.208~6.060 (1H, m), 5.246 (1H, d, J=13.67 Hz), 5.245 (1H, J=16.60 Hz), 3.950 (1H, d, J=9.28 Hz), 3.849 (1H, t, J=9.27 Hz), 2.779 (2H, dd, J=12.21, 21.24 Hz), 1.406 (9H, s), 1.346 (9H, s). FAB-MS (-VE): 422 (M-H).

Compound 24a. To the solution of amine 18a (290 mg, 0.626 mmol) in 5 ml of dry DMF was added the pre-activated ester solution of 23a [Formed by the reaction of 23a (265 mg, 0.626 mmol), HOBt (84.7 mg, 0.626 mmol), and DIPCDI (79.1 mg, 0.626 mmol) in 5 ml of dry DMF, 10 min]. The resulting mixture was stirred at room temperature for 12 hr, then DMF was evaporated. The residue was dissolved in 50 ml of ethyl acetate, washed with saturated $NaHCO_3$ solution, water, and brine, dried over $Na_2SO_4$. Concentration and purification by silica gel chromatography (chloroform and methanol, from 20:1 to 9:1) afforded 363 mg (67% of yield) of product 24a as a foam.

Compound 25a. To the solution of compound 24a (363 mg, 0.412 mmol) in the mixture of THF-water (8 ml-0.5 ml) was added triphenyl phosphine (163 mg, 0.618 mmol, 1.5 eq), the resulting mixture was stirred at room temperature for 12 hr, then THF was evaporated and the residue was purified by chromatography (chloroform and methanol, from 100:0 to 9:1) to give compound 268 mg of 25a (77% of yield).

General Procedures employed in the following: Elemental analyses were obtained from Atlantic Microlab Inc., Norcross. Solvent was removed by rotary evaporation under reduced pressure and silica gel chromatography was performed using high performance silica gel (60 Å pore, 10μ particle size). Anhydrous solvents were obtained commercially and used without further drying. Analytical HPLC were conducted using a Vydac $C_{18}$ column (10 mm dia.×250 mm long; solvent A=0.1% aqueous TFA; solvent B=0.1% TFA in acetonitrile; flow rate=2 mL/min.).

(S)-4-Benzyl-3-(prop-2-enoyl)-1,3-oxazolidin-2-one (39). To a solution of acrylic acid (7) (8.2 mL; 120 mmol) and N-methyl morpholine (NM) (13.2 mL; 120 mmol) in anhydrous THF (100 mL) at −78° C. under argon was added pivaloyl chloride (14.8 mL; 120 mmol) and the mixture was stirred at −78° C. (1 h). To a separate round bottomed flask containing Evan's reagent, (S)-(−)-4-Benzyl-2-oxazolidine-one (38) (17.7 g; 100 mmol) in anhydrous THF (200 mL) at −78° C. under argon, was added n-BuLi, 1.6 M in hexanes (62 mL; 100 mmol) and the solution was stirred at −78° C. (30 min). To this was then added via cannula at −78° C., the suspension of acryloyl mixed anhydride, and the resulting mixture was stirred first at −78° C. (1.5 h) then at room temperature (2 h). The mixture was partitioned between saturated $NH_4Cl$/EtOAc and the combined organics were washed with brine, dried ($MgSO_4$) and taken to dryness to yield a syrup (27.6 g). Purification by silica gel chromatography (EtOAc in hexanes, from 0% to 50%) provided unreacted Evan's reagent (6.44 g) as well as product (39) as a white foam, which crystallized (7.16 g; 49% based on recovered starting material), mp 70-72° C. $^1$H NMR ($CDCl_3$) δ 7.61 (dd, 1H, J=10.7, 17.1 Hz), 7.49~7.26 (m, 5 Hz), 6.70 (dd, 1H, J=1.7, 17.1 Hz), 6.03 (dd, 1H, J=1.7, 10.2 Hz), 4.99~4.79 (m, 1H), 3.37~4.25 (m, 2H), 3.44 (dd, 1H, 3.0, 13.2 Hz), 2.92 (dd, 1H, J=9.8, 13.2 Hz). FABMS ($^+$VE, NBA) m/z 232 (MH$^+$). Anal. calcd for $C_{13}H_{13}NO_3$: C, 67.52; H, 5.67; N, 6.06. Found: C, 67.57; H, 5.82; N, 6.08.

Bis-(tert-butyl) ((4-bromophenyl)methyl)phosphonate (40). To a solution of di-tert-butyl phosphite (9.70 g; 50 mmol) in anhydrous THF (100 mL) at −78° C. under argon, was added n-BuLi, 1.6 M in hexanes (33.2 mL; 50 mmol) over 5 minutes and the solution was stirred first at −78° C. (30 minutes), then at 0° C. (30 minutes). To this was added a solution of 4-bromobenzyl bromide (12.5 g; 50 mmol) in anhydrous THF (20 mL) and the mixture was stirred at 0° C., then allowed to come to room temperature and stirred overnight. The mixture was partitioned between saturated aqueous $NH_4Cl$ and EtOAc; the combined organic extracts were washed with brine; dried ($MgSO_4$) and taken to dryness, yielding a light yellow crystalline solid (18.27 g). Purification by silica gel chromatography (EtOAc in hexanes; from 0% to 100%), provided 40 as a cream colored crystalline solid (15.21 g; 82% yield), mp 45° (soften), 48°-56° C. $^1$H NMR ($CDCl_3$) δ 7.42 (d, 2H J=8.3 Hz), 7.16 (dd, 2H J=2.4, 8.3 Hz), 2.99 (d, 2H J=21.5 Hz), 1.43 (s, 18 H). HR-FABMS ($^+$VE) m/z calcd. for $C_{15}H_{25}N_3O_3PBr$ (M$^+$): 3363.0725. Found: 3963.0735 (δ m=2.8 ppm). Anal. calcd for $C_{15}H_{24}BrO_3P$: C, 49.60; H, 6.66. Found: C, 50.20; H, 6.60.

3-(3-(4-((Bis-(tert-butyl)phosphono)methyl)phenyl)prop-2-enoyl)-4-(S)-benzyl-1,3-oxazolidin-2-one (41). A mixture of acrylamide 39 (1.48 g; 6.40 mmol), di-tert-butyl (4-bromobenzyl)phosphonate (40) (2.36 g; 6.40 mmol), Pd(OAc)$_2$ (72 mg; 0.032 mmol) and tri-o-toluyl phosphine (390 mg; 1.28 mmol) in a round bottom flask sealed with a rubber septum, was alternately evacuated and flushed with argon (3×), then to this was added NEt$_3$ (12 mL) and the mixture was heated with stirring at 85° C. (overnight). The resulting suspension was partitioned between ice-cold saturated $NH_4Cl$/EtOAc and the combined organics were washed with brine, dried ($MgSO_4$) and taken to dryness to yield a foam (3.73 g). Purification by silica gel chromatography (EtOAc in hexanes, from 20% to 100%) provided 41 as a crystalline solid (2.58 g, 79%). Recrystallization from ether: hexanes provided an analytical sample, mp 128-129° C. $^1$H NMR ($CDCl_3$) δ 7.98 (s, 2H), 7.66 (d, sH, J=8.1 Hz), 7.48-7.31 (m, 1H), 4.95-4.84 (m, 1H), 4.38-4.27 (m, 2H), 3.46 (dd, 1H, J=3.0 13.2 Hz), 3.15 (d, 2H, J=22.2 Hz), 2.94 (dd, 1H, J=9.4, 13.2 Hz), 1.52 (s, 18 Hz). FABMS ($^+$VE) m/z 514 (MH$^+$). Anal. calcd for $C_{28}H_{36}NO_6P$: C, 65.48; H, 7.07; N, 2.73. Found: C, 65.74; H, 7.06; N, 2.81.

3-(3-(4-((Bis-(tert-butyl)phosphono)methyl)phenyl)propanoyl)-4-(S)-benzyl-1,3-oxazolidin-2-one (42). A solution of 41 (6.48 g; 12.7 mmol) in absolute EtOH (50 mL) was hydrogenated over Pd black (200 mg) at 40 psi H$_2$ in a Parr apparatus (overnight). Additional Pd black was added (200 mg) and hydrogenation continued (overnight). Catalyst was removed by filtration and the filtrate was taken to dryness to yield a white crystalline solid, which was triturated with ether to provide a white solid. This was combined with additional product obtained by cooling the filtrate to −78° C., providing 42 as a combined total of 5.37 g (82% yield), mp 114-115° C. $^1$H NMR ($CDCl_3$) δ 7.43~7.34 (m, 4H), 7.27 (s, 5H), 4.80~4.66 (m, 1H), 4.28~4.23 (m, 2H), 3.40~3.30 (m, 3H), 3.15~3.05 (m, 4H), 2.84 (dd, 1H, J=9.4, 13.2 Hz), 1.53 (s, 18 Hz). FABMS ($^+$VE, NBA) m/z 516 (MH$^+$), 404 (MH$^+$-2C$_4$H$_8$). Anal. calcd for $C_{28}H_{38}NO_6P$: C, 65.23; H, 7.43; N, 2.72. Found: C, 64.94; H, 7.34; N, 2.79.

(3-(4-((Bis-(tert-butyl)phosphono)methyl)phenyl)propanoic acid (35). To a solution of 42 (1.0 g; 1.95 mmol) in THF (15 mL) with $H_2O$ (5 mL) at 0° C., was added aqueous $H_2O_2$, 30% w/w (1.10 mL; 9.74 mmol) dropwise, followed by dropwise addition of an ice-cold solution of LiOH.$H_2O$ (164 mg; 3.89 mmol) in $H_2O$ (10 mL), and the mixture was then stirred at 0° C. (4 h). The mixture was diluted with $H_2O$ (100 mL), washed with $CH_2Cl_2$, then the aqueous was cooled to ~0° C. and ice-cold 0.1 N HCl was added (~80 mL) and the mixture was then extracted with EtOAc. Combined organics were dried (MgSO$_4$) and taken to a syrup, which quickly crystallized to provide 35 as a white solid (563 mg; 81% yield), mp 101 (soften); 106-110° C. $^1$H NMR ($CDCl_3$) δ 7.28 (dd, 2H, J=2.1, 8.1 Hz), 7.21 (d, 2H, J=8.1 Hz), 3.09 (d, 2H, J=21.4 Hz), 3.02 (t, 2H, J=7.7 Hz), 2.72 (t, 2H, J=7.7 Hz), 1.49 (s, 18 Hz). FABMS ($^-$VE, NBA) m/z 355 (M−H). Anal. calcd for $C_{18}H_{29}O_5P$: C, 60.66; H, 8.20. Found: C, 60.90; H, 8.10.

3-(2-(S-Azido-3-(4-((bis-(tert-butyl)phosphono)methyl) phenyl)propanoyl)-4-(S)-benzyl-1,3-oxazolidin-2-one (43). To anhydrous THF (50 mL) at −78° C. under argon was added potassium bis(trimethylsilyl)amide, 0.5 M in toluene (29.0 mL; 14.5 mmol), followed via cannula, a pre-cooled (−78° C.) solution of 42 (6.20 g; 12.1 mmol) in anhydrous THF (50 mL), and the resulting violet solution was stirred at −78° C. (30 minutes). To this was added rapidly via cannula, a pre-cooled (−78° C.) solution of (2,4,5-tri-isopropyl)phenylsulfonyl azide (4.50 g; 14.5 mmol). The resulting yellow solution was stirred at −78° C. (2 minutes), quenched by addition of HOAc (3.8 mL; 66.6 mmol) followed by solid KOAc (4.87 g; 49.7 mmol). The mixture was stirred at room temperature (3.5 h), then partitioned between saturated NaHCO$_3$ in brine/ EtOAc; washed with saturated NaHCO$_3$ in brine; dried (MgSO$_4$) and taken to dryness to yield a yellow resin (8.66 g). Purification by silica gel chromatography (50% EtOAc in hexanes) provided 43 as a white foam (5.13 g, 77%). Crystallization from ether provided an analytical sample, mp 80° C. (soften); 115-117° C. $^1$H NMR (CDCl$_3$) δ 7.46~7.27 (m, 9H), 5.37 (dd, 1H, J=6.0, 9.0 Hz), 4.70~4.58 (m, 1H), 4.30~4.14 (m, 2H), 3.40 (dd, 1H, J=3.0, 13.2 Hz), 3.28 (dd, 1H, J=6.0, 13.2 Hz), 3.10 (d, 2H, J=21.4 Hz), 2.90 (dd, 1H, J=9.4, 13.2 Hz), 1.50 (s, 9H), 1.49 (s, 9H). FABMS ($^+$VE) m/z 557 (MH$^+$), 501 (MH$^+$-C$_4$H$_8$), 445 (M$^+$-2C$_4$H$_8$). Anal.

3-(2-(S)-Azido-3-(4-((bis-(tert-butyl)phosphono)methyl) phenyl)propanoic acid (34). To a solution of 43 (4.77 g; 8.60 mmol) in THF (40 mL) with H$_2$O (10 mL) at 0° C., was added aqueous H$_2$O$_2$, 30% w/w (4.88 mL; 43.0 mmol) dropwise, followed by dropwise addition of an ice-cold solution of LiOH.H$_2$O (722 mg; 17.2 mmol) in H$_2$O (40 mL), and the mixture was then stirred at 0° C. (2 h). To the solution was added Na$_2$SO$_3$ (5.42 g; 43.0 mmol) in H$_2$O (20 mL), then the mixture was diluted with brine (300 mL), washed with CH$_2$Cl$_2$, then the aqueous was cooled to ~0° C. and ice-cold 1.0 N HCl was added until the pH≦3, and the mixture was extracted with EtOAc. Combined organics were dried (MgSO$_4$) and solvent removed to provide 36 as a highly crystalline white solid (3.00 g; 88% yield), mp 68-72° C. $^1$H NMR (CDCl$_3$) δ 7.29 (brs, 4H), 4.24~4.14 (m, 1H), 3.25~3.00 (m, 4H), 1.49 (s, 9H), 1.44 (s, 9H). FABMS ($^-$VE) m/z 396 (M−H). HR-FABMS (NE, MCA, Gly) m/z calcd. for C$_{18}$H$_{27}$N$_3$O$_3$P (M−H): 396.1688. Found: 396.1667 (δ m=2.1 mmu; 5.3 ppm). [α]$_D$=$^+$14.1° (c 0.95, CHCl$_3$). Anal. calcd for C$_{18}$H$_{28}$N$_3$O$_5$P.¾H$_2$O: C, 52.61; H, 7.24; N, 10.23. Found: C, 52.63; H, 6.77; N, 10.36.

Determination of enantiomeric purity of analogue 34. Dipeptides 44 and 45 were prepared from protected azido acid 34 using Rink amide resin (0.4 meq/g, purchased from Bachem Corp., Torrance, Calif.) with Fmoc-protocols similar to those previously described. Fmoc-D,L-Leu and Fmoc-L-Leu-Rink amide resins were prepared by coupling the appropriate Fmoc-protected amino acides to Rink resin, with the resulting Fmoc-protected resins (12.5 mg) then being washed well with several 1 mL portions of N-methyl-2-pyrolidoinone (NMP). Fmoc amino protection was removed by treatment with 20% piperidine in NMP (0.5 mL, 2 minutes followed by 0.5 mL, 20 minutes). Resins were washed well with NMP (10×1 mL) then coupled overnight with a solution of active ester formed by reacting 12.5 μmol each of protected azido acid 34, 1-hydroxybenzotriazole (HOBt) and 1,3-diisopropylcarbodiimide (DIPCDI) in NMP (1.0 mL, 10 minutes). Resins were first washed with NMP (10×1 mL) and dichloromethane (10×1 mL), then dipeptides were cleaved from the resin using a mixture of trifluoroacetic acid (TFA, 1.80 mL) and H$_2$O (200 μl) (1 h), taken to dryness and analyzed by HPLC (linear gradient from 10% B to 90% B over 20 minutes). Retention times of diastereomeric peaks as determined using dipeptide 44 prepared from racemic D,L-leucine, indicated diastereomers eluting at 18.6 minutes and 19.1 minutes. Enantiomeric contamination of azido acid 34 was then determined by similar analysis of dipeptide 45, where diastereomeric contamination accounted for an area less than 3% of that observed for the major diastereomer. These results indicated greater than 94% enantiomeric purity.

Figure 10:
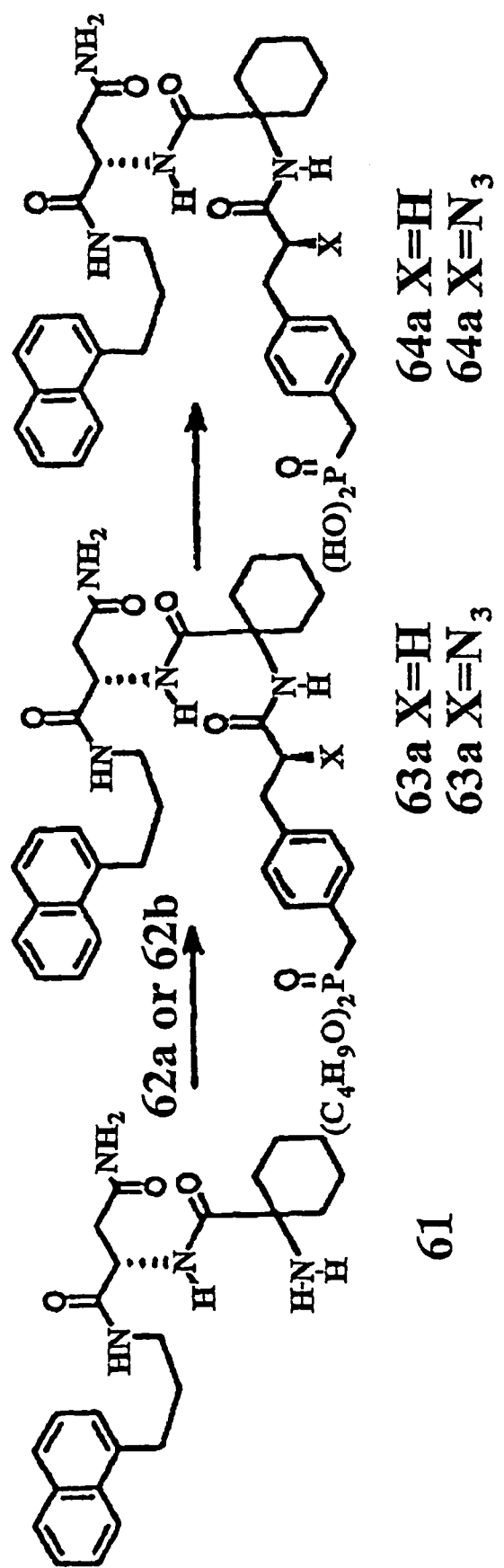
FIG. 10 depicts a method of preparing compounds 64a-b in accordance with an embodiment of the present invention.

Compounds 61-64 are illustrated in FIG. 10

Compound 63a. To a solution of amine 61 (85 mg; 0.20 mmol) in anhydrous DMF (1 mL) was added a preactivated ester solution formed by reacting des-amino Pmp 62a (71 mg; 0.20 mmol), HOBt (27 mg; 0.20 mmol), diisopropylcarbodiimide (DIPCDI) (31 μL; 0.20 mmol) in DMF (1 mL; 10 minutes). The mixture was stirred at room temperature (overnight) then taken to dryness under high vacuum and purified by silica gel chromatography (from 50% EtOAc in CHCl3 to 10% MeOH in EtOAc) to provide 63a as a white foam (118 mg; 77% yield). 1H NMR (CDCl3) d 8.20~8.10 (m, 2H), 7.94~7.84 (m, 2H), 7.80~7.72 (m, 1H), 7.58~7.48 (m, 2H), 7.45~7.38 (m, 2H), 7.23 (dd, 2H, J=1.7, 7.7 Hz), 7.10 (dd, 2H, J=7.7 Hz), 6.64 (brs, 1H), 6.28 (brs, 1H), 5.65 (brs, 1H), 4.86~4.75 (m, 1H), 3.54~3.35 (m, 2H), 3.25~3.15 (m, 4H), 3.06 (d, 2H, J=21.4 Hz), 3.00~2.87 (m, 2H), 2.70~2.50 (m, 4H), 2.35~1.25 (m, 12H), 1.50 (s, 18H). FABMS (+VE) m/z 763 (MH+). HR-FABMS (+VE, MCA, Gly) m/z calcd. for C42H60N4O7P M+H): 763.4200. Found: 763.4244 (Dm=4.4 mmu; 5.8 ppm).

Compound 64a. A solution of 63a (103 mg; 13.5 mmol) in TFA (1.9 mL): H2O (100 μL): triethylsilane (TES) (150 μL) was stirred at room temperature (1 h) then taken to dryness under high vacuum and purified by HPLC to provide 64a as a white solid (60 mg; 68% yield). Analytical HPLC (Vydac C18 Peptide and Protein column; 10 mm dia×250 mm long; flow rate=2 mL/min; solvent A=0.1% aqueous TFA, solvent B=0.1% TFA in acetonitrile; linear gradient 10% B-90% B over 20 minutes) retention time=21.7 minutes (>99%). 1H NMR (DMSO-d6) d 8.28~8.10 (m, 2H0, 7.97~7.92 (m, 1H), 7.84~7.76 (m, 1H), 7.74~7.66 (m, 1H), 7.58~7.48 (m, 2H), 7.46~7.42 (m, 2H), 7.16 (dd, 2H, J=1.7, 8.1 Hz), 7.03 (d, 2H, J=8.1 Hz), 4.45~4.37 (m, 1H), 3.27~3.17 (m, 2H), 3.15~3.05 (m, 4H), 2.94 (d, 2H, J=20.9 Hz), 2.85~2.68 (m, 4H), 2.13~1.10 (m, 12H). FABMS (−VE) m/z 649 (M−H). HR-FABMS (−VE, MCA, Gly) m/z calcd. for C34H42N4O7P (M−H): 649.279. Found: 649.2803 (Dm=1.2 mmu; 1.8 ppm).

Compound 63b. To a solution of amine 61 (85 mg; 0.20 mmol) in anhydrous DMF (1 mL) was added a preactivated ester solution formed by reacting azido Pmp 2b (79 mg; 0.20 mmol), HOBt (27 mg; 0.20 mmol), diisopropylcarbodiimide (DIPCDI) (31 μL; 0.20 mmol) in DMF (1 mL; 10 minutes). The mixture was stirred at room temperature (overnight) then taken to dryness under high vacuum and purified by silica gel chromatography (from 50% EtOAc in CHCl3 to 5% MeOH in EtOAc) to provide 63b as a white foam (94 mg; 58% yield). 1H NMR (CDCl$_3$) d 8.38 (d, 1H, J=7.7 Hz), 8.15 (d, 1H, J=8.1 Hz), 7.96~7.75 (m, 3H), 7.60~7.40 (m, 4H), 7.25~7.09 (m, 6H), 6.78 (brs, 1H), 5.65 (brs, 1H), 4.84~4.72 (m, 1H), 4.36~4.25 (m, 1H), 3.60~3.35 (m, 2H), 3.30~2.85 (m, 6H), 3.07 (d, 2H, I=21 Hz), 2.57 (dd, 1H, J=4.3, 9.0 Hz), 2.27~1.10 (m, 12H), 1.48 (s, 18H). FABMS (+VE, NBA) m/z 804 (MH+).

Compound 64b. A solution of 63b (47 mg; 58 μmol) in TFA (900 μL): H$_2$O (100 μL) was stirred at room temperature (1 h) then taken to dryness under high vacuum and purified by HPLC to provide 64b as a white solid (32 mg; 80% yield). Analytical HPLC (Vydac C18 Peptide and Protein column; 10 mm dia×250 mm long; flow rate=2 mL/min; solvent A=0.1% aqueous TFA, solvent B=0.1% TFA in acetonitrile; linear gradient 10% B-90% B over 20 minutes) retention time=22.8 minutes (>99%). 1H NMR (DMSO-d6) d 8.62 (s, 1H), 8.24 (d, 1H, J=7.7 Hz), 8.18~8.10 (m, 1H), 7.98~7.92 (m, 1H), 7.62~7.52 (m, 3H), 7.46~7.40 (m, 2H), 7.24 (dd, 2H, J=1.7, 8.1 Hz), 7.15 (d, 2H, J=8.1 Hz), 7.02 (s, 1H), 4.55~4.45

(m, 1H), 4.20 (dd, 1H, J 3.4, 10.7 Hz), 3.35~2.68 (m, 8H), 2.97 (d, 2H, J=21.4 Hz), 2.15~1.15 (m, 12H). FABMS (–VE, Gly) m/z 690 (M–H). HR-FABMS (–VE, MCA, Gly) m/z calcd. for C34H41N7O7P (M–H): 690.2805. Found: 690.2780 (Dm=2.5 mmu; 3.6 ppm).

General synthetic procedure for compounds 23a, 226, 236 and 242. To a solution of compound 22a, 125, 235, 241 (2.17 mmol) in 32 ml of THF-H$_2$O mixture (3:1) at 0° C. was added H$_2$O$_2$ (30%, 1.107 ml, 10.85 mmol) via a syringe over 1 min, this was followed by the addition of LiOH (182.4 mg, 4.34 mmol) in 4.4 ml of water. After stirring at 0° C. for 1 hr, the reaction mixture was raised to rt, for additional 6 hr. A solution of 1.367 g of Na$_2$SO$_3$ (10.85 mmol) in 8.5 ml of water was added to destroy the remained hydrogen peroxide, and THF was evaporated at 30° C. The remained mixture was extracted with DCM to remove the Evans' auxiliary, then the aqueous solution was acidified with 54 ml of ice-cooled 0.2M HCl solution, extracted with EtOAc, washed with brine, dried over Na$_2$SO$_4$, concentrated, and taken to dryness under high vacuum to give the title compounds.

General synthetic procedure for compounds 24a, 209-212, 217-120, 227-229, 237 and 244. To the solution of amine (0.626 mmol), acid (0.626 mmol), HOBt or HOAt (0.626 mmol) in 5 ml of dry DMF was added EDCI (0.688 mmol) at 0° C. The resulting mixture was stirred at room temperature for 12-24 hr, then DMF was evaporated. The residue was dissolved in 50 ml of ethyl acetate, washed with saturated NaHCO$_3$ solution, water, and brine, dried over Na$_2$SO$_4$. Concentration and purification by silica gel chromatography afforded the title compounds.

General procedure of RCM reaction to make compounds 221, 222, 230, 231 and 238. To the solution of compound 219, 220, 228, 229, 237 (0.518 mmol) in 150 ml of anhydrous dichloromethane (deoxygenized with Argon) was added via a syringe of Ruthenium catalyst (180 mg, 0.218 mmol) in 7 ml of dichloromethane, the solution was refluxed (60° C.) under Argon for 60 hr, monitored by T.L.C. Then, the solvent was evaporated, the residue was purified by silica gel chromatography to give the title compounds.

General hydrolysis procedure for making final products 223, 224, 232, 233, 239, 245 and 246. The tert-butyl protected analogues 221, 222, 230, 231, 238, 244 (0.2 mmol) was treated with a solution made of TFA-TES-H$_2$O (3.7 ml-0.1 ml-0.2 ml) at room temperature, after 1 hr, the solvents were evaporated. To the residue was added ether, a large amount of solid product precipitated, the product was separated by centrifuge, then washed with ether, separated by centrifuge again, the resulting solid product was dried under high vacuum to give crude product. The crude compound was dissolved in 16 ml of acetonitrile-water solution (1:1), purified by reversed-phase HPLC.

General procedure of making compounds 213-215, 18a. Compound 209-212 (1.0 mmol) was dissolved in 5 ml of acetonitrile. To the solution was added 1.0 ml of piperidine, the resulting solution was stirred at room temperature for 2 hr. The solvent was evaporated, the residue was purified by silica gel chromatography to give free amines.

(4S)-3-[(2S, 3R)-2-azido-3-(4-{[bis(tert-butoxy)phosphono]methyl}phenyl)pent-4-enoyl]-4-phenyl-1,3-oxazolidin-2-one (22a). To a solution of sodium hexamethyl disilylamide (1.0M in THF, 3.33 ml, 3.33 mmol) at –78° C. was added a pre-cooled solution (–78° C.) of compound 8a (1.596 g, 3.024 mmol) in 10 ml of THF, the solution became deep purple quickly. After stirring at –78° C. for 30 min, a pre-cooled (–78° C.) solution of trisyl azide 1.122 g, 3.628 mmol) was added, the resulting solution was stiffed at –78° C. for 5 min, then the reaction was quenched by the addition of glacial acetic acid (0.95 g, 16.6 mmol) followed by the addition of potassium acetate (1.217 g, 12.414 mmol), the mixture was then raised to 30° C., stirred for additional 1.5 hr. Then 20 ml of saturated aqueous NaHCO$_3$ solution was added to the reaction mixture, THF was evaporated, the remain was extracted with ethyl acetate, washed with brine, dried over Na$_2$SO$_4$. Concentration and purification by silica gel chromatography (Hexane and Ethyl acetate, from 4:1 to 2:1) afforded. 1.26 g of product 22a (73% of yield) as oil. $^1$H NMR (400 MHz, CDCl$_3$): δ 7.40~7.14 (9H, m), 6.15 (1H, m), 5.48 (1H, d, J=10.2 Hz), 5.29 (2H, dd, J=10.2, 17.0 Hz), 4.90 (1H, dd, J=2.8, 8.3 Hz), 4.24 (1H, t, J=8.5 Hz), 4.04 (1H, dd, J=2.7, 8.8 Hz), 3.82 (1H, t, J=8.5 Hz), 3.01 (2H, d, J=21.2 Hz), 1.46 (9H, s), 1.45 (9H, s); FAB-MS (+VE): 569 (MH$^+$), 513 (M$^+$-C$_4$H$_8$), 457 (M$^+$-2C$_4$H$_8$).

(2S, 3R)-2-azido-3-(4-{[bis(tert-butoxy)phosphono]methyl}phenyl)pent-4-enoic acid (23a). mp 125° C.; $^1$H NMR (400 MHz, CDCl$_3$): δ 7.22 (2H, d, J=7.8 Hz), 7.14 (2H, dd, J=2.4, 7.8 Hz), 6.16 (1H, m), 5.25 (2H, dd, J=13.7, 16.6 Hz), 3.95 (1H, d, J=9.3 Hz), 3.85 (1H, t, J=9.3 Hz), 2.78 (2H, dd, J=12.2, 21.2 Hz), 1.41 (9H, s), 1.35 (9H, s); FAB-MS (–VE): 422 (M$^+$–H).

N-{[N-((1S)-1-{N-[(2S)-2-(naphthylmethyl)pent-4-enyl]carbamoyl}-2-carbamoyleth yl)carbamoyl]cyclohexyl}(2S, 3R)-2-azido-3-(4-{[bis(tert-butoxy)phosphono]methyl}phenyl)pent-4-enamide (24a). mp 148-149° C.; $^1$H NMR (400 MHz, CDCl$_3$): δ 8.16 (1H, d, J=7.8 Hz), 8.01 (1H, dd, J=6.6, 14.8 Hz), 7.78 (1H, d, J=8.2 Hz), 7.65 (2H, m), 7.44 (1H, dt, J=1.4, 6.8 Hz), 7.38 (1H, dd, J=1.2, 7.0 Hz), 7.33 (2H, m), 7.14 (2H, m), 7.04 (1H, s), 7.02 (1H, s), 6.97 (1H, s), 6.49 (1H, s), 6.10 (1H, m), 5.83 (1H, m), 5.10 (4H, m), 4.58 (1H, m), 4.17 (1H, d, J=4.3 Hz), 3.93 (1H, dd, 4.1, 8.8 Hz), 3.23 (2H, dd, J=5.6, 5.8 Hz), 3.02 (2H, m), 2.96 (2H, d, J=21.4 Hz), 2.39 (1H, dd, J=5.1, 15.0 Hz), 2.10 (3H, m), 1.84 (2H, m), 1.74 (1H, m), 1.59 (3H, m), 1.39 (9H, s), 1.37 (9H, s), 1.23 (4H, m), 0.80 (1H, m); FAB-MS (+VE): 870 (MH$^+$), 814 (MH$^+$-C$_4$H$_8$), 758 (MH$^+$-2C$_4$H$_8$).

N-{[N-((1S)-1-{N-[(2S)-2-(naphthylmethyl)pent-4-enyl]carbamoyl}-2-carbamoyleth yl)carbamoyl]cyclohexyl}(2S, 3R)-2-amino-3-(4-{[bis(tert-butoxy)phosphono]methyl}phenyl)pent-4-enamide (25a). To the solution of compound 5 (363 mg, 0.418 mmol) in the mixture of THF-water (8 ml-0.5 ml) was added triphenyl phosphine (163 mg, 0.618 mmol, 1.5 eq), the resulting mixture was refluxed for 12 hr, then THF was evaporated, the aqueous solution was extracted with EtOAc, washed with brine, dried over Na$_2$SO$_4$. After removal of solvent, the residue was purified by silica gel chromatography (chloroform and methanol, from 100:0 to 9:1) to give compound 341 mg of 6 (97% of yield) as sticky oil. $^1$H NMR (400 MHz, CDCl$_3$): δ 8.12 (1H, m), 7.98 (2H, m), 7.77 (1H, d, J=7.8 Hz), 7.64 (1H, dd, J=4.7, 5.1 Hz), 7.43 (1H, dt, J=1.2, 6.6 Hz), 7.36 (1H, m), 7.32 (2H, m), 7.12 (2H, m), 7.02 (1H, s), 7.00 (1H, s), 6.68 (1H, s), 5.98 (1H, m), 5.79 (1H, m), 5.31 (1H, s), 5.08 (4H, m), 4.58 (1H, m), 3.87 (1H, m), 3.60 (1H, d, J=4.3 Hz), 3.21 (2H, t, J=5.5 Hz), 3.07 (1H, m), 2.97 (1H, m), 2.95 (2H, d, J=21.4 Hz), 2.38 (1H, dd, J=5.1, 14.8 Hz), 2.09 (3H, m), 1.87 (2H, m), 1.74 (1H, m), 1.57 (3H, m), 1.38 (9H, s), 1.37 (9H, s), 1.23 (4H, m), 0.77 (1H, m); FAB-MS (+VE): 844 (MH$^+$), 788 (MH$^+$-C$_4$H$_8$), 732 (MH$^+$-2C$_4$H$_8$).

N-{[N-((1S)-1-{N-[(2S)-2-(naphthylmethyl)pent-4-enyl]carbamoyl}-2-carbamoyleth yl)carbamoyl]cyclohexyl}(2S, 3R)-2-(acetylamino)-3-(4-{[bis(tertbutoxy)phosphono] methyl}phenyl)pent-4-enamide (20a). To the solution of compound 25a (84.3 mg, 0.1 mmol) in anhydrous DCM (10 ml) was added acetyl anhydride (0.189 ml, 2 mmol, 20 eq.) and triethyl amine (0.355 ml, 2.4 mmol, 24 eq.). The resulting mixture was stirred at rt for 12 hr. Aqueous NaHCO$_3$ was added to quench the reaction. The aqueous solution was extracted with DCM, washed with brine, dried over Na$_2$SO$_4$. After removal of solvent, the residue was purified by silica gel chromatography (chloroform and methanol, 9:1) to give 71 mg of 7 (80% of yield) as foam. $^1$H NMR (400 MHz, CDCl$_3$): δ 8.02 (1H, d, J=8.2 Hz), 7.80 (1H, d, J=7.8 Hz), 7.68 (1H, d, J=7.4 Hz), 7.46 (3H, m), 7.12 (2H, m), 7.02 (2H, m), 6.75 (1H, s), 6.67 (1H, s), 6.11 (1H, s), 5.80 (3H, m), 5.00 (4H, m), 4.64 (2H, m), 3.57 (1H, m), 3.35 (1H, m), 3.11 (1H, m), 3.04 (1H, m), 2.98 (1H, m), 2.93 (2H, d, J=21.4 Hz), 2.74 (1H, m), 2.60 (1H, m), 2.10 (3H, m), 1.83 (3H, s), 1.80 (2H, m), 1.63 (2H, m), 1.40 (9H, s), 1.37 (9H, s), 1.28 (2H, m), 1.09 (2H, m), 0.81 (1H, m), 0.74 (1H, m); FAB-MS (+VE): 886 (MH$^+$), 830 (MH$^+$-C$_4$H$_8$), 774 (MH$^+$-2C$_4$H$_8$).

(2S)-N-[(2S-2-(naphthylmethyl)pent-4-enyl]-2-(2-aminoacetylamino)-3-carbamoyl propanamide (213). mp 182° C.; $^1$H NMR (400 MHz, CD$_3$OD): δ 7.98 (1H, d, J=8.6 Hz), 7.78 (1H, d, J=8.8 Hz), 7.66 (1H, d, J=7.8 Hz), 7.46 (1H, m), 7.39 (1H, m), 7.29 (2H, m), 5.80 (1H, m), 5.01 (2H, m), 4.68 (1H, dd, J=6.1, 6.6 Hz), 3.25 (2H, m), 3.05 (2H, m), 2.97 (2H, m), 2.63 (2H, d, J=6.3 Hz), 2.06 (3H, m); FAB-MS (+VE): 397 (MH$^+$).

N-((1S)-1-{N-[(2S)-2-(naphthylmethyl)pent-4-enyl]carbamoyl}-2-carbamoylethyl)(2S,3R)-2-amino-3-methylpentanamide (214). mp 152-153° C.; $^1$H NMR (400 MHz, CD$_3$OD): δ 7.98 (1H, d, J=8.0 Hz), 7.80 (1H, d, J=8.4 Hz), 7.68 (1H, d, J=7.8 Hz), 7.48 (1H, m), 7.40 (1H, m), 7.31 (2H, m), 5.80 (1H, m), 5.02 (2H, m), 4.67 (1H, dd, J=6.4, 6.6 Hz), 3.25 (2H, m), 3.13 (2H, m), 2.98 (2H, m), 2.63 (2H, d, J=6.4 Hz), 2.07 (2H, m), 1.66 (1H, m), 1.40 (1H, m), 1.08 (1H, m), 0.87 (3H, d, J=6.8 Hz), 0.81 (3H, t, J=7.4 Hz); FAB-MS (+VE): 453 (MH$^+$).

N-((1S)-1-{N-[(2S)-2-(naphthylmethyl)pent-4-enyl]carbamoyl}-2-carbamoylethyl)2-amino-2-methylpropanamide (215). mp 89° C.; $^1$H NMR (400 MHz, CDCl$_3$): δ 8.80 (1H, d, J=7.0 Hz), 7.98 (1H, d, J=8.2 Hz), 7.85 (1H, m), 7.72 (1H, d, J=8.2 Hz), 7.49 (1H, m), 7.38 (1H, m), 7.31 (1H, d, J=7.0 Hz), 7.21 (1H, m), 6.29 (1H, s), 5.81 (1H, m), 5.54 (1H, s), 5.09 (2H, m), 4.61 (1H, m), 3.25 (2H, m), 3.06 (1H, dd, J=6.6, 14.0 Hz), 2.96 (1H, dd, J=6.6, 14.0 Hz), 2.80 (1H, dd, J=4.3, 15.2 Hz), 2.54 (1H, dd, J=7.0, 15.2 Hz), 2.11 (3H, d, J=6.2 Hz), 1.36 (3H, s), 1.34 (3H, s); FAB-MS (+VE): 425 (MH$^+$).

(2S)-N-[(2S)-2-(naphthylmethyl)pent-4-enyl]-2-[(aminocyclohexyl)carbonylamino]-3-carbamoylpropanamide (18a). $^1$H NMR (400 MHz, CDCl$_3$): δ 8.89 (1H, d, J=6.8 Hz), 7.98 (1H, m), 7.85 (1H, m), 7.72 (1H, d, J=7.8 Hz), 7.55~7.26 (7H, m), 6.31 (1H, s, br.), 5.91~5.75 (1H, m), 5.54 (1H, s, br.), 5.13~5.07 (2H, m), 4.68 (1H, dd, J=6.1, 10.7 Hz), 3.35~3.21 (2H, m), 3.08 (1H, dd, J=6.6, 14.2 Hz), 2.97 (1H, dd, J=6.4, 13.9 Hz), 2.83 (1H, dd, J=4.4, 15.1 Hz), 2.56 (1H, dd, J=6.5, 14.6 Hz), 2.17 (2H, d, J=5.9 Hz), 2.05~1.23 (11H, m). FAB-MS (+VE): 465 (MH$^+$).

(3R)-N-{[N-((1S)-1-{N-[(2S)-2-(naphthylmethyl)pent-4-enyl]carbamoyl}-2-carbamo ylethyl)carbamoyl]methyl}-3-(4-{[bis(tert-butoxy)phosphonolmethyl]phenyl)pent-4-enamide (217). mp 120° C.; $^1$H NMR (400 MHz, CDCl$_3$): δ 7.95 (1H, d, J=8.4 Hz), 7.78 (1H, dd, J=1.3, 8.1 Hz), 7.66 (1H, d, J=7.9 Hz), 7.61 (1H, d, J=7.9 Hz), 7.43 (2H, m), 7.29 (2H, m), 7.12 (1H, d, J=2.4 Hz), 7.09 (1H, d, J=2.4 Hz), 7.01 (1H, s), 6.98 (1H, s), 6.90 (1H, m), 6.78 (1H, s), 5.81 (2H, m), 5.71 (1H, s), 5.03 (2H, m), 4.93 (2H, m), 4.68 (1H, dd, J=7.1, 12.4 Hz), 3.75 (1H, m), 3.65 (2H, m), 3.28 (1H, m), 3.07 (1H, m), 2.97 (2H, m), 2.93 (2H, d, J=21.4 Hz), 2.70 (1H, dd, J=4.9, 15.9 Hz), 2.52 (3H, m), 2.06 (3H, m), 1.37 (9H, s), 1.35 (9H, s); FAB-MS (+VE): 761 (MH$^+$), 705 (MH$^+$-C$_4$H$_8$), 649 (MH$^+$-2C$_4$H$_8$).

(3R)-N-{[N-((1S)-1-{N-[(2S-2-(naphthylmethyl)pent-4-enyl]carbamoyl}-2-carbamo ylethyl)carbamoyl](1S,2R)-2-methylbutyl}-3-(4-{[bis(tert-butoxy)phosphono] methyl}phenyl)pent-4-enamide (218). mp 175-176° C.; $^1$H NMR (400 MHz, CD$_3$OD): δ 7.98 (1H, d, J=8.2 Hz), 7.79 (1H, dd, J=1.2, 8.6 Hz), 7.65 (1H, dd, J=2.3, 7.4 Hz), 7.43 (1H, m), 7.38 (1H, m), 7.29 (2H, m), 7.10 (1H, d, J=2.3 Hz), 7.08 (1H, d, J=2.3 Hz), 7.00 (1H, s), 6.97 (1H, s), 5.82 (2H, m), 5.00 (2H, m), 4.89 (2H, m), 4.55 (1H, t, J=6.2 Hz), 3.98 (1H, d, J=7.0 Hz), 3.66 (1H, dd, J=7.4, 15.6 Hz), 3.19 (1H, dd, J=6.6, 13.6 Hz), 3.02 (1H, m), 2.97 (1H, m), 2.95 (2H, d, J=21.4 Hz), 2.63 (3H, m), 2.50 (1H, dd, J=6.2, 14.0 Hz), 2.10 (2H, m), 1.99 (1H, m), 1.74 (1H, m), 1.42 (1H, m), 1.38 (9H, s), 1.34 (9H, s), 1.13 (1H, m), 0.81 (6H, m), 0.69 (1H, m); FAB-MS (+VE): 817 (MH$^+$), 761 (MH$^+$-C$_4$H$_8$), 705 (MH$^+$-2C$_4$H$_8$).

(3R)-N-{[N-((1S)-1-{N-[(2S)-2-(naphthylmethyl)pent-4-enyl]carbamoyl}-2-carbamo ylethyl)carbamoyl]-isopropyl}-3-(4-{[bis(tert-butoxy)phosphono]methyl}phenyl) pent-4-enamide (219). mp 108-110° C.; $^1$H NMR (400 MHz, CDCl$_3$): δ 8.04 (1H, d, J=8.2 Hz), 7.80 (2H, m), 7.69 (2H, m), 7.44 (2H, m), 7.34 (2H, m), 7.13 (1H, d, J=2.7 Hz), 7.11 (1H, d, J=2.7 Hz), 6.96 (1H, s), 6.94 (1H, s), 6.79 (1H, s), 6.51 (1H, s), 5.84 (2H, m), 5.58 (1H, s), 5.05 (2H, m), 4.95 (2H, m), 4.62 (1H, m), 3.71 (1H, dd, J=7.0, 14.0 Hz), 3.32 (1H, m), 3.10 (2H, m), 3.00 (1H, m), 2.96 (1H, m), 2.96 (2H, d, J=21.4 Hz), 2.90 (1H, m), 2.54 (2H, m), 2.45 (1H, dd, J=5.1, 15.2 Hz), 2.23 (1H, m), 2.10 (2H, m), 1.41 (9H, s), 1.39 (9H, s), 1.36 (3H, s), 1.32 (3H, s); FAB-MS (+VE): 789 (MH$^+$), 733 (MH$^+$-C$_4$H$_8$), 677 (MH$^+$-2C$_4$H$_8$).

(3R)-N-{[N-((1S)-1-{N-[(2S)-2-(naphthylmethyl)pent-4-enyl]carbamoyl}-2-carbamo-ylethyl)carbamoyl]cyclohexyl}-3-(4{[bis(tert-butoxy)phosphono]methyl}phenyl) pent-4-enamide (220). mp 87-88° C.; $^1$H NMR (400 MHz, CDCl$_3$): δ 8.05 (1H, d, J=8.1 Hz), 7.85~7.64 (4H, m), 7.55~7.38 (4H, m), 7.15 (2H, dd, J=2.4, 7.8 Hz), 6.99 (2H, d, J=, 8.1 Hz), 6.28 (1H, s, br.), 5.96~5.77 (3H, m), 5.41 (1H, s, br.), 5.13~4.90 (4H, m), 4.72 (1H, m), 3.73 (1H, m), 3.37 (1H, m), 3.22~2.91 (6H, m), 2.65~2.45 (2H, m), 2.30~2.01 (3H, m), 1.95~1.09 (11H, m), 1.43 (9H, s), 1.41 (9H, s); FAB-MS (+VE): 828 (M$^+$), 772 (M$^+$-C$_4$H$_8$), 716 (M$^+$-2C$_4$H$_8$).

2-[(1S, 5S, 9R)-3, 12, 15-triaza-9-(4-{[bis(tert-butoxy)phosphono]methyl}phenyl)-13,13-dimethyl-5-(naphthylmethyl)-2,11,14-trioxocyclopentadec-7-enyl]acetamide (221). mp 218° C.; $^1$H NMR (400 MHz, CD$_3$OD): δ 8.78 (1H, s), 8.48 (1H, d, J=8.2 Hz), 8.14 (1H, d, J=8.5 Hz), 7.78 (1H, dd, J=1.2, 8.2 Hz), 7.74 (1H, m), 7.65 (1H, d, J=7.6 Hz), 7.48 (1H, m), 7.40 (1H, m), 7.30 (2H, m), 7.12 (2H, m), 5.61 (1H, m), 5.39 (1H, m), 4.50 (1H, m), 3.82 (1H, m), 3.72 (1H, dd, J=6.6, 13.0 Hz), 3.28 (1H, m), 2.98 (1H, m), 2.96 (2H, d, J=21.4 Hz), 2.78 (1H, m), 2.63 (2H, m), 2.46 (2H, m), 2.20 (1H, m), 1.98 (1H, m), 1.80 (1H, m), 1.45 (3H, s), 1.37 (3H, s), 1.35 (18H, s); FAB-MS (+VE): 761 (M$^+$), 705 (M$^+$-C$_4$H$_8$), 649 (M$^+$-2C$_4$H$_8$).

2-[(9S, 13S, 17R)-8, 11, 20-triaza-17-(4-{[bis(tert-butoxy)phosphono]methyl}phenyl)-13-(naphthylmethyl)-7, 10, 19-trioxospiro[5.14]icos-15-en-9-yl]acetamide (222). mp 210° C.; $^1$H NMR (400 MHz, CDCl$_3$): δ 8.30~8.00 (2H, m), 7.83 (1H, m), 7.69 (1H, d, J=7.8 Hz), 7.59 (1H, m), 7.55~7.30 (4H, m), 7.25~7.05 (4H, m), 6.35 (1H, s, br.), 6.28 (1H, s, br.), 5.66 (1H, dd, J=9.3, 14.4 Hz), 5.31 (1H, m), 5.08 (1H, s, br.), 4.66 (1H, m), 3.90~3.70 (2H, m), 3.62 (1H, m), 3.33~3.08 (2H, m), 3.06~2.88 (4H, m), 2.85~2.50 (4H, m), 2.37~1.15 (11H, m), 1.42 (18H, s); FAB-MS (+VE): 801 (MH$^+$), 745 (MH$^+$-C$_4$H$_8$), 689 (MH$^+$-2C$_4$H$_8$).

2-{(1S, 5S, 9R)-3, 12, 15-triaza-13, 13-dimethyl-5-(naphthylmethyl)-2, 11, 14-trioxo-9-[4-(phosphonomethyl)phenyl] cyclopentadec-7-enyl]acetamide (223). mp 230° C. (dec.); $^1$H NMR (400 MHz, CD$_3$OD): δ 8.79 (1H, s), 8.48 (1H, d, J=8.0 Hz), 8.14 (1H, d, J=8.4 Hz), 7.78 (1H, d, J=7.8 Hz), 7.74 (1H, m), 7.64 (1H, d, J=7.4 Hz), 7.48 (1H, t, J=7.0 Hz), 7.40 (1H, t, J=7.4 Hz), 7.28 (2H, m), 7.14 (4H, m), 5.60 (1H, m), 5.37 (1H, m), 4.50 (1H, m), 3.80 (1H, dd, J=10.1, 10.7 Hz), 3.72 (1H, dd, J=6.3, 13.7 Hz), 3.31 (1H, m), 3.02 (2H, d, J=21.3 Hz), 2.97 (1H, m), 2.78 (1H, m), 2.65 (1H, dd, J=10.1, 13.5 Hz), 2.58 (1H, dd, J=2.3, 12.5 Hz), 2.49 (1H, dd, J=4.7, 15.2 Hz), 2.42 (1H, dd, J=12.3, 12.5 Hz), 2.19 (1H, m), 1.95 (1H, m), 1.78 (1H, m), 1.46 (3H, s), 1.36 (3H, s); FAB-MS (−VE): 647 (M$^+$−H).

2-[(9S, 13S, 17R)-8, 11, 20-triaza-13-(naphthylmethyl)-7, 10, 19-trioxo-17-[4-(phosphonomethyl)phenyl]spiro[5.14] icos-15-en-9-yl]acetamide (224). mp 225° C. (dec.); $^1$H NMR (400 MHz, d$^6$-DMSO): δ 8.40 (1H, s), 8.23 (1H, d, J=7.8 Hz), 8.12 (1H, d, J=8.1 Hz), 7.89 (1H, d, J=7.6 Hz), 7.75 (1H, m), 7.56~7.38 (6H, m), 7.15~7.02 (5H, m), 5.55 (1H, dd, J=9.5, 14.2 Hz), 5.37 (1H, m), 4.27 (1H, m), 3.86 (1H, m), 3.59 (1H, dd, J=5.6, 11.7 Hz), 3.16 (1H, dd, J=5.7, 14.4 Hz), 2.95~2.30 (8H, m), 2.25~1.10 (13H, m); FAB-MS (−VE): 687.6 (M$^+$−H); FAB-HRMS for C$_{37}$H$_{44}$N$_4$O$_7$P (M$^+$−H) cacld.: 687.2948; found: 687.2958.

tert-Butyl 3-[((4S)-2-oxo-4-phenyl(1, 3-oxazolidin-3-yl)) carbonyl](3S, 4S)-4-(4-([bis(tert-butoxy)phosphono]methyl)phenyl)hex-5-enoate (225). To a solution of sodium hexamethyl disilylamide (1.0M in THF, 1.2 ml, 1.2 mmol) at −78° C. was added a solution of compound 8a (527 mg, 1.0 mmol) in 2 ml of THF, the solution became deep purple quickly. After stirring at −78° C. for 30 min, a pre-cooled (−78° C.) solution of tert-butyl bromoacetate (234 mg, 1.2 mmol) was added, the resulting solution was stirred at −78° C. for 2 h, then raised to rt, stirred overnight. Then 20 ml of saturated aqueous NH$_4$Cl solution was added to quench the reaction mixture, THF was evaporated, the remaining was extracted with ethyl acetate, washed with brine, dried over Na$_2$SO$_4$. Concentration and purification by silica gel chromatography (Hexane and Ethyl acetate, 1:1.25) afforded 495 mg of product 225 (77% of yield) as oil. $^1$H NMR (400 MHz, CDCl$_3$): δ 7.30-7.15 (9H, m), 6.08 (1H, m), 5.18 (2H, m), 4.80 (2H, m), 4.04 (1H, dd, J=8.1, 8.6 Hz), 3.95 (1H, dd, J=2.4, 8.6 Hz), 3.35 (1H, t, J=9.8 Hz), 3.02 (2H, d, J=21.5 Hz), 2.77 (1H, dd, J=11.0, 17.1 Hz), 2.61 (1H, dd, J=3.9, 17.1 Hz), 1.49 (18H, s), 1.31 (9H, s); FAB-MS (+VE): 642 (MH$^+$), 586 (MH$^+$-C$_4$H$_8$), 530 (MH$^+$-2C$_4$H$_8$), 474 (MH$^+$-3C$_4$H$_8$).

(2S,3S)-3-(4-{[bis(tert-butoxy)phosphono]methyl}phenyl)-2-{[(tert-butyl)oxycarbon yl]methyl}pent-4-enoic acid (226). mp 155° C.; $^1$H NMR (400 MHz, CDCl$_3$): δ 7.16 (4H, m), 5.97 (1H, m), 5.15 (2H, m), 3.50 (1H, t, J=9.3 Hz), 3.15 (1H, dt, J=4.4, 9.8 Hz), 2.83 (2H, dd, J=3.4, 21.5 Hz), 2.60 (2H, m), 1.43 (9H, s), 1.41 (9H, s), 1.37 (9H, s); FAB-MS (−VE): 495 (M$^+$−H), 439 (M$^+$−H—C$_4$H$_8$).

tert-Butyl 3-(N-{[N-((1S)-1-{N-[(2S)-2-(naphthylmethyl) pent-4-enyl]carbamoyl}-2-carbamoylethyl)carbamoyl] methyl}carbamoyl)(3S,4S)-4-(4-{(bis(tert-butoxy)phos phonolmethyl}phenyl)hex-5-enoate (227). mp 104-105° C.; $^1$H NMR (400 MHz, CDCl$_3$): δ 7.97 (1H, d, J=8.5 Hz), 7.80 (1H, dd, J=1.4, 8.2 Hz), 7.68 (1H, d, J=7.9 Hz), 7.45 (2H, m), 7.34 (3H, m), 7.12 (3H, m), 7.05 (1H, s), 7.03 (1H, s), 6.40 (1H, s), 5.79 (2H, m), 5.60 (1H, s), 5.04 (4H, m), 4.61 (1H, dd, J=6.4, 13.0 Hz), 3.59 (1H, dd, J=5.4, 16.7 Hz), 3.33 (3H, m), 3.13 (1H, m), 3.00 (2H, d, J=6.7 Hz), 2.92 (2H, d, J=21.5 Hz), 2.86 (1H, dt, J=3.7, 10.1 Hz), 2.70 (2H, m), 2.58 (1H, m), 2.49 (1H, dd, J=3.8, 17.1 Hz), 2.12 (3H, m), 1.37 (9H, s), 1.35 (9H, s), 1.34 (9H, s); FAB-MS (+VE): 875 (MH$^+$), 819 (MH$^+$-C$_4$H$_8$), 763 (MH$^+$-2C$_4$H$_8$), 707 (MH$^+$-3C$_4$H$_8$).

tert-Butyl 3-(N-{1-[N-((1S)-1-{N-[(2S)-2-(naphthylmethyl) pent-4-enyl]carbamoyl}-2-carbamoylethyl)carbamoyl]-isopropyl}carbamoyl)(3S,4S)-4-(4-{[bis(tert-butoxy) phosphono]methyl}phenyl)hex-5-enoate (228). mp 92° C.; $^1$H NMR (400 MHz, CDCl$_3$): δ 8.04 (1H, d, J=8.5 Hz), 7.80 (1H, dd, J=1.3, 8.5 Hz), 7.68 (1H, m), 7.48 (1H, m), 7.42 (1H, m), 7.35 (3H, m), 7.10 (2H, m), 7.00 (1H, m), 6.91 (1H, s), 6.89 (1H, s), 6.63 (1H, s), 6.00 (1H, m), 5.84 (1H, m), 5.66 (1H, m), 5.38 (1H, s), 5.05 (2H, m), 4.92 (2H, m), 4.45 (1H, dd, J=6.2, 13.0 Hz), 3.29 (1H, m), 3.11 (2H, m), 3.04 (2H, m), 2.92 (2H, d, J=21.4 Hz), 2.78 (2H, m), 2.66 (1H, dd, J=7.5, 15.2 Hz), 2.48 (2H, d, J=7.0 Hz), 2.16 (2H, m), 2.06 (1H, m), 1.39 (9H, s), 1.37 (9H, s), 1.35 (9H, s), 1.14 (3H, s), 1.04 (3H, s); FAB-MS (+VE): 903 (MH$^+$), 847 (MH$^+$-C$_4$H$_8$), 791 (MH$^+$-2C$_4$H$_8$), 735 (MH$^+$-3C$_4$H$_8$).

tert-Butyl 3-(N-{[N-((1S)-1-{N-[(2S)-2-(naphthylmethyl) pent-4-enyl]carbamoyl}-2-carbamoylethyl)carbamoyl]-cyclohexyl}carbamoyl)(3S,4S)-4-(4-{[bis(tert-butoxy) phosphonolmethyl}phenyl)hex-5-enoate (229). mp 85° C.; $^1$H NMR (400 MHz, CDCl$_3$): δ 8.05 (1H, d, J=8.4 Hz), 7.81 (1H, d, J=8.5 Hz), 7.68 (1H, dd, J=2.6, 6.6 Hz), 7.45 (2H, m), 7.36 (3H, m), 7.09 (2H, m), 6.90 (1H, s), 6.88 (1H, s), 6.74 (1H, s), 6.06 (1H, s), 5.84 (1H, m), 5.61 (1H, m), 5.38 (1H, s), 5.07 (2H, m), 4.90 (2H, m), 4.57 (1H, dd, J=7.4, 12.5 Hz), 3.32 (1H, m), 3.20 (1H, dd, J=10.0, 10.4 Hz), 3.04 (2H, m), 2.93 (4H, m), 2.74 (1H, m), 2.62 (1H, m), 2.46 (2H, m), 2.18 (2H, m), 2.08 (1H, m), 1.70 (6H, m), 1.40 (9H, s), 1.38 (9H, s), 1.36 (9H, s), 1.05 (3H, m), 0.78 (1H, m); FAB-MS (+VE): 943 (MH$^+$), 887 (MH$^+$-C$_4$H$_8$), 831 (MH$^+$-2C$_4$H$_8$), 775 (MH$^+$-3C$_4$H$_8$).

tert-Butyl 2-[(1S, 7S, 11S, 15S)-3, 6, 9-triaza-15-(4-{[bis (tert-butoxy)phosphono]methyl}phenyl)-7-(carbamoylmethyl)-4,4-dimethyl-11-(naphthylmethyl)-2,5,8-trioxo cyclopentadec-13-enyl]acetate (230). mp 229-230° C.; $^1$H NMR (400 MHz, CD$_3$OD): δ 8.88 (1H, s), 8.50 (1H, d, J=8.5 Hz), 8.18 (1H, d, J=8.5 Hz), 7.78 (1H, dd, J=1.2, 8.2 Hz), 7.66 (2H, m), 7.48 (1H, m), 7.40 (1H, m), 7.32 (2H, m), 7.18 (3H, m), 5.84 (1H, m), 5.20 (1H, m), 5.20 (1H, m), 2.0, 10.4, 12.3 Hz), 5.45 (1H, ddd, J=3.1, 10.5, 14.2 Hz), 4.53 (1H, m), 3.98 (1H, d, J=10.3 Hz), 3.72 (1H, dd, J=6.9, 13.2 Hz), 3.34 (1H, dd, J=4.4, 13.3 Hz), 3.05 (1H, dt, J=12.4, 2.3 Hz), 3.00 (2H, d, J=21.4 Hz), 2.98 (1H, m), 2.80 (2H, m), 2.67 (1H, dd, J=10.2, 13.6 Hz), 2.47 (1H, dd, J=4.8, 15.2 Hz), 2.22 (1H, m), 2.03 (2H, m), 1.94 (1H, m), 1.418 (3H, s), 1.412 (3H, s), 1.352 (9H, s), 1.348 (9H, s), 1.32 (9H, s);

tert-Butyl 2-[(9S, 10S, 14S, 18S)-7, 16, 19-triaza-10-(4-{[bis (tert-butoxy)phosphono]methyl}phenyl)-18-(carbamoylmethyl)-14-(naphthylmethyl)-8,17,20-trioxospiro[5.14]icos-11-en-9-yl]acetate (231). mp 221° C.; $^1$H NMR (400 MHz, CDCl$_3$): δ 8.12 (1H, d, J=8.5 Hz), 8.04 (1H, d, J=7.9 Hz), 7.74 (1H, d, J=8.4 Hz), 7.64 (1H, d, J=7.9 Hz), 7.49 (1H, m), 7.44

(1H, m), 7.34 (2H, m), 7.25 (1H, m), 7.14 (4H, m), 6.36 (1H, s), 6.05 (1H, s), 5.74 (1H, dd, J=10.1, 14.1 Hz), 5.26 (1H, m), 4.98 (1H, s), 4.63 (1H, m), 3.92 (1H, d, J=9.4 Hz), 3.74 (1H, dd, J=6.1, 13.8 Hz), 3.27 (1H, dd, J=5.0, 13.8 Hz), 3.09 (1H, m), 3.00 (1H, m), 2.95 (2H, d, J=21.4 Hz), 2.81 (1H, dd, J=11.8, 17.3 Hz), 2.72 (1H, m), 2.64 (1H, dd, J=9.7, 13.8 Hz), 2.25 (2H, m), 2.10 (3H, m), 1.88 (1H, m), 1.70 (6H, m), 1.52 (3H, m), 1.35 (9H, s), 1.34 (9H, s), 1.30 (9H, s); FAB-MS (+VE): 915 (MH$^+$), 859 (MH$^+$-C$_4$H$_8$), 803 (MH$^+$-2C$_4$H$_8$), 747 (MH$^+$-3C$_4$H$_8$).

2-{(1S, 7S, 11S, 15S)-3, 6, 9-triaza-7-(carbamoylmethyl)-4, 4-dimethyl-11-(naphthylmethyl)-2, 5, 8-trioxo-15-[4-(phosphonomethyl)phenyl]cyclopentadec-13-enyl]acetic acid (232). mp 240° C. (dec.); $^1$H NMR (400 MHz, CD$_3$OD): δ 8.86 (1H, s), 8.48 (1H, d, 8.2 Hz), 8.18 (1H, d, J=8.6 Hz), 7.78 (1H, d, J=7.6 Hz), 7.68 (2H, m), 7.48 (1H, dd, J=6.8, 7.4 Hz), 7.40 (1H, t, J=7.6 Hz), 7.32 (2H, m), 7.20 (3H, s), 5.85 (1H, m), 5.44 (1H, m), 4.53 (1H, m), 3.97 (1H, d, J=9.4 Hz), 3.72 (1H, dd, J=7.2, 13.3 Hz), 3.34 (1H, m), 3.10 (1H, m), 3.02 (2H, d, J=21.3 Hz), 2.97-2.77 (3H, m), 2.68 (1H, m), 2.48 (1H, dd, J=4.7, 15.0 Hz), 2.22 (1H, m), 2.15 (1H, d, J=15.4 Hz), 2.02 (1H, m), 1.94 (1H, m), 1.414 (3H, s), 1.407 (3H, s); FAB-MS (–VE): 705 (M$^+$–H).

2-[(9S, 10S, 14S, 18S)-7, 16, 19-triaza-18-(carbamoylmethyl)-14-(naphthylmethyl)-8,17,20-trioxo-10-[4-(phosphonomethyl)phenyl]spiro[5.14]icos-11-en-9-yl]acetic acid (233). mp 260° C. (dec.); $^1$H NMR (400 MHz, CD$_3$OD): δ 8.64 (1H, s), 8.48 (1H, d, 7.9 Hz), 8.16 (1H, d, J=8.3 Hz), 7.78 (1H, d, J=7.9 Hz), 7.66 (1H, d, J=9.1 Hz), 7.60 (1H, t, J=6.3 Hz), 7.48 (1H, t, J=7.0 Hz), 7.40 (1H, dd, J=6.9, 7.8 Hz), 7.32 (2H, m), 7.22 (3H, m), 5.84 (1H, dd, J=11.1, 13.7 Hz), 5.40 (1H, m), 4.49 (1H, m), 4.04 (1H, d, J=9.4 Hz), 3.72 (1H, dd, J=6.7, 13.9 Hz), 3.37 (2H, m), 3.02 (2H, d, J=21.7 Hz), 2.96 (1H, dd, J=4.5, 15.2 Hz), 2.88 (1H, m), 2.82 (1H, m), 2.68 (1H, dd, J=10.1, 13.8 Hz), 2.45 (1H, dd, J=4.8, 15.2 Hz), 2.28-1.90 (6H, m), 1.80 (2H, m), 1.58 (5H, m), 1.26 (1H, m); FAB-MS (–VE): 745 (M$^+$-H); FAB-HRMS for C$_{39}$H$_{46}$N$_4$O$_9$P (M$^+$–H) cacld.:; found:.

(4S)-3-[(3S)-3-(4-{[bis(tert-butoxy)phosphono] methyl}phenyl)hex-5-enoyl]4-phenyl-1,3-oxazolidin-2-one (235). mp 150° C.; To a slurry of CuBr.Me$_2$S complex (309 mg, 1.5 mmol) in 10 ml of dry THF at –78° C. was added a solution of allylmagnesium bromide in Et$_2$O (1.0 M, 3 ml, 3.0 mmol) dropwise, the resulting mixture was stir at –78° C. for 10 min. To the mixture was added a pre-cooled (–78° C.) solution of compound 234 (499.5 mg, 1.0 mmol) in 5 ml of anhydrous THF dropwise, the reaction mixture was stirred at –78° C. for 2 hr (the reaction was monitored by TLC, till the starting material disappeared). The reaction mixture was poured into ice-cooled NH$_4$Cl solution, the solid was removed by filtration. After evaporation of THF, the residue was extracted with ethyl acetate, washed with water, saturated brine, and dried over Na$_2$SO$_4$. Concentration and purification by silica gel chromatography afforded 449 mg of product 235 as white solid (83% of yield). $^1$H NMR (400 MHz, CDCl$_3$): δ 7.36 (3H, m), 7.26 (2H, m), 7.15 (4H, m), 5.58 (1H, m), 5.26 (1H, dd, J=3.4, 8.5 Hz), 4.91 (2H, m), 4.54 (1H, t, J=8.6 Hz), 4.23 (1H, dd, J=3.4, 8.8 Hz), 3.47 (1H, dd, J=8.5, 15.9 Hz), 3.20 (2H, m), 3.00 (2H, d, J=21.2 Hz), 2.35 (2H, t, J=6.6 Hz), 1.42 (18H, s); FAB-MS (+VE): 542 (MH$^+$), 486 (MH$^+$-C$_4$H$_8$), 430 (MH$^+$-2C$_4$H$_8$).

(3S)-3-(4-{[bis(tert-butoxy)phosphono]methyl}phenyl)hex-5-enoic acid (236). mp 89-90° C.; $^1$H NMR (400 MHz, CDCl$_3$): δ 7.15 (4H, m), 5.65 (1H, m), 4.97 (2H, m), 3.20 (1H, m), 2.93 (2H, d, J=21.2 Hz), 2.72 (1H, dd, J=6.4, 15.4 Hz), 2.57 (1H, dd, J=8.8, 15.4 Hz), 2.38 (2H, t, J=7.1 Hz), 1.39 (9H, s), 1.38 (9H, s); FAB-MS (–VE): 395 (M$^+$–H); FAB-HRMS for C$_{21}$H$_{32}$O$_5$P (M$^+$–H) cacld.: 395.1987; found: 395.1964.

(3S)-N-{[N-((1S)-1-{N-[(2S)-2-(naphthylmethyl)pent-4-enyl]carbamoyl}-2-carbamoylethyl)carbamoyl]cyclohexyl}-3-(4-{[bis(tert-butoxy)phosphono]methyl}phenyl) hex-5-enamide (237). mp 82-83° C.; $^1$H NMR (400 MHz, CDCl$_3$): δ 8.02 (1H, d, J=8.5 Hz), 7.78 (2H, t, J=7.9 Hz), 7.67 (1H, d, J=2.4 Hz), 7.65 (1H, d, J=2.8 Hz), 7.42 (2H, m), 7.31 (2H, m), 7.09 (1H, d, J=2.5 Hz), 7.07 (1H, d, J=2.5 Hz), 6.93 (1H, s), 6.90 (1H, s), 6.64 (1H, s), 6.01 (1H, s), 5.80 (1H, m), 5.45 (1H, m), 5.43 (1H, s), 5.03 (2H, m), 4.83 (2H, m), 4.63 (1H, m), 3.30 (1H, m), 3.09 (2H, m), 3.03 (1H, m), 2.98-2.84 (2H, m), 2.92 (2H, d, J=21.4 Hz), 2.48 (2H, m), 2.39 (1H, dd, J=4.8, 15.1 Hz), 2.20 (3H, m), 2.07 (2H, m), 1.95 (1H, d, J=14.2 Hz), 1.82 (1H, d, J=12.9 Hz), 1.69 (1H, dt, J=3.6, 13.6 Hz), 1.60 (1H, dt, J=3.2, 12.9 Hz), 1.46 (3H, m), 1.37 (9H, s), 1.35 (9H, s), 1.23 (1H, m), 1.09 (1H, m), 0.94 (1H, m); FAB-MS (+VE): 843 (MH$^+$), 787 (MH$^+$-C$_4$H$_8$), 731 (MH$^+$-2C$_4$H$_8$).

2-[(9S, 13S, 18S)-8, 11, 21-triaza-18-(4-{[bis(tert-butoxy)phosphono]methyl}phenyl)-13-(naphthylmethyl)-7, 10, 20-trioxospiro[5.15]henicos-15-en-9-yl]acetamide (238). mp 215° C.; $^1$H NMR (400 MHz, CDCl$_3$): δ 8.01 (1H, d, J=8.2 Hz), 7.97 (1H, s), 7.78 (1H, dd, J=1.3, 7.9 Hz), 7.64 (1H, d, J=8.1 Hz), 7.54 (1H, s), 7.42 (2H, m), 7.29 (1H, dd, J=7.0, 8.1 Hz), 7.22 (3H, m), 7.13 (1H, s), 7.11 (1H, s), 6.35 (1H, s), 6.23 (1H, s), 5.68 (1H, m), 5.53 (1H, s), 5.23 (1H, m), 4.77 (1H, s), 3.54 (1H, dd, J=11.8, 22.7 Hz), 3.46 (1H, dd, J=3.2, 13.6 Hz), 3.15 (1H, d, J=13.2 Hz), 3.00 (1H, m), 2.97 (2H, d, J=21.4 Hz), 2.86 (1H, d, J=12.9 Hz), 2.62 (3H, m), 2.46-2.22 (4H, m), 1.88 (3H, m), 1.52 (5H, m), 1.36 (9H, s), 1.35 (9H, s), 1.29 (2H, m), 1.20 (2H, m); FAB-MS (+VE): 815 (MH$^+$), 759 (MH$^+$-C$_4$H$_8$), 703 (MH$^+$-2C$_4$H$_8$).

2-[(9S, 13S, 18S-8, 11, 21-triaza-13-(naphthylmethyl)-7, 10, 20-trioxo-18-[4-(phosphonomethyl)phenyl]spiro[5.15]henicos-15-en-9-yl]acetamide (239). mp 220° C. (dec.); $^1$H NMR (400 MHz, CD$_3$OD): δ 8.06 (1H, d, J=8.1 Hz), 7.83 (1H, d, J=7.9 Hz), 7.69 (1H, d, J=6.0 Hz), 7.46 (2H, m), 7.34 (2H, m), 7.26 (2H, d, J=7.2 Hz), 7.13 (2H, d, J=7.5 Hz), 5.65 (1H, m), 5.21 (1H, m), 4.65 (1H, s), 3.51 (1H, m), 3.43 (1H, dd, J=3.2, 13.5 Hz), 3.08 (2H, d, J=21.2 Hz), 2.98 (1H, m), 2.90-2.50 (6H, m), 2.36 (1H, s), 2.25 (1H, d, J=5.4 Hz), 2.08 (1H, m), 1.90 (1H, m), 1.75 (2H, m), 1.50 (5H, m), 1.33 (2H, m), 1.21 (2H, m); FAB-MS (–VE): 701 (M$^+$–H).

(4S-3-[3-(4-{[bis(tert-butoxy)phosphono]methyl}phenyl)propanoyl]-4-phenyl-1,3-oxazolidin-2-one (240). To a solution of 234 (499 mg) in EtOAc (20 ml) was added 10% palladium on carbon (50 mg), the solution was allowed to stir under H$_2$ overnight. The catalyst was filtered and washed with EtOAc. The filtrate was condensed to give 490 mg compound 240 (98% of yield) as oil. $^1$H NMR (400 MHz, CDCl$_3$): δ 7.29 (3H, m), 7.21 (1H, d, J=1.8 Hz), 7.19 (1H, m), 7.09 (2H, dd, J=2.3, 8.2 Hz), 7.04 (1H, s), 7.02 (1H, s), 5.33 (1H, dd, J=3.7, 8.8 Hz), 4.59 (1H, t, J=8.8 Hz), 4.19 (1H, ddd, J=0.6, 3.7, 9.0 Hz), 3.17 (2H, m), 2.93 (2H, d, J=21.3 Hz), 2.82 (2H, t, J=7.9 Hz), 1.34 (18H, s); FAB-MS (+VE): 502 (MH$^+$), 446 (MH$^+$-C$_4$H$_8$), 390 (MH$^+$-2C$_4$H$_8$).

tert-Butyl(3R)-4-((4S)-2-oxo-4-phenyl(1,3-oxazolidin-3-yl))-3-[(4-{[bis(tert-butoxy) phosphono]methyl}phenyl)methyl]-4-oxobutanoate (241). The title compound was made from compound 240 following the procedure employed to make compound 225 (78% of yield). $^1$H NMR (400 MHz, CDCl$_3$): δ 7.28 (4H, m), 7.23 (1H, m), 7.16 (4H, m), 5.24 (1H, dd, J=3.5, 8.6 Hz), 4.46 (1H, m), 4.44 (1H, t, J=8.8 Hz), 4.12 (1H, ddd, J=0.6, 3.7, 8.8 Hz), 2.97 (2H, d, J=21.3 Hz), 2.93 (1H, m), 2.64 (1H, dd, J=10.5, 17.0 Hz), 2.53 (1H, dd, J=9.0, 12.9 Hz), 2.20 (1H, dd, J=4.1, 17.0 Hz), 1.38 (18H, s), 1.20 (9H, s); FAB-MS (+VE): 616 (MH$^+$), 560 (MH$^+$-C$_4$H$_8$), 504 (MH$^+$-2C$_4$H$_8$), 448 (MH$^+$-3C$_4$H$_8$).

(2R)-2-[(4-{[bis(tert-butoxy)phosphono]methyl}phenyl) methyl]-3-[(tert-butyl)oxy carbonyl]propanoic acid (242). mp 121° C.; $^1$H NMR (400 MHz, CDCl$_3$): δ 8.5 (1H, br. s), 7.14 (2H, dd, J=2.3, 8.2 Hz), 7.08 (1H, s), 7.06 (1H, s), 3.00 (2H, m), 2.97 (2H, d, J=21.7 Hz), 2.73 (1H, dd, J=10.1, 15.6 Hz), 2.50 (1H, dd, J=8.4, 16.6 Hz), 2.25 (1H, dd, J=4.9, 16.6 Hz), 1.37 (9H, s), 1.36 (9H, s), 1.34 (9H, s); FAB-MS (–VE): 469 (M$^+$–H), 413 (M$^+$–H—C$_4$H$_8$).

tert-Butyl(3R)-3-{N-[(N-{(1S)-2-carbamoyl-1-[N-(3-naphthylpropyl)carbamoyl]ethyl}carbamoyl)cyclobexyl]carbamoyl}-4-(4-{[bis(tert-butoxy)phosphono]methyl}phenyl) butanoate (244). mp 137-138° C.; $^1$H NMR (400 MHz, CDCl$_3$): δ 8.07 (1H, dd, J=0.9, 8.2 Hz), 7.82 (1H, dd, J=1.7, 7.8 Hz), 7.75 (1H, d, J=8.2 Hz), 7.68 (1H, dd, J=2.2, 7.1 Hz), 7.63 (1H, t, J=5.7 Hz), 7.45 (2H, m), 7.45 (2H, m), 7.35 (2H, m), 7.18 (2H, dd, J=2.4, 8.1 Hz), 7.03 (1H, s), 7.01 (1H, s), 6.50 (1H, s), 6.41 (1H, s), 5.42 (1H, s), 4.65 (1H, dd, J=5.3, 13.0 Hz), 3.36 (2H, dd, J=6.9, 12.7 Hz), 3.13 (2H, m), 2.98 (2H, d, J=21.5 Hz), 2.96 (3H, m), 2.65 (2H, dd, J=4.9, 15.0 Hz), 2.51 (2H, m), 2.25 (1H, dd, J=3.3, 17.9 Hz), 2.05 (3H, m), 1.87 (3H, m), 1.76 (2H, m), 1.58 (1H, m), 1.42 (9H, s), 1.41 (9H, s), 1.38 (9H, s), 1.23 (3H, m); FAB-MS (+VE): 877 (MH$^+$), 821 (MH$^+$-C$_4$H$_8$), 765 (MH$^+$-2C$_4$H$_8$), 709 (MH$^+$-3C$_4$H$_8$).

(3R)-3-{N-[(N-{(1S)-2-carbamoyl-1-[N-(3-naphthylpropyl) carbamoyl]ethyl}carbamo yl)cyclohexyl]carbamoyl}-4-(4-(phosphonomethyl)phenyl)butanoic acid (245). mp 151-152° C.; $^1$H NMR (400 MHz, CD$_3$OD): δ 8.12 (1H, d, J=8.4 Hz), 7.84 (1H, d, J=7.8 Hz), 7.70 (1H, dd, J=1.5, 7.4 Hz), 7.47 (2H, m), 7.38 (2H, m), 7.21 (2H, dd, J=2.0, 7.9 Hz), 7.08 (1H, s), 7.06 (1H, s), 4.45 (1H, dd, J=5.4, 7.3 Hz), 3.35 (1H, m), 3.28 (1H, m), 3.14 (3H, m), 3.06 (2H, d, J=21.6 Hz), 2.89 (2H, m), 2.81 (1H, dd, J=5.3, 15.5 Hz), 2.59 (2H, m), 2.27 (1H, dd, J=3.9, 17.2 Hz), 2.00 (3H, m), 1.88 (1H, d, J=13.9 Hz), 1.73 (2H, m), 1.51 (2H, m), 1.43 (2H, m), 1.18 (1H, m), 1.02 (1H, m); FAB-MS (–VE): 707 (M$^+$–H); FAB-HRMS for C$_{36}$H$_{44}$N$_4$O$_9$P (M$^+$–H) cacld..; found:.

(3R)-N-{[N-((1S)-1-{N-[(2S)-2-(naphthylmethyl)pent-4-enyl]carbamoyl}-2-carbamo-ylethyl)carbamoyl]cyclohexyl}-3-[4-(phosphonomethyl)phenyl]pent-4-enamide (246). mp 140° C.; $^1$H NMR (400 MHz, CD$_3$OD): δ 8.04 (1H, d, J=8.2 Hz), 7.96 (1H, s), 7.80 (1H, d, J=8.6 Hz), 7.68 (1H, m), 7.42 (2H, m), 7.34 (2H, m), 7.09 (2H, dd, J=2.4, 8.2 Hz), 6.90 (1H, s), 6.88 (1H, s), 5.84 (2H, m), 5.03 (2H, m), 4.89 (2H, m), 4.49 (1H, dd, J=5.0, 6.4 Hz), 3.62 (1H, dd, J=7.6, 14.9 Hz), 3.23 (1H, m), 3.03 (3H, m), 2.99 (2H, d, J=21.8 Hz), 2.69 (1H, dd, J=6.6, 15.7 Hz), 2.62 (3H, m), 2.22 (1H, m), 2.14 (1H, m), 1.99 (2H, m), 1.76 (2H, m), 1.60 (1H, dt, J=3.8, 13.3 Hz), 1.49 (2H, m), 1.31 (2H, m), 1.22 (2H, m); FAB-MS (–VE): 715 (M$^+$–H).

2-(4-Bromophenyl)malonic acid di-tert-butyl ester (302). To a suspension of sodium hydride (60%, 1.876 g, 46.90 mmol) in anhydrous dioxane (80 mL) was added HMPA (6 mL) and di-tert-butyl malonate (10.143 g, 46.90 mmol). The mixture was stirred at room temperature for 1 hour. To the resulting mixture was added copper (I) bromide (8.076 g, 56.28 mmol) and 1-bromo-4-iodobezene (15.00 g, 53.02 mmol), then the mixture was refluxed under argon for 3 hours. After cooling to room temperature, the reaction mixture was added sat. NH$_4$Cl solution and extract with EtOAc. The organic layer was washed with sat. NaCl and dried with Na$_2$SO$_4$. The organic solvent was evaporated in vacuo and the residue was purified by flash chromatography to give 302 (13.224 g), yield 74.6%. 1HNMR (400 MHz, CDCl$_3$) δ 7.47 (dd, 2H, J=6.63, J=1.95), 7.26 (dd, 2H, J=6.54, J=1.85), 4.40 (s, 1H), 1.46 (s, 18H).

To a solution of 302 (7.772 g, 20.95 mmol) and 303 (4.546 g, 20.95 mmol) in Et$_3$N (87 mL) was added Pd(OAc)$_2$ (233 mg, 0.993 mmol) and (O-toly)$_3$P (1.299 g, 4.27 mmol). The mixture was refluxed under argon for 16 h. After cooling to room temperature, the reaction mixture was diluted with CH$_2$Cl$_2$ and filtered through celite. The filtrate was washed with sat. NH$_4$Cl solution and brine, dried over Na$_2$SO$_4$. The solvents were evaporated in vacuo and the residue was purified by flash chromatography to give 304 (9.192 g), yield 86.5%. 1HNMR (400 MHz, CDCl$_3$) δ 7.91 (d, 1H, J=15.6), 7.76 (d, 1H, J=15.6), 7.56 (d, 2H, J=8.4), 7.41-7.33 (m, 7H), 5.55 (dd, 1H, J=4.0, J=8.8), 4.73 (t, 1H, J=8.8), 1.45 (s, 18 H). FABMS (+Ve) m/z 508 [MH$^+$].

To the slurry of PhSCu (3.098 g, 17.94 mmol) in 250 mL dry ether under argon at –40° C. was added dropwise the solution of vinyl magnesium bromide (53.8 mL, 53.8 mmol) for 40 min. The mixture was stirred at –40° C. for 20 min. Then to the reaction solution was added a precooled solution of 304 (9.908 g, 17.94 mmol) in 150 mL THF for 1 h, and the mixture was stirred at –40° C. for 3 h. The reaction was quenched with ice-cooled NH$_4$Cl solution, extracted with CH$_2$Cl$_2$. The solvents were washed with brine and dried over Na$_2$SO$_4$. After evaporation, the residue was purified by flash chromatography to give 305 (5.598 g), yield 58.3%. 1HNMR (400 MHz, CDCl$_3$) δ 7.36-7.20 (m, 9H), 5.96 (ddd, 1H, J=7.03, J=10.54, J=16.98), 5.29 (dd, 1H, J=3.30, J=8.58), 5.00-4.94 (m, 2H), 4.57 (t, 1H, J=8.68), 4.40 (s, 1H), 4.21 (dd, 1H, J=3.32, J=8.78), 3.90 (m, 1H), 3.52 (dd, 1H, J=8.29, J=16.50), 3.31 (dd, 1H, J=6.64, J=16.40), 1.47 (s, 18H). FABMS (+Ve) m/z 536 [MH$^+$].

To a stirred solution of NaHMDS (24.00 mL, 24.00 mmol) was added dropwise 305 (5.58 g, 10.42 mmol) in 60 mL THF at –78° C. The solution was stirred at –78° C. for 1 h, followed by the addition of iodo acetate $^t$butyl ester (2.547 g, 10.52 mmol) in 30 mL THF, stirred for additional 4 h at –78° C. and warmed to room temperature overnight. The reaction was quenched by the addition of 150 mL ice-cooled sat. NH$_4$Cl solution, extracted with CH$_2$Cl$_2$, washed with brine, dried over Na$_2$SO$_4$. The solvents was evaporated in vacuo and the residue was purified by flash chromatography to give 306 (3.601 g), yield 53.2%. $^1$HNMR (400 MHz, CDCl$_3$) δ 7.43-7.22 (m, 9H), 6.08 (dt, 1H, J=9.76, J=17.37), 5.21-5.17 (m, 2H), 4.83-4.76 (m, 2H), 4.41 (s, 1H), 3.97 (t, 1H, J=8.40), 3.86 (dd, 1H, J=2.54, J=8.59), 3.32 (t, 1H, J=9.96), 2.77 (dd, 1H, J=11.22, J=17.27), 2.64 (dd, 1H, J=3.81, J=17.10), 1.47 (s, 18H), 1.31 (s, 9H). FABMS (+Ve) m/z 650 [MH$^+$].

To the solution of 306 (3.582 g, 5.51 mmol) in 84 mL THF-H$_2$O (v:v, 3:1) was added the solution of 30% H$_2$O$_2$ (2.80 mL, 27.55 mmol) at 0° C. via syringe over 10 min, then followed by the addition of lithium hydroxide (463 mg, 11.03 mmol) in 11 mL water. After stirring at 0° C. for 2.5 h, the solution was raised to r.t. for additional 2.5 h. Then sodium sulfite (3.471 g, 27.55 mmol) in 23 mL water was added followed by 1N HCl (27 mL). After the evaporation of sovlent in vacuo, the residue was extracted with EtOAc. The organic layer was washed with brine, dried over Na$_2$SO$_4$. After the removal of solvent in vacuo, the residue was purified by flash chromatography to give 307 (2.020 g), yield 72.6%. $^1$HNMR (400 MHz, CDCl$_3$) δ 7.32 (d, 2H, J=6.44), 7.21 (d, 2H, J=6.24), 5.95 (m, 1H), 5.17-5.13 (m, 2H), 4.40 (s, 1H), 3.68 (t, 1H, J=8.59), 3.23 (m, 1H), 2.63 (dd, 1H, J=10.73, J=16.78), 2.44 (dd, 1H, J=3.90, J=16.98), 1.46 (s, 18H), 1.28 (s, 9H). FABMS (+Ve) m/z 503 [M−H].

To a solution of 308 (448 mg, 1.32 mmol) and Fmoc-1-amino-cyclohexanecarboxylic acid (483 mg, 1.32 mmol) in DMF (7 mL) was added HOBT (196 mg, 1.45 mmol) and EDCI•HCl (278 mg, 1.45 mmol) at 0° C. The mixture was stirred at R.T. overnight. After the removal of solvent in vacuo, the residue was dissolved in ethylacetate. The organic solvent was washed with 5% citric acid, 5% sodium bicarbonate and brine. The organic solvent was evaporated and the residue was purified by flash chromatography to give 309 (601 mg), yield 66%. $^1$HNMR (400 MHz, CDCl$_3$) δ 8.09 (m, 1H), 8.00 (m, 1H), 7.78-7.52 (m, 5H), 7.43-7.21 (m, 8H), 6.13 (m, 1H), 5.73 (m, 1H), 5.29 (m, 1H), 5.24 (s, 1H), 5.02-4.87 (m, 2H), 4.73 (m, 1H), 4.26 (dd, 1H, J=6.64, J=10.54), 4.18 (dd, 1H, J=6.05, J=10.73), 4.03 (t, 2H, J=6.35), 3.84 (m, 1H), 3.26 (m, 1H), 3.17-3.03 (m, 3H), 2.95-2.87 (m, 2H), 2.44 (dd, 1H, J=5.07, J=15.22), 2.12-1.54 (m, 11H). FABMS (+Ve) m/z 687 [MH$^+$].

To a solution of 309 (594 mg, 0.865 mmol) in acetonitrile (6 mL) was added piperidine (0.5 mL). The resulting solution was stirred at R.T. for 1.5 hours. After the evaporation of the solvent in vacuo, the residue was submitted to flash chromatograph to give 310 (345 mg), yield 85.8%. $^1$HNMR (400 MHz, CDCl$_3$) δ 8.98 (d, 1H, J=7.41), 7.97 (m, 1H), 7.84 (m, 1H), 7.72 (d, 1H, J=8.00), 7.53-7.44 (m, 2H), 7.38 (dd, 1H, J=7.03, J=8.2), 7.31 (dd, 1H, J=1.17, J=7.03), 7.14 (m, 1H), 6.17 (m, 1H), 5.82 (m, 1H), 5.39 (m, 1H), 5.12-5.07 (m, 2H), 4.61 (m, 1H), 3.26 (t, 2H, J=5.66), 3.07 (dd, 1H, J=6.64, J=14.25), 2.96 (dd, 1H, J=7.03, J=14.06), 2.82 (dd, 1H, J=3.91, J=15.03), 2.54 (dd, 1H, J=7.02, J=15.03), 2.14-2.08 (m, 3H), 1.99-1.32 (m, 12H). FABMS (+Ve) m/z 465 [MH$^+$].

Compound 307 (58 mg, 0.115 mmol), Compound 310 (42 mg, 0.094 mmol) and HOAt (18 mg, 0.127 mmol) were dissolved in 3 mL DMF. To the solution was added EDCI•HCl (26.5 mg, 0.138 mmol) at 0° C., stirred for 1.5 h at RT. Then the solution was heated to 50° C. for 24 h. After the solvent was evaporated in vacuo, the residue was purified by flash chromatogaphy to give 311 (18 mg), yield 21%. $^1$HNMR (400 MHz, CDCl$_3$) δ 8.08 (d, 1H, J=8.59), 7.84 (dd, 1H, J=1.37, J=7.81), 7.71 (t, 1H, J=3.12), 7.52-7.18 (m, 9H), 7.09 (d, 1H, J=8.2), 6.18 (s, 1H), 5.94 (m, 1H), 5.86 (m, 1H), 5.68 (m, 1H), 5.30 (s, 1H), 5.17-5.06 (m, 2H), 4.97-4.92 (m, 2H), 4.54 (m, 1H), 4.37 (m, 1H), 3.38-2.66 (m, 10H), 2.50 (m, 1H), 2.26 (m, 1H), 2.15 (m, 1H), 1.77-1.59 (m, 10 H), 1.47 (s, 9H), 1.45 (s, 9H), 1.40 (s, 9H).

To the solution of 311 (18 mg, 0.0189 mmol) in CH$_2$Cl$_2$ (6 mL) was added ruthenium catalyst (7.8 mg, 0.00946 mmol) predissolved in 2 mL CH$_2$Cl$_2$. The reaction was heated to 45° C. for 40 h. After the evaporation of solvent in vacuo, the residue was purified by flash chromatography to give 312 (3 mg) and recover 311 (5 mg), yield 24%. $^1$HNMR (400 MHz, CDCl$_3$) δ 8.15 (d, 1H, J=8.20), 8.02 (d, 1H, J=8.40), 7.77 (m, 1H), 7.65 (d, 1H, J=8.20), 7.48-7.16 (m, 9H), 6.25 (s, 1H), 5.78 (s, 1H), 5.74 (m, 1H), 5.25 (m, 1H), 5.01 (m, 1H), 4.66 (m, 1H), 4.34 (m, 1H), 3.92 (m, 1H), 3.75 (m, 1H), 3.35-2.57 (m, 7H), 2.29-2.19 (m, 2H), 2.14-2.02 (m, 2H), 1.92-1.53 (m, 10H), 1.43 (s, 9H), 1.41 (s, 9H), 1.33 (s, 9H).

Compound 313 is obtained from 312 by de-esterifying.

EXAMPLE 2

This Example illustrates some of the properties of the compounds in accordance with embodiments of the present invention.

To characterize the time period and dose which the Grb2 SH2 domain inhibitor (antagonist) compound of formula 4 enters intact cells, the murine IL-3-dependent cell line 32D c-met was used. The effects of the inhibitor on c-Met-Grb2 interaction was examined by co-immunoprecipitation/immunoblot analysis. Cells were cultured in RPMI 1640+15% FBS and 5% WEHI-3B conditioned medium. Intact 32Dc-met cells were treated with different amount (3, 30, 300 nM) of the compound for 1, 2, 4, and 16 h, then briefly stimulated with HGF/NK1 for 10 minutes before lysis, immunoprecipitated with anti-Grb2 antibodies (Santa Cruz), and immunoblotting with anti-c-Met (Santa Cruz), or anti-Grb (Transduction Lab). HGF/NK1 stimulated co-immunoprecipitation of the 145 kDa c-Met beta subunit with Grb2. When cells were pretreated for 16 h with 30 nM or 300 nM compound of formula 4 prior to HGF/NK1 stimulation, the amount of HGF receptor that was co-immunoprecipitated with Grb2 was reduced by approximately 50%.

Figure 11:
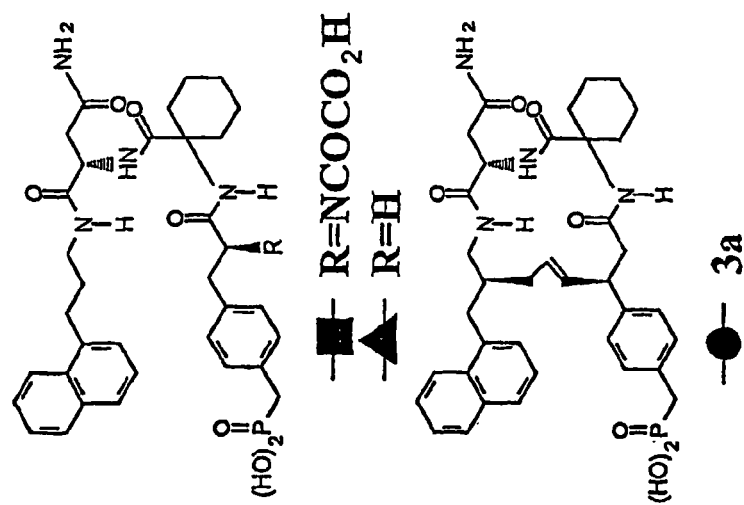
FIG. 11 depicts the innate affinity data for inhibitors 1, 2, and 3a to the Grb2 SH2 domain protein measured by the ELISA techniques. The X-axis depicts the concentration of the inhibitor and the Y-axis depicts the decrease in binding relative to the control. IC50 (μM) are 0.02 (■), 2 (▲) and 0.035 (●) (n=3).
Figure 11:
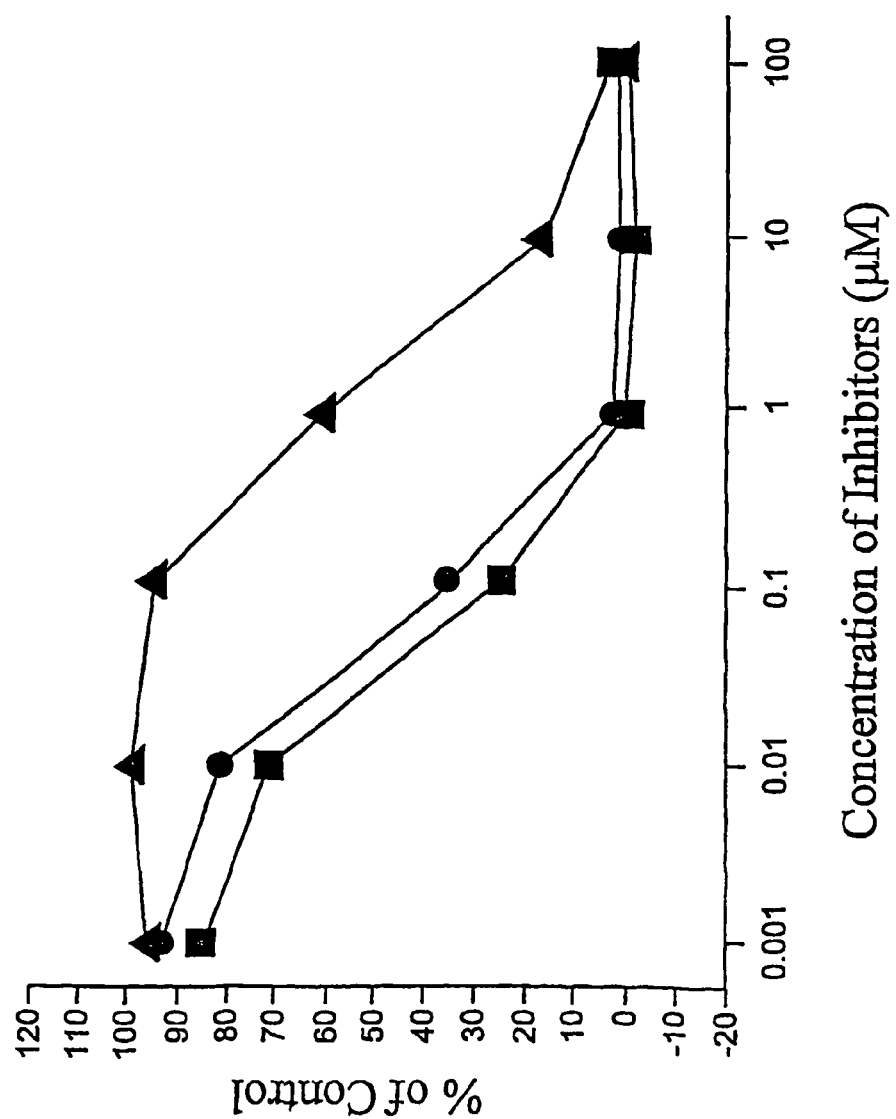
Figure 24:
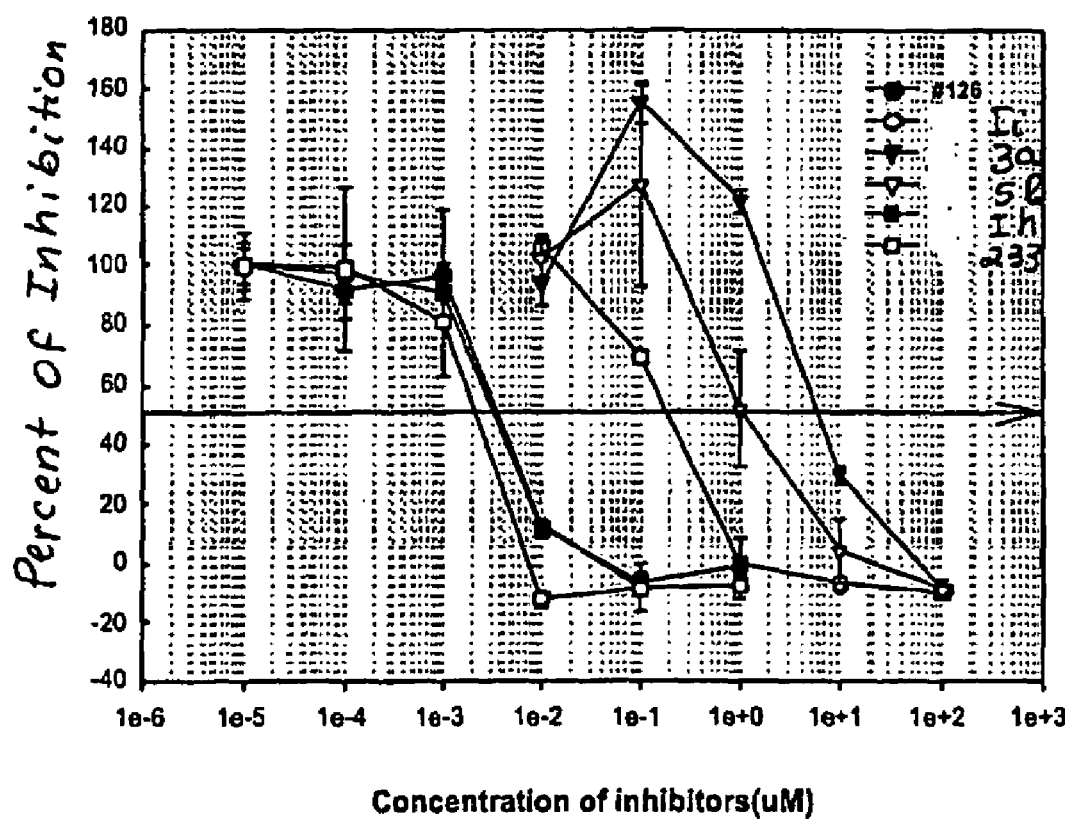
FIG. 24 depicts the extracellular ELISA GrB2 SH2 domain binding assay on compounds 126, Ii, 3a, 5b, Ih, and 233. The $IC_{50}$ values are as follows: 126 (0.003); Ii (0.18); 3a (6.00); 5b (1.8); Ih (0.003); and 233 (0.002).

Inhibition of Grb2 SH2 Domain Binding using ELISA Techniques. A biotinated phosphopeptide encompassing a Grb2 SH2 domain binding sequence derived from SHC protein, was bound at 20 ng/mL to 96-well plates overnight. Nonspecific interactions were inhibited by 5% bovine serum albumin containing TBS. Samples of recombinant purified Grb2 SH2-GST fusion protein were preincubated with serial of dilutions of inhibitors, then added into each well. After extensive washing with 0.1% bovine serum albumin in TBS, bound Grb2 SH2 domain was detected using anti-GST antibodies and goat anti-mouse antibody conjugated to alkaline phosphatase. Quantitation of bound alkaline phosphatase was achieved by a colorimetric reaction employing para-nitrophenyl phosphate as substrate. The results obtained are set forth in FIGS. 11 and 24. Compound 3a (FIG. 11) showed greater inhibition compared to compound 2, a compound which is not constrained in the beta bend fashion. Compound 233 (FIG. 24) shows much enhanced binding to Grb2 SH2 domains. The IC$_{50}$ is 0.002 µm.

Figure 12:
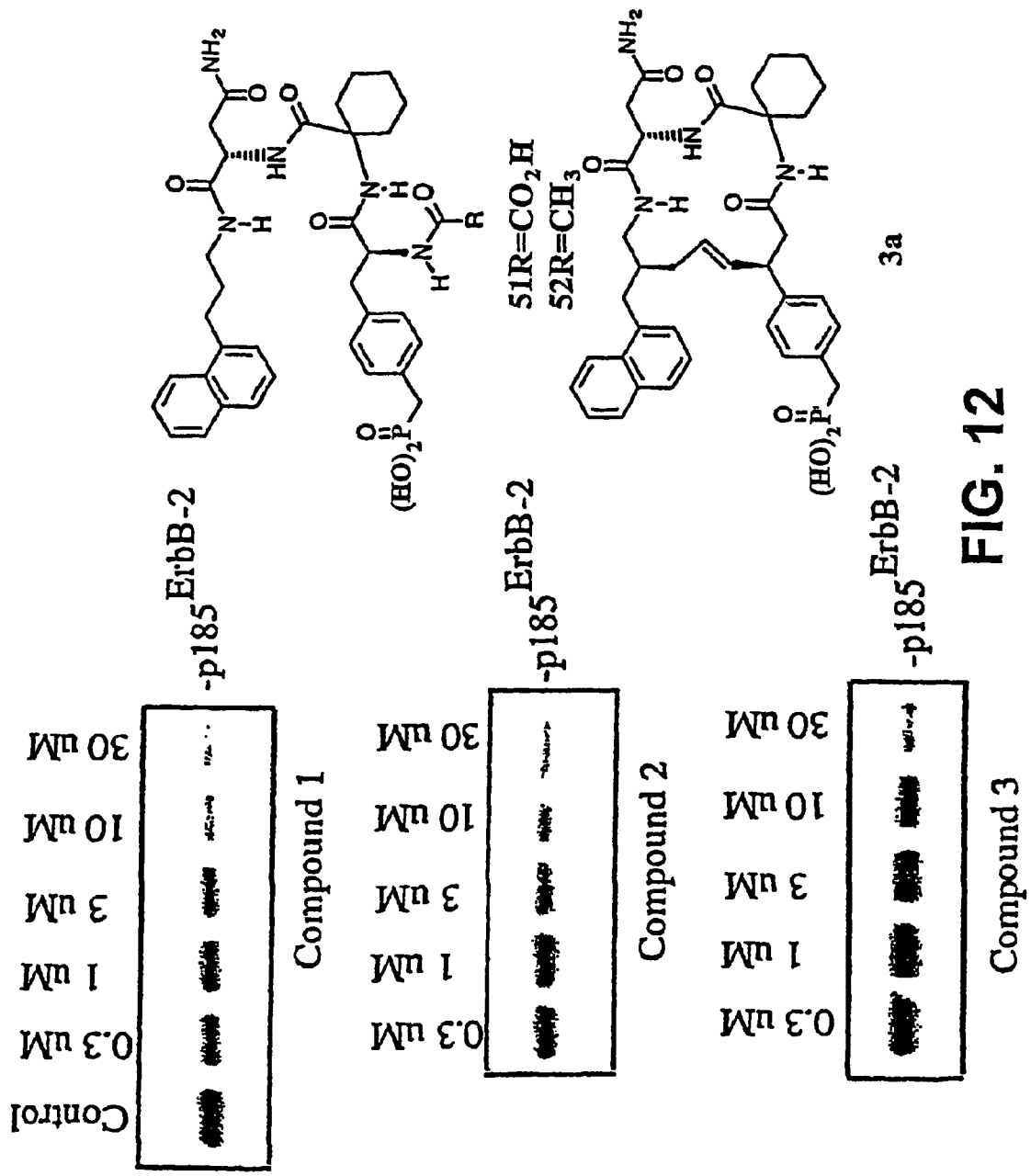
FIG. 12 depicts the Grb2 SH2 domain binding inhibition in whole cell preparations for compounds 3a and 51-52. Cells were treated with inhibitor at the concentrations indicated prior to stimulation with growth factor. Cells were the washed, lysed and immunoprecipitated with anti-Grb2 antibody, then pTyr Western blots against the ErbB-2 protein were run.
Figure 25A:
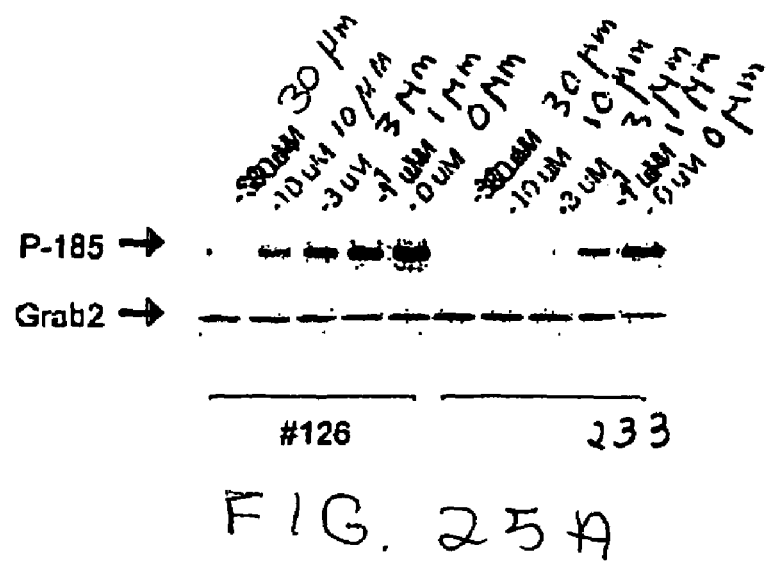
FIG. 25A depicts the effect of compounds 233 and 126 on erbB-2 and Grb2 association in MDA453 cells (IP: GrB2 C-23 WB: PTy(PY99) and Grb2).
Figure 25B:
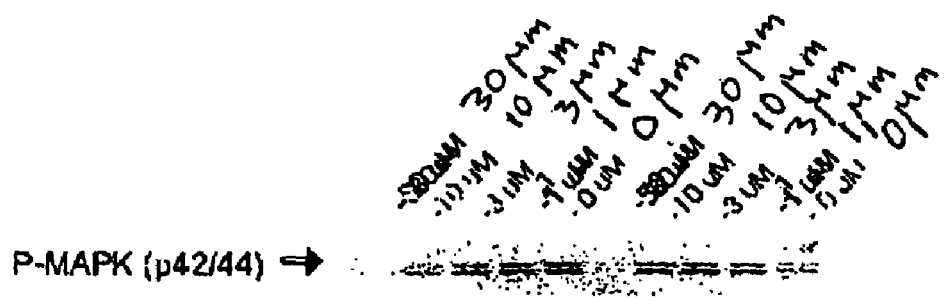
FIG. 25B depicts the effect of compounds 233 and 126 on MAPK phosphorylation in MDA453 cells.

Inhibition of Grb2 SH2 Domain Binding in Whole Cells. ErbB2 over expressing breast cancer cells, MDA-MB-453, were treated with inhibitors (25 µM) for 3 h in serum-free IMEM medium (Gibco). Cells were washed twice with PBS to remove inhibitor, then cell lysates were prepared using 1% Triton X-100 in PBS containing 0.2 mM NaVO4. Grb2 and associated Grb2-binding proteins were immunoprecipitated from each lysate (500 ug) with anti-Grb2 antibodies and collected using protein A Sepharose. Immunoprecipitated proteins were separated by SDS-PAGE on 8-16% gradient gels (Novex) and pTyr-containing proteins were detected by Western blotting using anti-phosphotyrosine antibodies (Upstate Biochemicals Inc.). Previous experiments have shown that a major tyrosine phosphorylated protein in these cells is the p185 erbB-2, which is over expressed as a consequence of gene amplification. Western blotting with Grb2 MAb was done as a control. The results obtained are depicted in FIG. 12. Compound 233 is very effective in inhibiting Grb2 SH2 domain binding in whole cell assays (FIG. 25).

Figure 13:
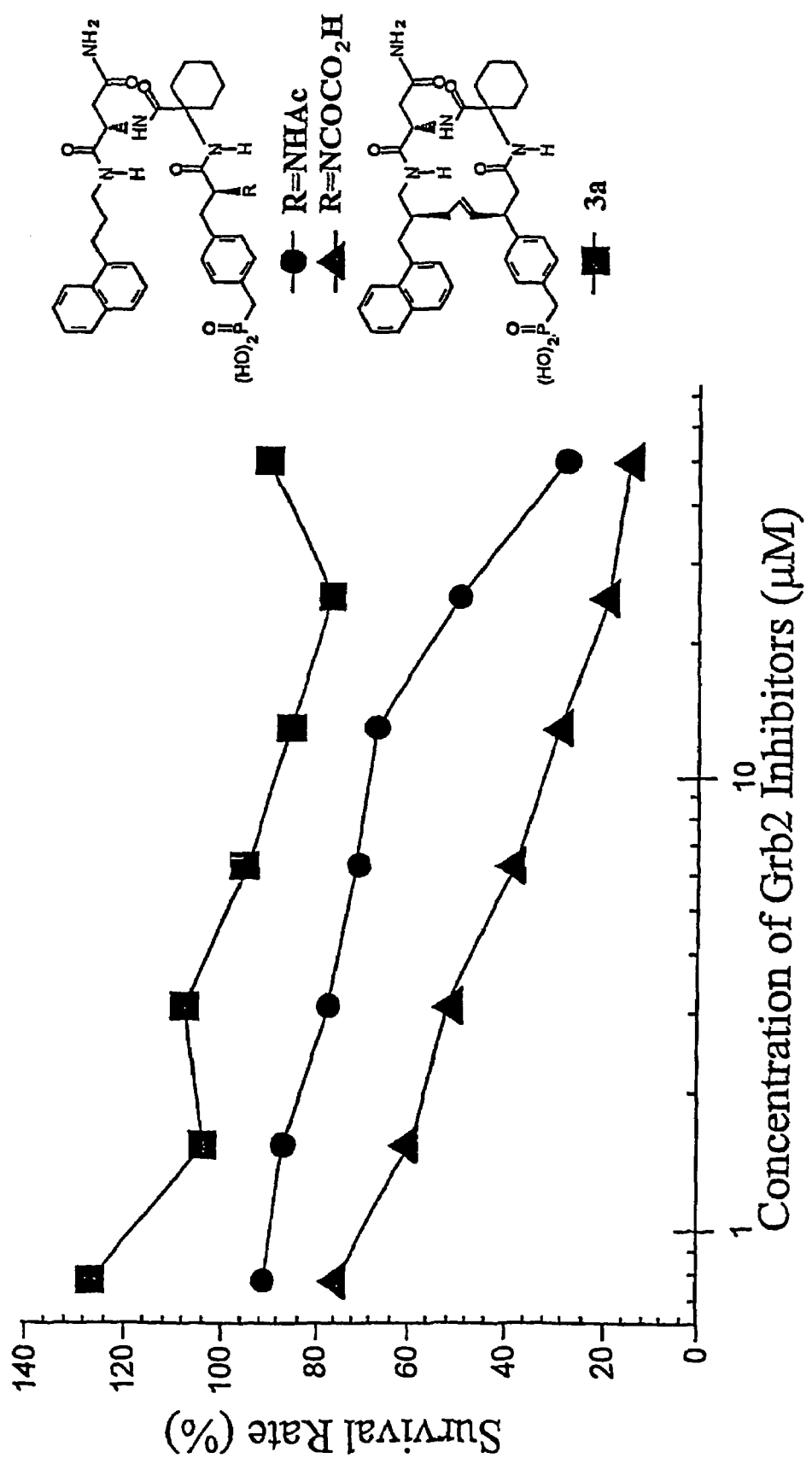
FIG. 13 depicts the effect of embodiments of the Grb2 SH2 domain inhibitors on the growth of MDA-453/ml cells. Cells were treated with inhibitor at the concentrations indicated prior to stimulation with growth factor. Cells were washed, lysed and immunoprecipitated with anti-Grb2 antibody, then pTyr Western blots against the ErbB-2 protein were run.
Figure 14A:
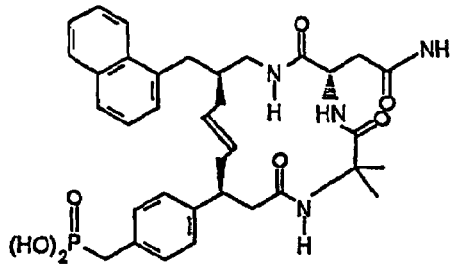
FIGS. 14a-e depict the formulas of compounds Ii, 3a, 5b, Ih, and 126, respectively.
Figure 14B:
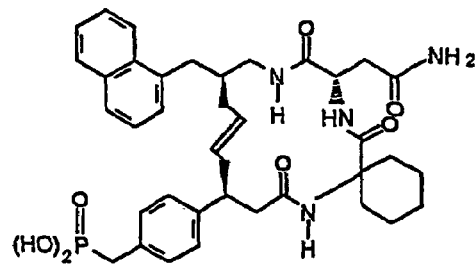
Figure 14C:
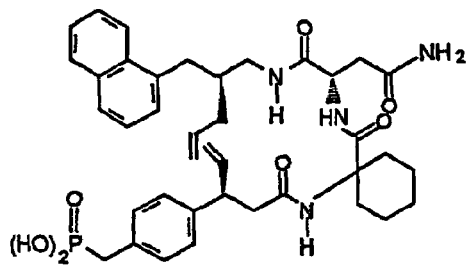
Figure 14D:
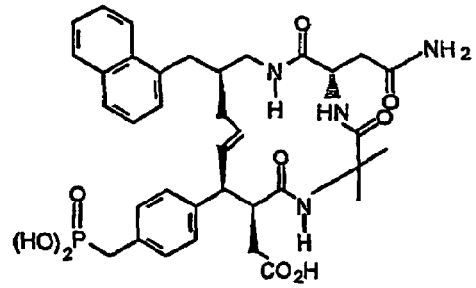
Figure 14E:
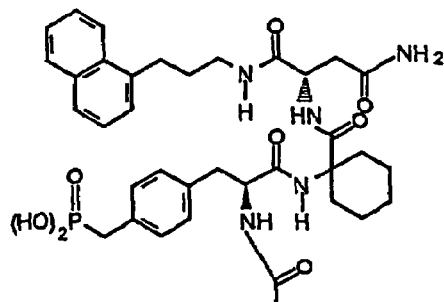
Figure 15:
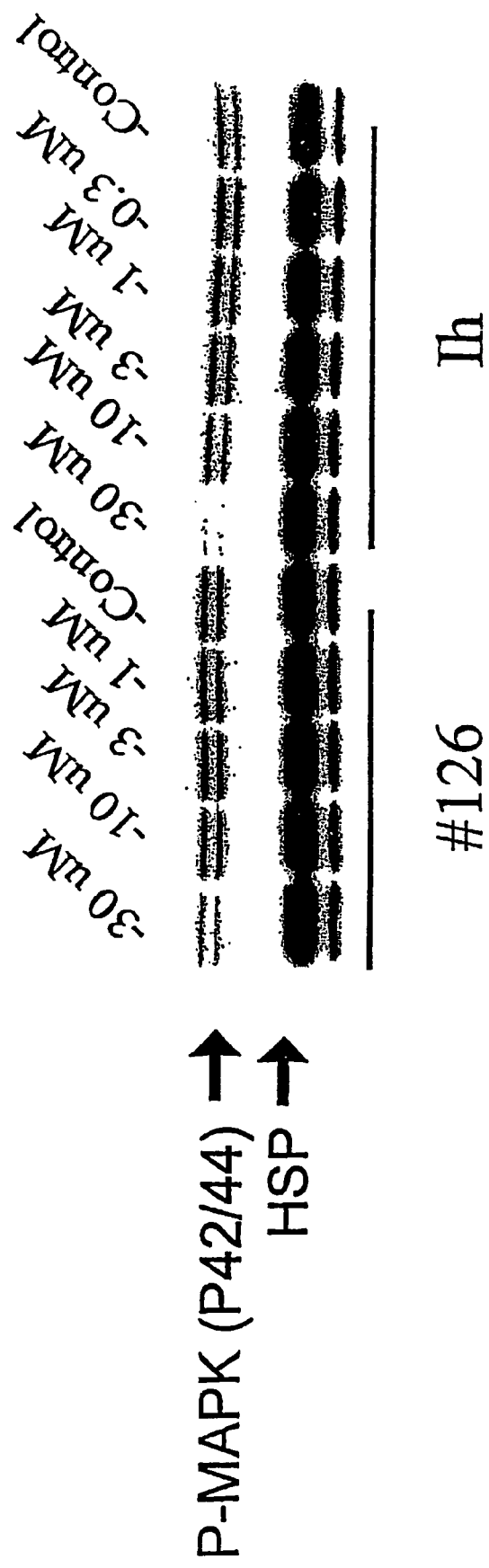
FIG. 15 depicts the effect of compounds Ih and 126 on phosphorylation of MAP Kinase in MDA453 cells (4 hour treatment in 10% FBS).
Figure 16A:
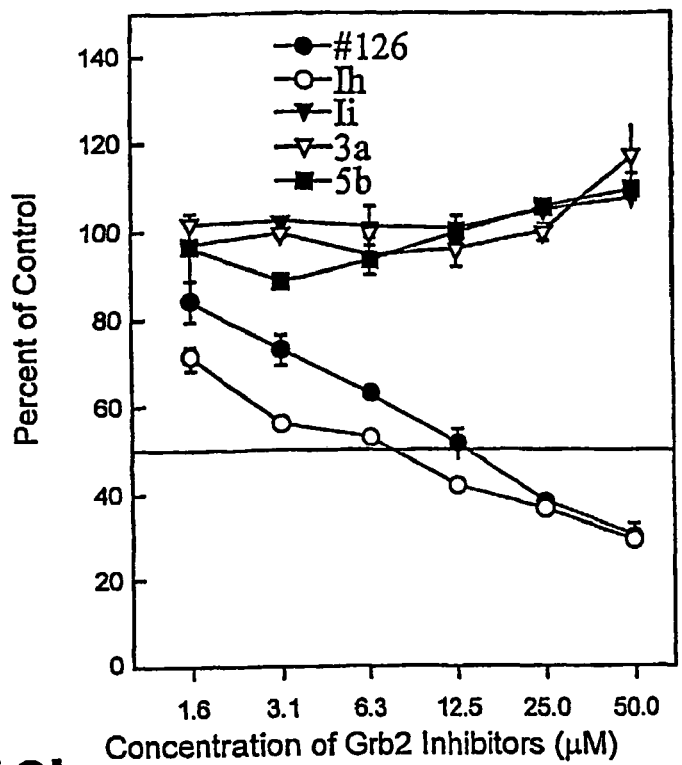
FIG. 16a depicts the dose response curves of compounds 126, Ih, Ii, 3a, and 5b, on the growth of MDA453 breast cancer cells after treatment with growth factor.
Figure 16B:
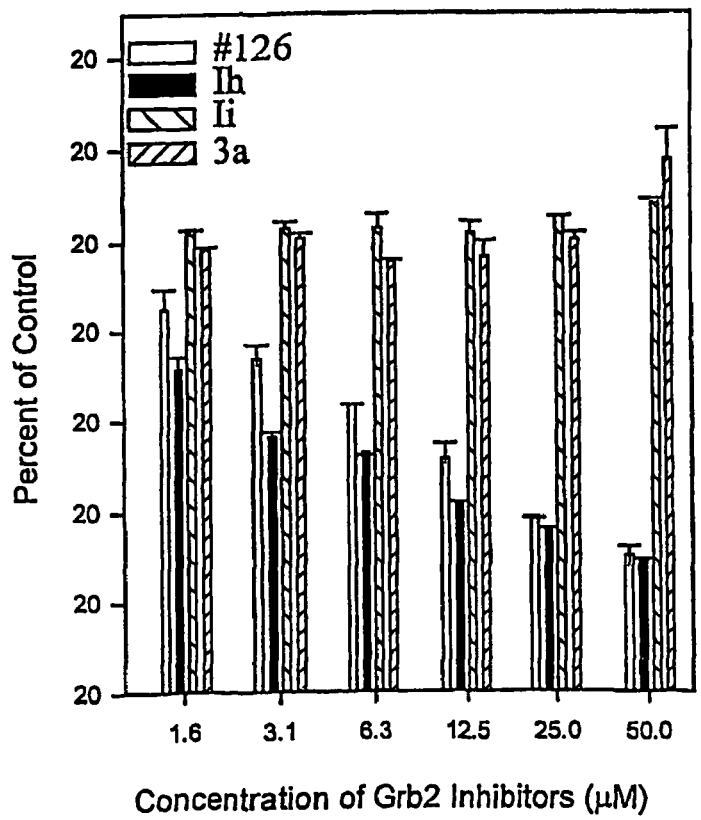
FIG. 16b depicts the dose response bar graphs of compounds 126, Ih, Ii, and 3a on the growth of MDA453 breast cancer cells after treatment with growth factor.
Figure 17:
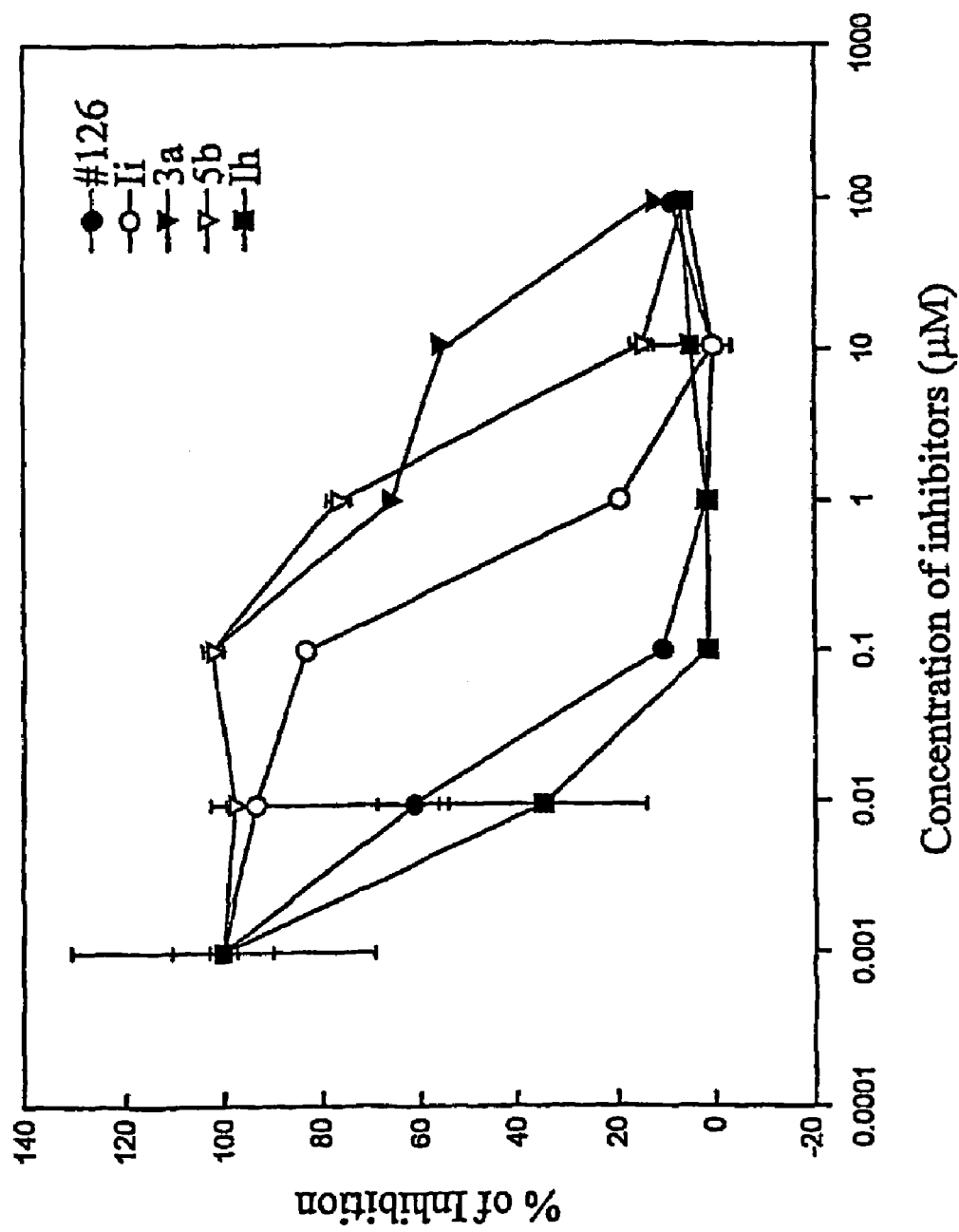
FIG. 17 depicts the extracellular ELISA assay of Grb2 SH2 domain binding inhibitors. IC$_{50}$ of compounds 126, Ii, 3a, 5b, and Ih are respectively, 0.01, 0.25, 4.00, 2.00, and 0.004 μM.
Figure 19:
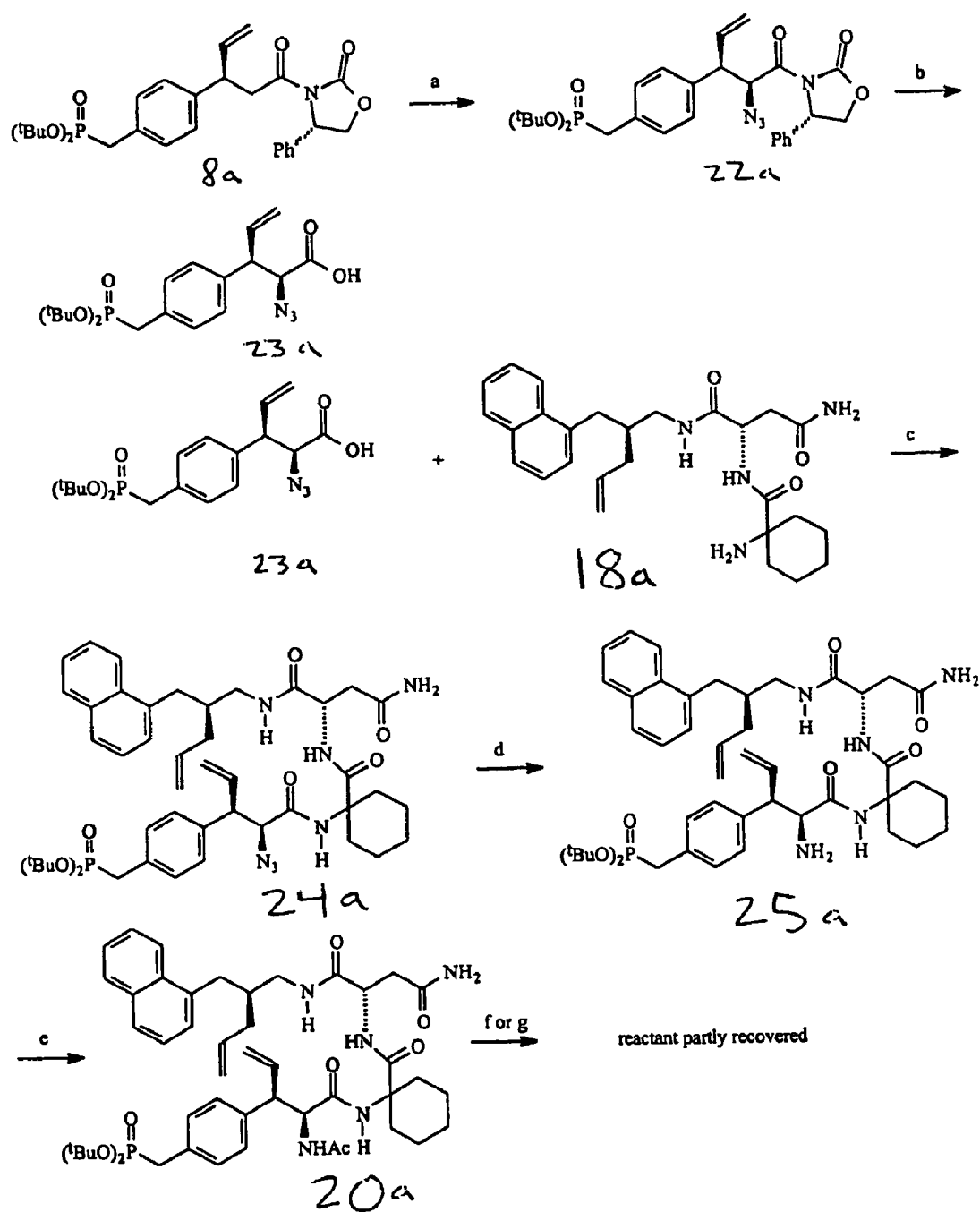
FIG. 19 depicts a reaction scheme for the preparation of compound 20a. (a) NaHMDS, trisyl azide, THF, −78° C., 73%; (b) LiOH, H$_2$O$_2$, THF-H$_2$O, 92%; (c) HOBt, DIPCDI, DMF, 70%; (d) Ph$_3$P, THF-H$_2$O, reflux, quantitative; (e) Ac$_2$O, Et$_3$N, DCM, 80%; (f) (PCy$_3$)$_2$Cl$_2$Ru=CHPh, DCM, reflux; (g) (PCy$_3$)(IMes)CL$_2$Ru=CHPh, toluene, 80° C.
Figure 20:
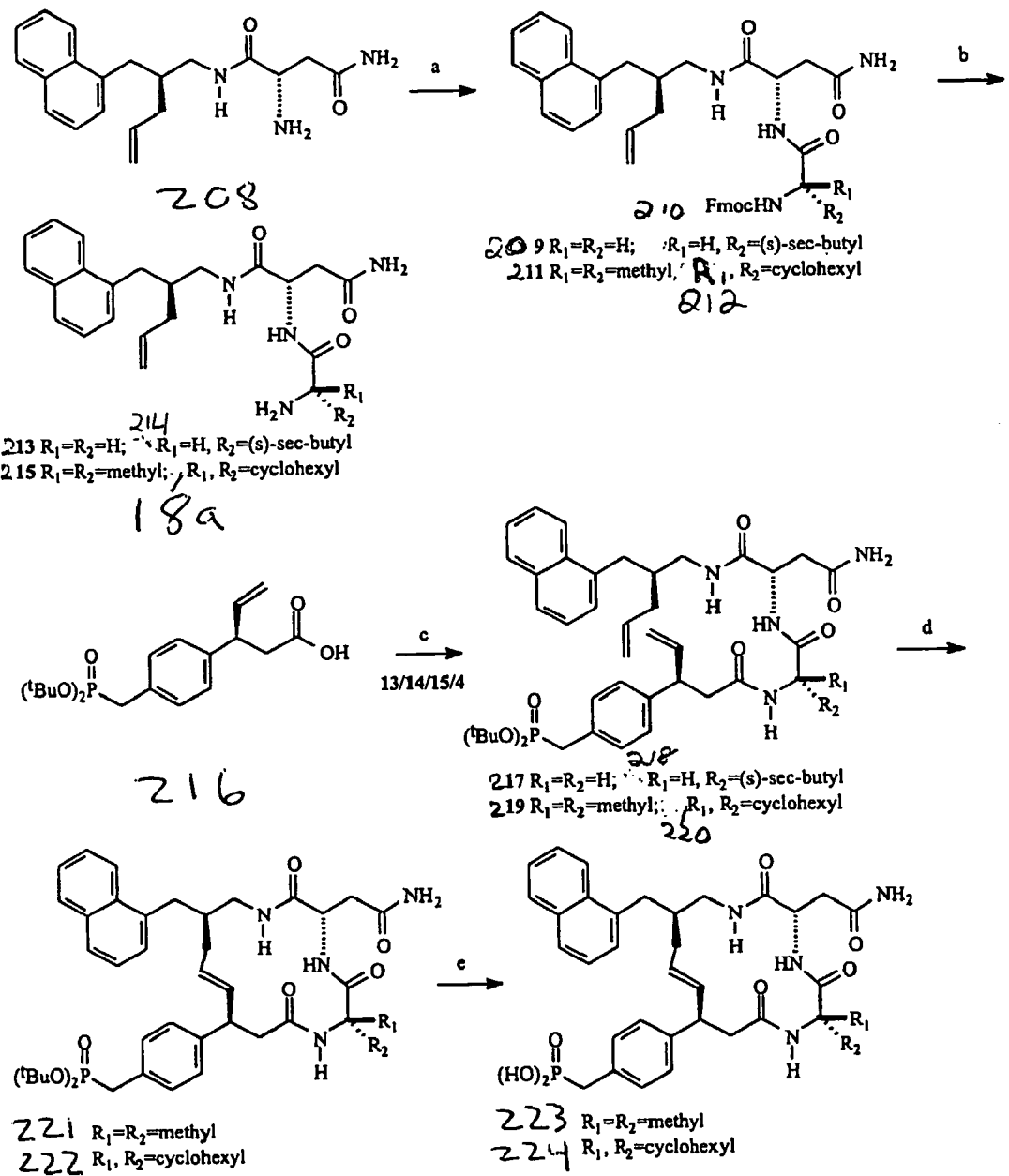
FIG. 20 depicts a reaction scheme for the preparation of compounds 223-224. (a) for 109: Fmoc-Gly-OH, HOBt, DIPCDI, DMF, 89%; for 210: Fmoc-Ile-OH, HOBt, DIPCDI, DMF, 86%; for 211: Fmoc-Aib-OH, HOBt, DIPCDI, DMF, 88%; for 212: FMoc-1-amino-cyclohexane carboxylic acid, HOBt, DIPCDI, DMF, 82%; (b) Piperidine, DMF, quantitative; (c) HOBt, DIPCDI, DMF, 82% (217); 81% (218); 78% (219); 76% (220); (d) (PCy$_3$)$_2$Cl$_2$Ru=CHPh, DCM, reflux; 63% (221); 67% (222); (e) TFA-TES-H$_2$O, quantitative.
Figure 21:
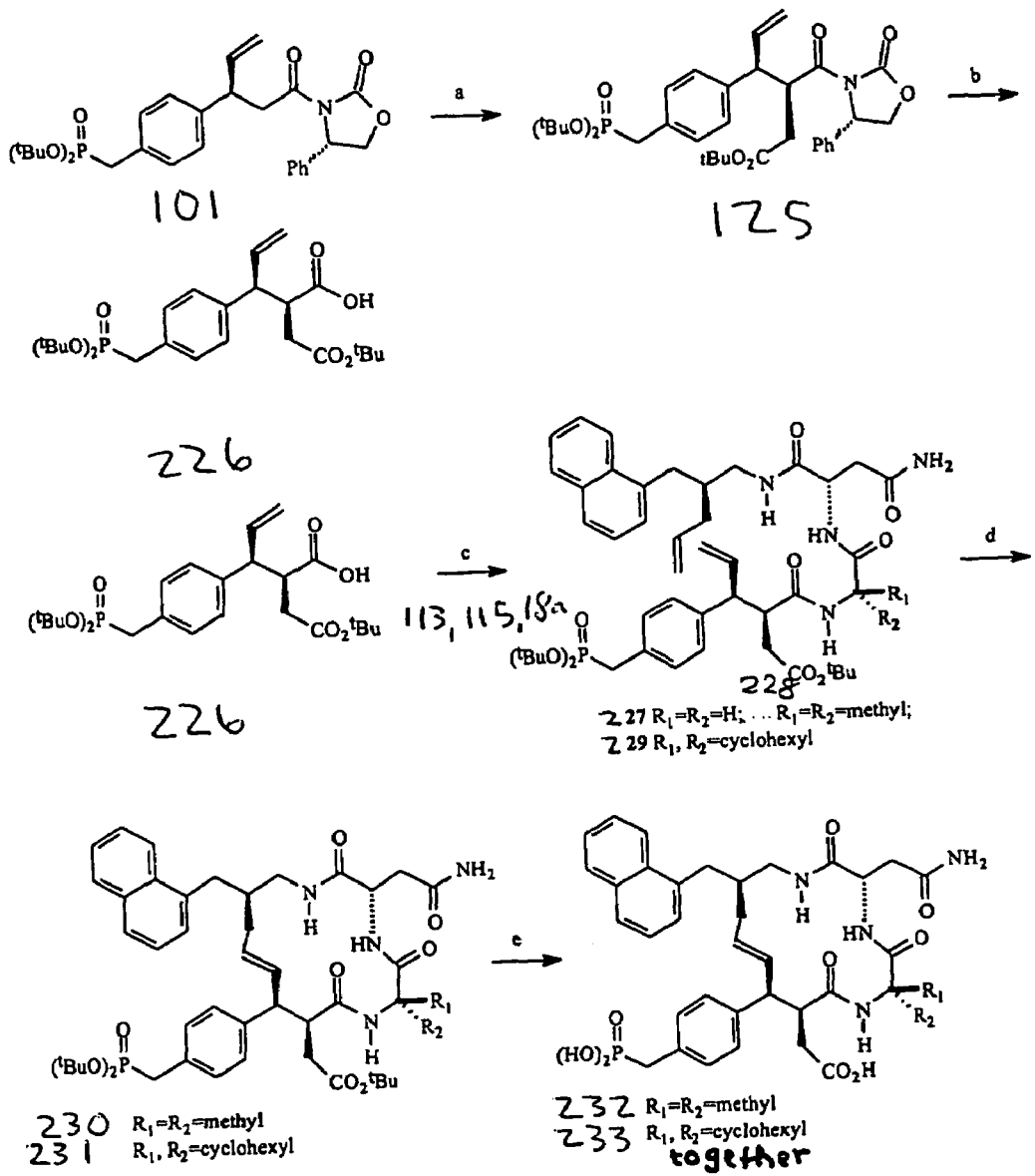
FIG. 21 depicts a reaction scheme for the preparation of compounds 232-233. (a) NaHMDS, BrCH$_2$CO$_2$$^t$Bu, THF, −78° C., 77%; (b) LiOH, H$_2$O$_2$, THF-H$_2$O, 85%; (c) HOAt, EDCI, DMF, 85% (227); 75% (228); 72% (229); (d) (PCy$_3$)$_2$Cl$_2$Ru=CHPh, DCM, reflux; 83% (230); 87% (231); (e) TFA-TES-H$_2$O, quantitative.
Figure 22:
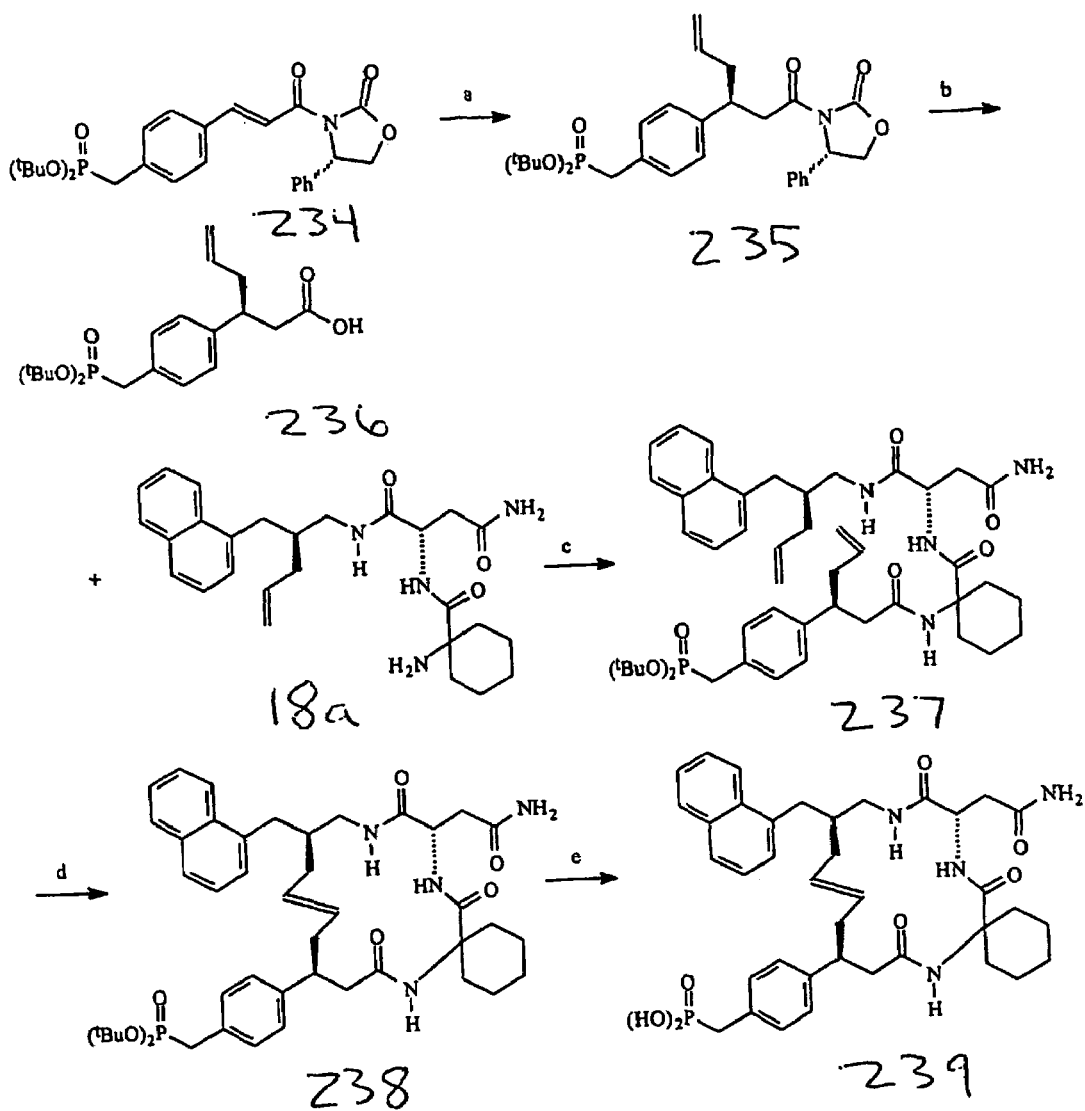
FIG. 22 depicts a reaction scheme for the preparation of compound 239. (a) allylmagnesium bromide, CuBr.Me$_2$S, THF, −78° C., 83%; (b) H$_2$O$_2$, LiOH, THF-H$_2$O, 90%; (c) HOBt, EDCI, DMF, 79%; (d) (PCy$_3$)$_2$Cl$_2$Ru=CHPh, DCM, reflux; 77%; (e) TFA-TES-H$_2$O, quantitative.
Figure 23:
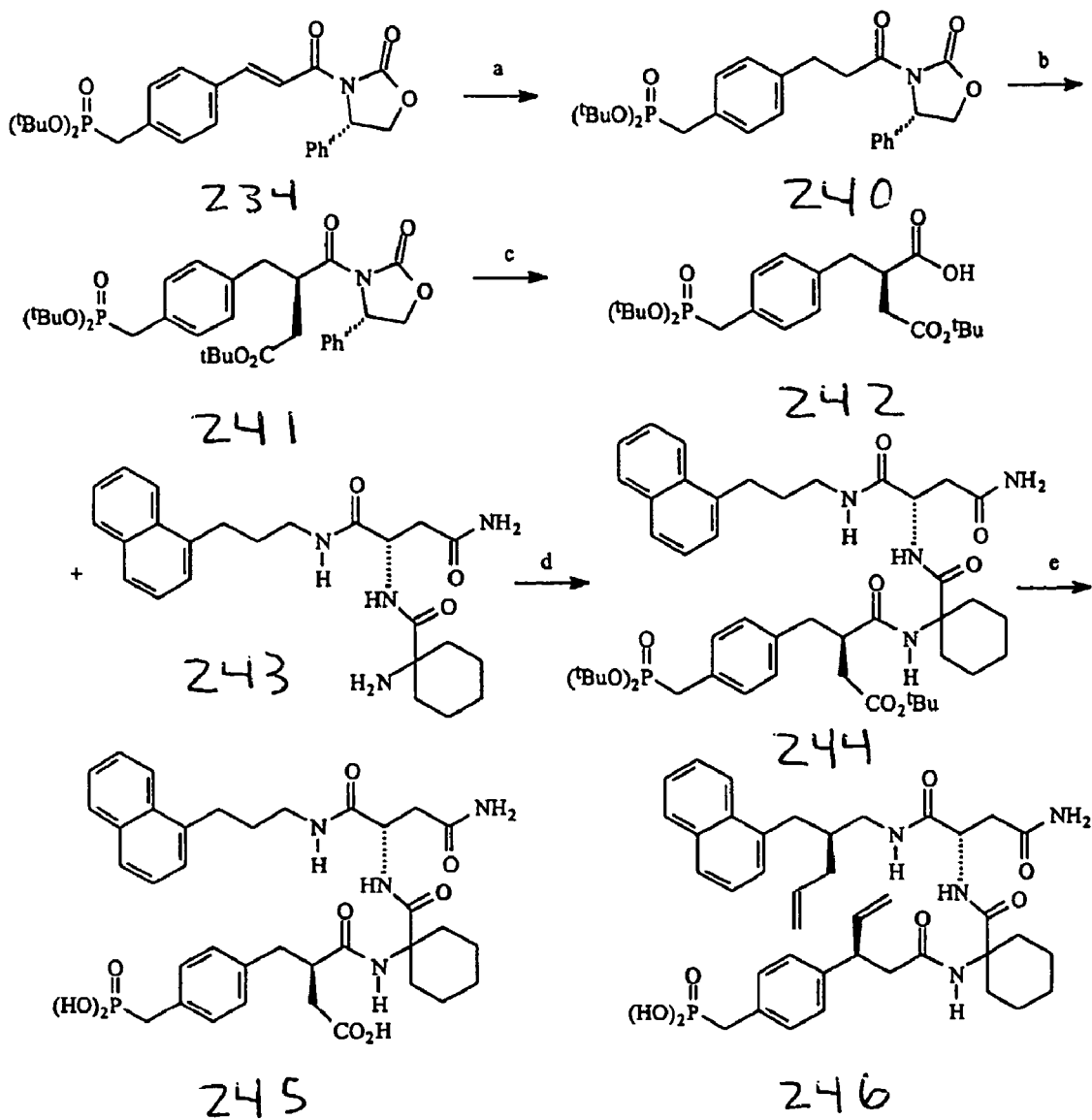
FIG. 23 depicts a reaction scheme for the preparation of compound 246. (a) 10% Pd/C, H$_2$, EtOAc, quantitative; (b) NaHMDS, BrCH$_2$CO$_2$$^t$Bu, THF, −78° C., 78%; (c) H$_2$O$_2$, LiOH, THF-H$_2$O, 86%; (d) HOAt, EDCI, DMF, 82%; (e) TFA-TES-H$_2$O, quantitative.

Assay of Cell Proliferation. Cell lines were obtained from the American Type Culture Collection (Rockville, Md.) and Lombardi Cancer Center, Georgetown University Medical Center. Cells were routinely maintained in improved minimal essential medium (IMEM, Biofluids, Rockville, Md.) with 10% fetal bovine serum. Cultures were maintained in a humidified incubator at 37° C. and 5% $CO_2$. The effect of Grb2 inhibitors on cell proliferation was determined by direct cell counting. Briefly, 25,000 cells were plated into 24-well plates and the Grb2 inhibitors at appropriate concentrations were added and cultured for 8 to 10 days. Cells were collected every other day and counted with a Coulter counter. The results obtained are depicted in FIG. 13.

Figure 26A:
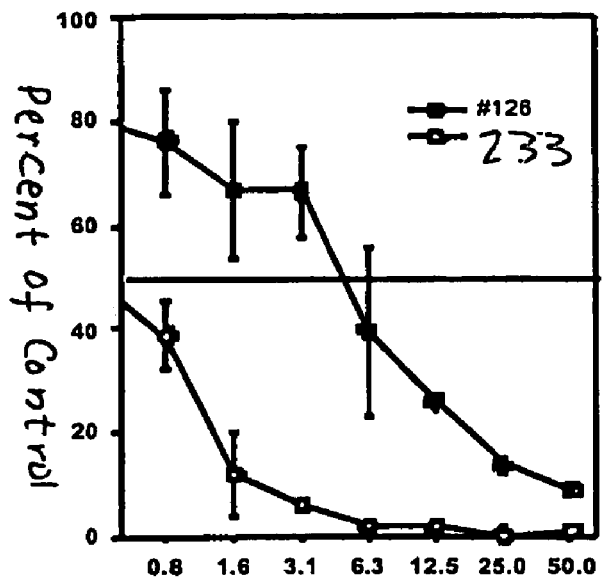
FIG. 26 depicts the results of cell growth inhibition produced by compounds 233 and 126 in erbB-2 dependent breast cancer cells.
Figure 26B:
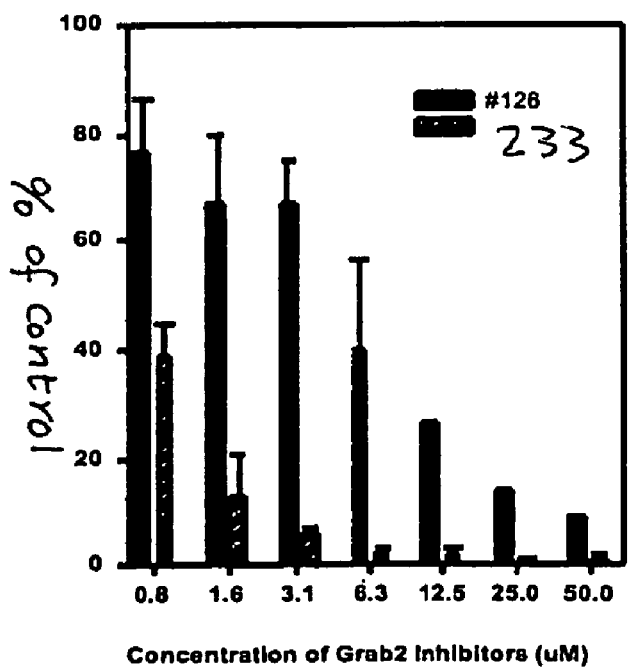
Figure 27:
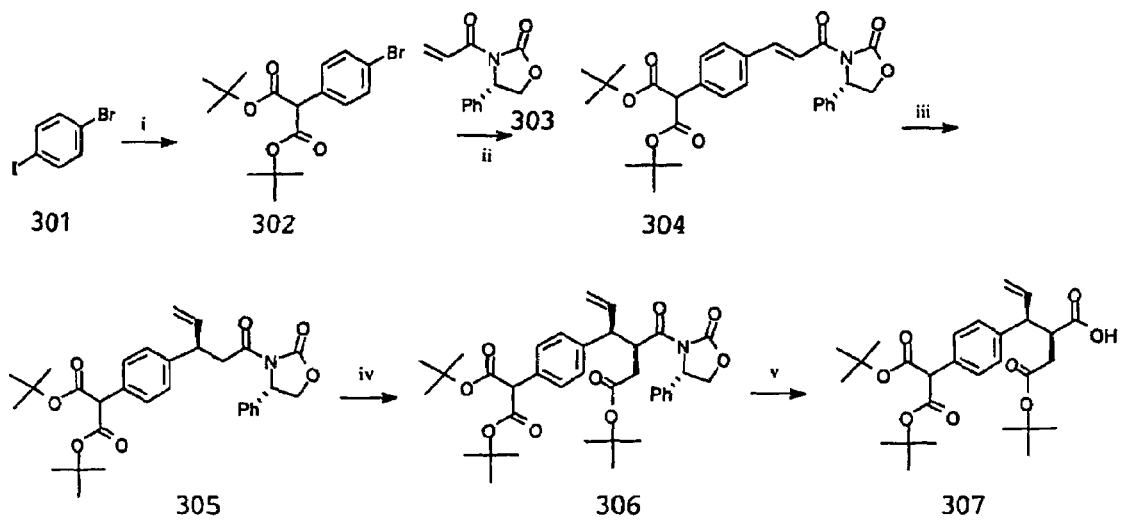
FIG. 27 depicts a reaction scheme for the preparation of compound 307. Reagents and conditions: (i) di-tert-butyl malonate, NaH, CuBr, dioxane, HMPA, reflux, 3 h, 74.6%; (ii) $Pd(OAc)_2$, $(O-toly)_3P$, $Et_3N$, reflux, 16 h, 86.5%; (iii) Vinyl magnesium bromide, PhSCu, $Et_2O$, THF, −40° C., 3 h, 58.3%; (iv) $ICH_2CO_2^tBu$, NaHMDS, THF, −78° C., 2 h, 53.2%; (v) LiOH, $H_2O_2$, 0° C. 2.5 h, then r.t. 2.5 h.
Figure 28:
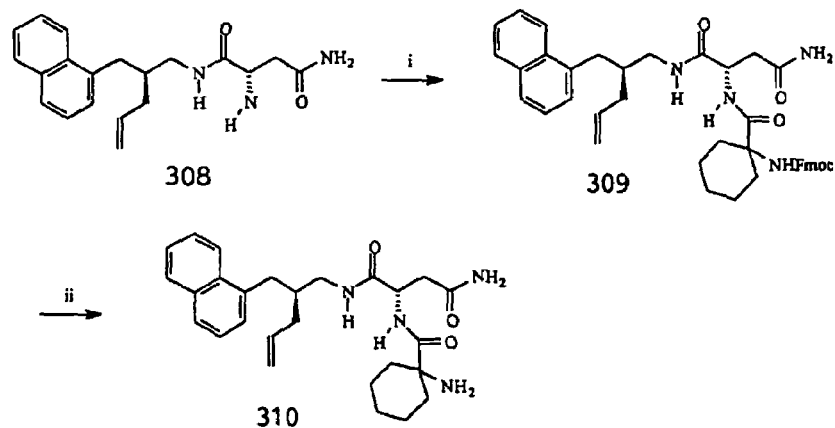
FIG. 28 depicts a reaction scheme for the preparation of compound 310. Reagents and conditions: (i) Fmoc-1-aminocyclohexanecarboxylic acid, HOBt, EDCI.HCl, r.t. overnight, 66%; (ii) Piperidine, $CH_3CN$, r.t., 1.5 h, 85.8%.
Figure 29:
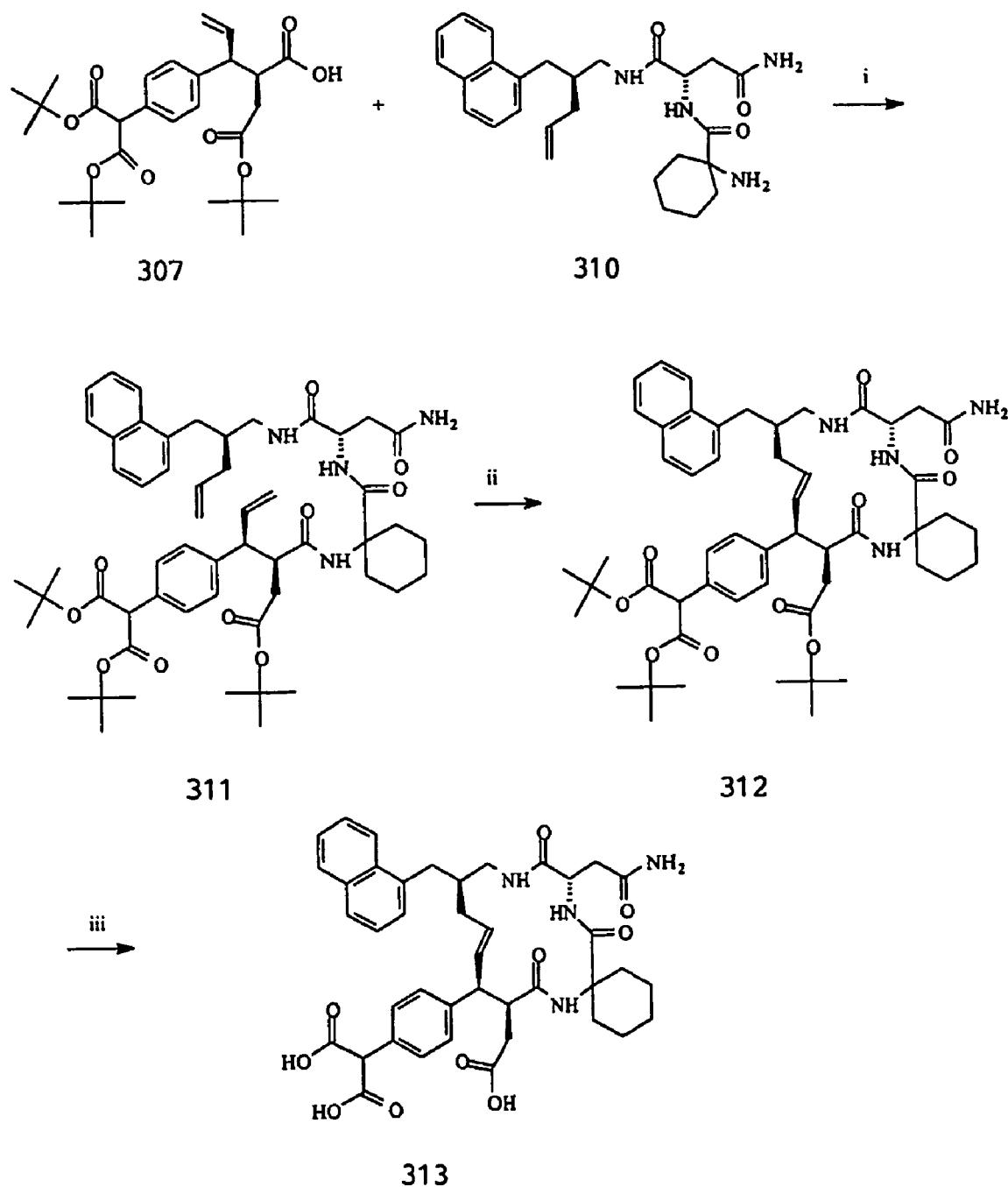
FIG. 29 depicts a reaction scheme for the preparation of compound 313. Reagents and conditions: (i) HOAt, EDCI.HCl, DMF, 50° C., 24 h, 21%. (ii) Grubb's reagent, $CH_2Cl_2$, reflux, 40 h, 24%.

Compound 233 is effective in inhibiting cell growth in erbB-2 driven breast cancer cells (FIG. 26). $IC_{50}$ is less than 1 μM. Compound 233 is effective in both extracellular and intracellular binding assays.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A compound of the formula

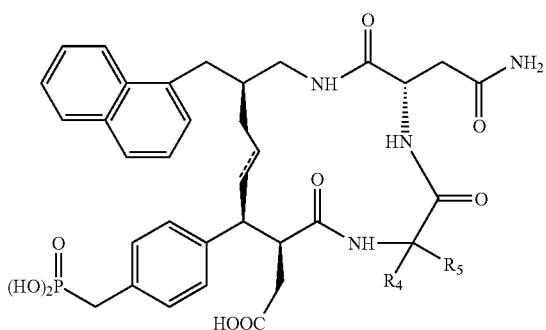

wherein $R_4$ and $R_5$ together form cyclohexyl.

2. A compound of the formula

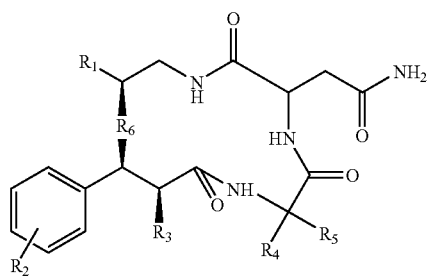

wherein $R_1$ is aralkyl, arylheterocyclylalkyl, alkylaminocarbonyl, alkenylaminocarbonyl, arylaminocarbonyl, alkoxyalkyl, aryloxyalkyl, or aralkoxyalkyl, wherein the aryl portion is phenyl or naphthyl and the alkyl portion is a $C_1$-$C_6$ alkyl, and the heterocyclyl is a 3-7 membered ring having at least one of N, O, and S; $R_2$ is dicarboxyalkyl, $R_3$ is carboxyalkyl, $R_4$ and $R_5$ together form cycloalkyl, and $R_6$ is a $C_2$-$C_4$ alkenylenyl group.

3. The compound of claim 2, which has the formula:

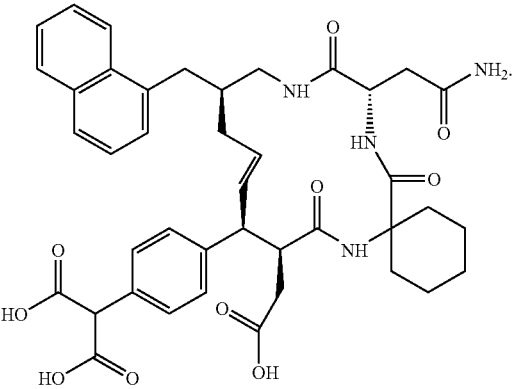

4. A pharmaceutical composition comprising a pharmaceutically acceptable carrier and a compound of claim 1.

5. A pharmaceutical composition comprising a pharmaceutically acceptable carrier and an effective amount of a compound of claim 2.

6. A pharmaceutical composition comprising a pharmaceutically acceptable carrier and a compound of claim 3.

7. A method for inhibiting an SH2 domain from binding with a phosphoprotein comprising contacting an SH2 domain with an effective amount of a compound of claim 1.

8. A method for breast cancer in a mammal comprising administering to the mammal an effective amount of a compound of claim 1.

9. A method for inhibiting cell motility or angiogenesis in a mammal comprising administering to said mammal an effective amount of a compound claim 1.

10. A method for inhibiting an SH2 domain from binding with a phosphoprotein comprising contacting an SH2 domain with an effective amount of a compound of claim 2.

11. A method for breast cancer in a mammal comprising administering to the mammal an effective amount of a compound of claim 2.

12. A method for inhibiting cell motility or angiogenesis in a mammal comprising administering to said mammal an effective amount of a compound of claim 2.

13. A method for inhibiting an SH2 domain from binding with a phosphoprotein comprising contacting an SH2 domain with an effective amount of a compound of claim 3.

14. A method for treating breast cancer in a mammal comprising administering to the mammal an effective amount of a compound of claim 3.

15. A method for inhibiting cell motility or angiogenesis in a mammal comprising administering to said mammal an effective amount of a compound of claim 3.

* * * * *